US012616779B1

(12) United States Patent
Nam et al.

(10) Patent No.: US 12,616,779 B1
(45) Date of Patent: May 5, 2026

(54) PIEZOELECTRIC NERVE GUIDANCE AND REGENERATION

(71) Applicant: The Regents of the University of California, Oakland, CA (US)

(72) Inventors: Jin Nam, Irvine, CA (US); Hyle B. Park, Riverside, CA (US); Karen Low, Rancho Santa Margarita, CA (US); Gerardo Rene Ico, Rialto, CA (US)

(73) Assignee: The Regents Of The University Of California, Oakland, CA (US)

( * ) Notice: Subject to any disclaimer, the term of this patent is extended or adjusted under 35 U.S.C. 154(b) by 1143 days.

(21) Appl. No.: 17/580,007

(22) Filed: Jan. 20, 2022

Related U.S. Application Data

(63) Continuation of application No. 16/295,980, filed on Mar. 7, 2019, now abandoned.

(Continued)

(51) Int. Cl.
*A61N 7/00* (2006.01)
*A61L 27/16* (2006.01)
(Continued)

(52) U.S. Cl.
CPC ............... *A61L 27/50* (2013.01); *A61L 27/16* (2013.01); *A61N 1/36103* (2013.01);
(Continued)

(58) Field of Classification Search
CPC ....... A61N 1/36103; A61N 2007/0026; H10N 30/702; A61L 2430/32; A61L 2400/12
See application file for complete search history.

(56) References Cited

U.S. PATENT DOCUMENTS 9,334,476 B2 * 5/2016 Arinzeh .................. A61L 27/16
9,771,557 B2 * 9/2017 Arinzeh .............. A61L 27/3895
(Continued)

FOREIGN PATENT DOCUMENTS

WO     WO-8806866 A1 * 9/1988 ......... A61B 17/1128

OTHER PUBLICATIONS

Delaviz et al., "Repair of Peripheral Nerve Defects Using a Polyvinylidene Fluoride Channel Containing Nerve Growth Factor and Collagen Gel in Adult Rats" Cell Journal vol. 13, No. 3, Autumn 2011, pp. 137-142 (Year: 2011).*
(Continued)

*Primary Examiner* — Colin T. Sakamoto
(74) *Attorney, Agent, or Firm* — Knobbe, Martens, Olson & Bear, LLP

(57) ABSTRACT

A method of activating a piezoelectric neuroconduit guide scaffold including a plurality of aligned piezoelectric polymer nanofibers, the method including mechanically stimulating the piezoelectric neuroconduit guide scaffold with hydro-acoustic waves or shockwaves to remotely activate a piezoelectric effect of the nanofibrous scaffolds that induces a mechano-electrical stimulus on neural cells cultured on the scaffold, wherein the mechano-electrical stimulus promotes nerve fiber outgrowth from the neuronal cells. Some aspects relate to seeding individual components of neural tissues on the piezoelectric neuroconduit guide scaffold, wherein the hydro-acoustic stimulation induces neural tissue formation. In other aspects, the piezoelectric neuroconduit guide scaffold is implanted in a damaged neural tissue, wherein stimulating the piezoelectric neuroconduit guide scaffold by the application of shockwaves promotes nerve fiber outgrowth that bridges a nerve gap to induce nerve regeneration or reinnervation of the damaged neural tissue.

23 Claims, 44 Drawing Sheets

Specification includes a Sequence Listing.

Aligned PVDF nanofiber mat

Non-contact mechanical stimulation

Related U.S. Application Data

(60) Provisional application No. 62/639,895, filed on Mar. 7, 2018.

(51) Int. Cl.

| | |
|---|---|
| *A61L 27/50* | (2006.01) |
| *A61N 1/36* | (2006.01) |
| *C12N 5/00* | (2006.01) |
| *C12N 5/071* | (2010.01) |
| *C12N 5/0793* | (2010.01) |
| *H10N 30/00* | (2023.01) |

(52) U.S. Cl.
CPC ....... *A61N 1/36125* (2013.01); *C12N 5/0068* (2013.01); *C12N 5/0619* (2013.01); *C12N 5/0697* (2013.01); *H10N 30/702* (2024.05); *A61L 2400/12* (2013.01); *A61L 2430/32* (2013.01); *A61N 2007/0026* (2013.01); *C12N 2527/00* (2013.01); *C12N 2533/30* (2013.01); *C12N 2539/00* (2013.01)

(56) References Cited

U.S. PATENT DOCUMENTS

2010/0324697 A1* 12/2010 Arinzeh ............... C12N 5/0618
623/23.72
2017/0051251 A1* 2/2017 Arinzeh ............... C12N 5/0068

OTHER PUBLICATIONS

Delaviz et al., "Ultrastructural Changes in Spinal Motoneurons and Locomotor Functional Study after Sciatic Nerve Repair in Conduit Tube" Iranian Journal of Basic Medical Sciences vol. 15, No. 4, Jul.-Aug. 2012. pp. 990-996 (Year: 2012).*

Lee et al., "Neurite extension of primary neurons on electrospun piezoelectric scaffolds". Acta Biomaterialia, vol. 7, Issue 11, Nov. 2011, pp. 3877-3886. (Year: 2011).*

Lee et al., "The Influence of Piezoelectric Scaffolds on Neural Differentiation of Human Neural Stem/Progenitor Cells". Tissue Engineering Part A, vol. 18, No. 19-20, 2012, pp. 2063-2072 (Year: 2012).*

Park et al., "Ultrasound-stimulated peripheral nerve regeneration within asymmetrically porous PLGA/Pluronic F127 nerve guide conduit". Journal of Biomedical Materials Research Part B: Applied Biomaterials, vol. 94B, Issue 2, Aug. 2010, pp. 287-507 (Year: 2010).*

Lee et al., "Effects of Extracorporeal Shock Wave Therapy on Functional Recovery and Neurotrophin-3 Expression in the Spinal Cord After Crushed Sciatic Nerve Injury in Rats", Ultrasound in Medicine & Biology, vol. 41, Issue 3, Mar. 2015, pp. 790-796 (Year: 2015).*

Hitscherich, Pamela, et al., The Effect of PVDF-TrFE Scaffolds on Stem Cell Derived Cardiovascular Cells, Biotechnology and Bioengineering, 2016, vol. 113, No. 7, pp. 1577-1585.

Ico, Gerardo, et al., "ize-dependent piezoelectric and mechanical properties of electrospun P(VDF-TrFE) nanofibers for enhanced energy harvesting," Journal of Materials Chemistry A, 2016, vol. 4, pp. 2293-2304.

Lee, Yee-Shuan, et al., "Neurite extension of primary neurons on electrospun piezoelectric scaffolds", Acta Biomaterialia 7 (2011), pp. 3877-3886.

* cited by examiner (A)

(B)

Aligned PVDF nanofiber mat

Non-contact mechanical stimulation

High Voltage (B)

Dimension of scaffold exposed to mechanical stimulation: 0.5 cm x 1.4 cm (A)

Top casing

Cell-seeded PVDF scaffold

Silicone o-ring

Bottom casing

~500 μm

SEQUENCE LISTING

<160> NUMBER OF SEQ ID NOS: 42

<210> SEQ ID NO 1
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 1
cccgagaagt ttcagcacat c                                         21

<210> SEQ ID NO 2
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 2
ttccaggccc atggtacaat                                           20

<210> SEQ ID NO 3
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 3
tgcgcctaga aaccagacct t                                         21

<210> SEQ ID NO 4
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 4
tgtaccacat ccgccttgg                                            19

<210> SEQ ID NO 5
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 5
tggaacgccg agtacgaagt a                                         21

<210> SEQ ID NO 6
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 6
atggcagtga tagcgaaggc t                                         21

<210> SEQ ID NO 7
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 7
aaactccccc atgtggaaga c                                                    21

<210> SEQ ID NO 8
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 8
atgcccgcac tcacaatatt g                                                    21

<210> SEQ ID NO 9
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 9
gagctggcag aagaacagga ac                                                   22

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 10
tgaacacgaa gtgagctgcc t                                                    21

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
ggcaaattca acggcacagt                                                      20

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 12
gcgctggaac agagattgga a                                                    21

<210> SEQ ID NO 13
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 13
gatgccatgc tgatgttcga c                                                    21

-continued

```
<210> SEQ ID NO 14
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 14
ttttgtccga gaccgagaag c                                          21

<210> SEQ ID NO 15
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 15
accttgtgtc tgccaccatg a                                          21

<210> SEQ ID NO 16
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 16
aagccattgt gtccgaacca                                            20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 17
atcgccacat tgctcagcta g                                          21

<210> SEQ ID NO 18
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 18
acgccaaaga ggaacagca                                             19

<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 19
tggcatcatc gtcacaacgt                                            20

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer
```

-continued

<400> SEQUENCE: 20
tgccctgctg gaagataaca c                                                           21

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 21
tggagctcaa tgaccgcttt                                                             20

<210> SEQ ID NO 22
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 22
ctgagcaatc tgtctttccc agt                                                         23

<210> SEQ ID NO 23
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 23
tcaccacgga ggaaacgcta t                                                           21

<210> SEQ ID NO 24
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 24
tcgctcctgg aagatggtga t                                                           21

<210> SEQ ID NO 25
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 25
tggtatccca aggaaatgca g                                                           21

<210> SEQ ID NO 26
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 26
atgtcctcgc tctcaaacgt g                                                           21

<210> SEQ ID NO 27

-continued

```
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 27
catgagcgtc ttggtttttcc g                                              21

<210> SEQ ID NO 28
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 28
caccatgttc acagccagct t                                               21

<210> SEQ ID NO 29
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 29
gagcggaaga gcagtttgtc a                                               21

<210> SEQ ID NO 30
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 30
tgagagccac cattgatcac a                                               21

<210> SEQ ID NO 31
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 31
tccatggcca agttcaggt                                                  19

<210> SEQ ID NO 32
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 32
cccagttcgt ccatttttcg                                                 20

<210> SEQ ID NO 33
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 33
```

```
tgcagccagt tgtagcagat g                                          21

<210> SEQ ID NO 34
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 34
gctcgaagct ggttcagttc a                                          21

<210> SEQ ID NO 35
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 35
tgtgtatgca gaggttcaag cct                                        23

<210> SEQ ID NO 36
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 36
tcaatggctg aggacttgtc g                                          21

<210> SEQ ID NO 37
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 37
ggttccagag gccaacatca a                                          21

<210> SEQ ID NO 38
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 38
aggcaaacac caggagccat a                                          21

<210> SEQ ID NO 39
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 39
agcaagtacc atggaccatg c                                          21

<210> SEQ ID NO 40
<211> LENGTH: 19
<212> TYPE: DNA
```

-continued

```
<213> ORGANISM: Artificial Sequence
<220> FEATURE:
<223> OTHER INFORMATION: oligonucleotide primer

<400> SEQUENCE: 40
taaagaagcg cccgatgga                                              19

<210> SEQ ID NO 41
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 41
agtgatgttg acaaggcggt g                                          21

<210> SEQ ID NO 42
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 42
cggtcacgcg catttatctt                                            20
```

PIEZOELECTRIC NERVE GUIDANCE AND REGENERATION

FIELD OF THE INVENTION

Piezoelectric neuroconduit guide scaffolds, including a plurality of aligned piezoelectric polymer nanofibers, for supporting axon regeneration in neural tissues. The scaffolds can be safely activated in vivo to promote nerve fiber outgrowth.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 54948146_1.TXT, the date of creation of the ASCII text file is Jan. 20, 2022, and the size of the ASCII text file is 8.39 KB.

BACKGROUND OF THE INVENTION

Severe injuries to the peripheral and central nervous system present a significant clinical problem due to limited or lack of treatment for fully functional recovery. When the nerve is damaged by injuries/diseases, such as peripheral nerve transection, spinal cord injury, and diabetic neuropathy, a cascade of cellular events occurs to the affected and neighboring cells, extracellular matrix (ECM) of the injury site, and the nerve tissue. Functional regeneration of damaged nerves from the central nervous system (CNS) is very limited due to rapid glial scar tissue formation. Although the peripheral nervous system (PNS) is more capable of nerve regeneration than the CNS, appropriate clinical solutions for nerve damage with large gaps have yet to be found. Recently, various nerve regeneration strategies, such as using nerve guidance conduits, hydrogels, cell-based therapies, and electrical stimulation, have been explored to enhance nerve repair by promoting a regeneration-permissive environment or inhibiting factors that prevent regrowth from occurring.

Although the PNS possesses a certain degree of regenerative capabilities, the regeneration of nerve injuries with large gaps is limited by the rate of axonal elongation. Native Schwann cells eventually advance ahead of the regenerating axons, no longer providing a sufficient environment for axon growth (Son Y-J, Trachtenberg J T, Thompson W J. Schwann cells induce and guide sprouting and reinnervation of neuromuscular junctions. Trends in neurosciences. 1996; 19(7): 280-5). Another issue with injuries of large nerve gaps is that the disorganization of axon extensions from the growth cone continues to increase as the length of the nerve gap increases (Menorca R M, Fussell T S, Elfar J C. Peripheral nerve trauma: mechanisms of injury and recovery. Hand clinics. 2013; 29(3):317; Ertürk A, Hellal F, Enes J, Bradke F. Disorganized microtubules underlie the formation of retraction bulbs and the failure of axonal regeneration. Journal of Neuroscience. 2007; 27(34):9169-80). Therefore, efforts have focused on enhancing the outcome of peripheral nerve regeneration through the use of neuroconduits to guide and provide a supportive environment for successful axon regeneration.

The current gold standard to repair transected nerve is autologous nerve grafting. This method provides the structural support to guide axon regeneration, preventing the formation of neuromas (Millesi H. Bridging defects: autologous nerve grafts. How to improve the results of peripheral nerve surgery. 2007:37-8). Because the autograft is surgically removed from the patient's own body, most commonly taken from the sural nerve of the calf region, it acts as an immunogenically inert scaffold, providing viable Schwann cells and appropriate neurotrophic factors for axon regeneration (Dahlin L, Lundborg G. Use of tubes in peripheral nerve repair. Neurosurgery Clinics of North America. 2001; 12(2):341-52). However, this technique possesses many limitations, including the necessity of multiple surgeries, the induction of a functionally impaired region where the graft was taken from, and disproportion of graft to nerve tissue in size and structure. Furthermore, the patient is at high risk of neuroma formation in the transplanted area. Alternative clinical options include cadaver allografts (Kim B S, Yoo J J, Atala A. Peripheral nerve regeneration using acellular nerve grafts. Journal of biomedical materials research Part A. 2004; 68(2):201-9), veins and arteries as grafts (Battiston B, Geuna S, Ferrero M, Tos P. Nerve repair by means of tubulization: literature review and personal clinical experience comparing biological and synthetic conduits for sensory nerve repair. Microsurgery. 2005; 25(4):258-67), and natural/synthetic conduits, but each of these possess their own disadvantages. When using allografts, patients require systemic immunosuppression, putting them at risk of associated morbidity from immunomodulatory therapy (Udina E, Verdn E, Navarro X. Effects of the immunophilin ligand FK506 on nerve regeneration in collagen guides seeded with Schwann cells in rats. Neuroscience letters. 2004; 357(2): 99-102); vein and artery grafts is structurally inferior to nerve tissue therefore the walls may collapse and it cannot bridge nerve gaps greater than 30 mm (Karabekmez F E, Duymaz A, Moran S L. Early clinical outcomes with the use of decellularized nerve allograft for repair of sensory defects within the hand. SAGE Publications Sage C A: Los Angeles, CA; 2009); and lastly, current clinically-approved natural and synthetic conduits have not been able to repair completely transected nerves with gaps greater than 30 mm to regain full functionality (Kehoe S, Zhang X F, Boyd D. FDA approved guidance conduits and wraps for peripheral nerve injury: A review of materials and efficacy. Injury. 2012; 43(5):553-72). To address these limitations, more biologically active forms of biomaterials, including the incorporation of cellular/molecular factors and/or the use of electroactive precursor materials, are currently being investigated. Natural Conduits Natural biomaterials for neuroconduits are typically either: (1) autologous non-neural tissues and decellularized allogenic/xenogenic neural/non-neural tissues or (2) naturally-derived polymers including ECM proteins (collagen, laminin, hyaluraonan) and polysaccharides (agarose, chitosan). Avance® offers commercially available human decellularized nerve allografts. Studies showed that Avance® improved nerve functional recovery of sensory, motor, and mixed nerves with nerve gaps up to 30 mm (Neubauer D, Graham J B, Muir D. Chondroitinase treatment increases the effective length of acellular nerve grafts. Experimental neurology. 2007; 207(1):163-70; and Whitlock E L, Tuffaha S H, Luciano J P, Yan Y, Hunter D A, Magill C K, et al. Processed allografts and type I collagen conduits for repair of peripheral nerve gaps. Muscle & Nerve. 2009; 39(6):787-99). However, the use of the allografts requires additional administration of immunosuppressants for 18 months as well as it is limited in repairing transected nerve gap lengths less than 30 mm. On the other hand, naturally-derived polymeric neuroconduits are immunologically inert. There are several of these neuroconduits that have been FDA approved and are commercially available to use in the clinical setting. NeuroGen®, a commercially available conduit made of collagen type I, showed improved sensory scores for a variety of nerves, but was limited to nerve gaps of an average 13 mm (Whitlock E L, Tuffaha S H, Luciano J P, Yan Y, Hunter D A, Magill C K, et al. Processed allografts and type I collagen conduits for repair of peripheral nerve gaps. Muscle & Nerve. 2009; 39(6):787-99). The common limitation of the wide variety of tested materials is that none have shown reliable success for nerve gaps greater than 30 mm.

Synthetic Conduits

Silicone neuroconduits were the first to demonstrate the feasibility of synthetic materials for nerve repair by bridging nerve defects up to 15 mm (Merle M, Lee Dellon A, Campbell J N, Chang P S. Complications from silicon-polymer intubulation of nerves. Microsurgery. 1989; 10(2): 130-3). However, due to its immunogenic non-permeable properties, the implanted conduit induced permanent fibrotic tissue formation ultimately leading to nerve compression. This led to the development of absorbable synthetic conduits. Biodegradable synthetic biomaterials, including polyglycolic acid (PGA) and poly(D,L-lactide-co-F-caprolactone) (PCL), have been investigated as a scaffolding material for nerve regeneration. PGA, an FDA-approved biomaterial, has been shown have 86% functional recovery of nerve defects less than 30 mm (Mackinnon S E, Dellon A L. Clinical nerve reconstruction with a bioabsorbable polyglycolic acid tube. Plastic and reconstructive surgery. 1990; 85(3):419-24). Yet, PGA rapidly degrades to lactic acid in 90 days, possibly before the completion of nerve regeneration (de Tayrac R, Oliva-Lauraire M-C, Guiraud I, Henry L, Vert M, Mares P. Long-lasting bioresorbable poly (lactic acid)(PLA94) mesh: a new approach for soft tissue reinforcement based on an experimental pilot study. International Urogynecology Journal. 2007; 18(9):1007-14). PCL, another FDA-approved biomaterial, produces less acidic degradation byproducts (Sun H, Mei L, Song C, Cui X, Wang P. The in vivo degradation, absorption and excretion of PCL-based implant. Biomaterials. 2006; 27(9):1735-40). However, it has reported only a 25% meaningful recovery of nerve defects up to 20 mm (Chiriac S, Facca S, Diaconu M, Gouzou S, Liverneaux P. Experience of using the bioresorbable copolyester poly (DL-lactide-ε-caprolactone) nerve conduit guide Neurolac™ for nerve repair in peripheral nerve defects: report on a series of 28 lesions. Journal of Hand Surgery (European Volume). 2012; 37(4): 342-9). Neurotube®, made of PGA, and Neurolac®, made of poly(D,L-lactide-co-F-caprolactone) are neuroconduits that are FDA-approved and commercially available.

As compared to the PNS, the CNS has a much more limited capacity to self-regeneration. Therefore, traumatic injuries and diseases are very debilitating to the patient, often leading to loss of motor, sensory, and cognitive functions, especially for injuries occurring in the C4 or C5 of the cervical spinal cord (Michael J, Krause J S, Lammertse D P. Recent trends in mortality and causes of death among persons with spinal cord injury. Archives of physical medicine and rehabilitation. 1999; 80(11):1411-9). The inability of neurons to regenerate after an injury is due to the inhibitive microenvironment created by the presence of inhibitory factors and lack of axon-growth promoting factors (Dumont R J, Okonkwo D O, Verma S, Hurlbert R J, Boulos P T, Ellegala D B, et al. Acute spinal cord injury, part I: pathophysiologic mechanisms. Clinical neuropharmacology. 2001; 24(5):254-64). Currently there are no cures for injuries in the CNS, there are only a few treatment options to delay the progression of CNS diseases. Two main strategies for current CNS treatment include: neuroprotection and neuroprosthetics. Neuroprotection refers to the inhibition of the death of CNS neural cells. Neuroprosthetics refers to the use of devices that can substitute or complement the damaged/loss of a motor, sensory or cognitive modality.

Due to rapid tissue degeneration/glial scar tissue formation, it is advantageous to immediately begin treatment at the onset of a traumatic injury to prevent complete neurological death. Specifically for spinal cord injury, after the patient is immobilized to prevent further neural damage, methylprednisolone, a glucocorticoid, can be administered within 8 hours of injury to reduce damage to nerve cells and decrease inflammation (Bracken M B, Shepard M J, Holford T R, Leo-Summers L, Aldrich E F, Fazl M, et al. Administration of methylprednisolone for 24 or 48 hours or tirilazad mesylate for 48 hours in the treatment of acute spinal cord injury: results of the Third National Acute Spinal Cord Injury Randomized Controlled Trial. Jama. 1997; 277(20):1597-604). Currently, methylprednisolone is the only approved pharmacotherapy for spinal cord injury, but it has not shown clinically significant effects.

Another treatment to compensate the loss of functional upper extremities is the use of neuroprosthetics. Individuals with C4 or C5 damage in the spinal cord suffer from tetraplegia, the functional loss of upper and lower extremities. Damage occurring at the C5 range results in limitation or completely loss of finger functionality; where as C4 damage also includes limited or loss of function of the hands and elbow movement (White N-H, Black N-H. Spinal cord injury (SCI) facts and figures at a glance. 2016). Individuals lose their ability to accomplish basic daily tasks and their independence. Neuroprostheses utilizes electrical stimulation on downstream nerves in the forearms, giving individuals the ability to reach, grasp, and pinch with their hands. Commercially available grasp neuroprostheses have been offered to patients at very early stage of rehabilitation (Rupp R, Rohm M, Schneiders M, Kreilinger A, Müller-Putz G R. Functional rehabilitation of the paralyzed upper extremity after spinal cord injury by noninvasive hybrid neuroprostheses. Proceedings of the IEEE. 2015; 103(6):954-68). However, current neuroprosthetics cannot provide full motor, sensing or cognitive functionality. Therefore, ongoing research is still seeking strategies to restoring full functionality by complete repair of CNS nerves.

Due to the innate electrical properties of the nervous system, the potential of utilizing electrical stimulation to enhance nerve regeneration and functional recovery has been widely investigated. Electrical stimulation has been shown to facilitate the processes of axonal regeneration by enhancing the secretion of neurotrophic factors from glial cells and promoting neurite outgrowth (Kanzaki S, Stöver T, Kawamoto K, Prieskorn D M, Altschuler R A, Miller J M, et al. Glial cell line-derived neurotrophic factor and chronic electrical stimulation prevent VIII cranial nerve degeneration following denervation. Journal of Comparative Neurology. 2002; 454(3):350-60; and Al-Majed A A, Neumann C M, Brushart T M, Gordon T. Brief electrical stimulation promotes the speed and accuracy of motor axonal regeneration. Journal of Neuroscience. 2000; 20(7):2602-8). Several in vivo studies demonstrated the efficacy of electrical stimulation promoting nerve outgrowth in rat models of nerve injury, resulting in earlier muscle reinnervation and functional recovery. When electrical stimulation was applied at the time of nerve damage, this resulted in an increased number of sensory neurons that expressed BDNF and its trkB receptor, subsequently accelerating nerve regeneration (Geremia N M, Gordon T, Brushart T M, Al-Majed A A, Verge V M. Electrical stimulation promotes sensory neuron regeneration and growth-associated gene expression. Experimental neurology. 2007; 205(2):347-59). Another study showed that the application of electrical stimulation enhanced nerve regeneration as all the motor neurons had regenerated their axons into the motor nerve branch within 21 days instead of 56-70 days observed in the sham control (Brushart T. Motor axons preferentially reinnervate motor pathways. Journal of Neuroscience. 1993; 13(6):2730-8). Similarly, the first human clinical trial showed a promising potential of therapeutic electrical stimulation, where improved post-surgical outcomes were achieved by localized low frequency of electrical stimulation on patients with carpal tunnel syndrome (Gordon T, Amirjani N, Edwards D C, Chan K M. Brief post-surgical electrical stimulation accelerates axon regeneration and muscle reinnervation without affecting the functional measures in carpal tunnel syndrome patients. Experimental neurology. 2010; 223(1): 192-202). However, the electrode approach can activate only neuron(s) in direct contact with or close proximity to the electrodes, resulting in a small localized effective area.

To overcome this limitation, conductive nerve guidance conduits were investigated to implement electrical stimulation throughout the length of the damaged nerve as a means to guide the regeneration and regrowth of axons while reducing the infiltration of fibrous tissue. Several in vitro studies demonstrated enhanced neurite elongation of neuronal cells under electrical stimulation via conductive polymer scaffolds (Zhang Z, Rouabhia M, Wang Z, Roberge C, Shi G, Roche P, et al. Electrically conductive biodegradable polymer composite for nerve regeneration: electricity-stimulated neurite outgrowth and axon regeneration. Artificial Organs. 2007; 31(1):13-22; Gomez N, Schmidt C E. Nerve growth factor-immobilized polypyrrole: Bioactive electrically conducting polymer for enhanced neurite extension. Journal of biomedical materials research Part A. 2007; 81(1):135-49; Schmidt C E, Shastri V R, Vacanti J P, Langer R. Stimulation of neurite outgrowth using an electrically conducting polymer. Proceedings of the National Academy of Sciences. 1997; 94(17):8948-53; and Kotwal A, Schmidt C E. Electrical stimulation alters protein adsorption and nerve cell interactions with electrically conducting biomaterials. Biomaterials. 2001; 22(10):1055-64). In vivo, Xu et al. recently showed enhanced functionality of regenerated nerve using a PPy-PDLLA conduit in a rat sciatic nerve transection model, where a higher density of thick myelin sheaths of the cells in the PPy-PDLLA conduit was observed as compared to an autograft (Xu H, Holzwarth J M, Yan Y, Xu P, Zheng H, Yin Y, et al. Conductive PPY/PDLLA conduit for peripheral nerve regeneration. Biomaterials. 2014; 35(1):225-35). These studies collectively suggest a great potential of electrical stimulation to drive nerve regeneration. However, the application of electrical stimulation in the clinical setting is limited by several factors; most significantly, its invasive nature requires the implantation of electrodes protruding through the skin.

In this regard, piezoelectric materials provide an opportunity to develop an implant that can electrically stimulate cells/tissues without the necessity of electrical wire implantation due to their ability to self-generate electric fields under dynamic mechanical strain. Under the direct piezoelectric effect, the materials induce an electric charge separation by the re-orientation of dipole domains in response to mechanical deformation (tension or compression), providing a means to produce electric potentials without a separate electrical source (Vijaya M. Piezoelectric materials and devices: applications in engineering and medical sciences: CRC Press; 2012). Due to their flexibility and biocompatibility, piezoelectric polymers have been often used for biomedical applications over their inorganic counterparts. There have been several attempts to utilize piezoelectric properties for nerve regeneration (Fine E G, Valentini R F, Bellamkonda R, Aebischer P. Improved nerve regeneration through piezoelectric vinylidenefluoride-trifluoroethylene copolymer guidance channels. Biomaterials. 1991; 12(8): 775-80; and Aebischer P, Valentini R F, Dario P, Domenici C, Galletti P M. Piezoelectric guidance channels enhance regeneration in the mouse sciatic nerve after axotomy. Brain Research. 1987; 436(1):165-8). Especially, poly(vinylidene fluoride) (PVDF) and its copolymer poly(vinylidene fluoride-trifluoroethylene) (PVDF-TrFE), have been extensively studied for such applications due to their excellent biocompatibility and relatively high piezoelectricity (Teixeira L, Crippa G, Trabuco A, Gimenes R, Zaghete M, Palioto D, et al. In vitro biocompatibility of poly (vinylidene fluoride-trifluoroethylene)/barium titanate composite using cultures of human periodontal ligament fibroblasts and keratinocytes. Acta biomaterialia. 2010; 6(3):979-89; and Beloti M M, de Oliveira P T, Gimenes R, Zaghete M A, Bertolini M J, Rosa A L. In vitro biocompatibility of a novel membrane of the composite poly (vinylidene-trifluoroethylene)/barium titanate. Journal of biomedical materials research Part A. 2006; 79(2):282-8). The first patented use of PVDF and PVDF-TrFE as a nerve guidance conduit was demonstrated in a rat model (Aebischer P, Valentini R F, Galletti P M. Piezoelectric nerve guidance channels. Google Patents; 1988). The poled PVDF conduit was implanted into the sciatic nerve of a rat with a 4 mm gap. 4 weeks after implantation, there were significantly more myelinated axons than in the control group (Delaviz H, Faghihi A, Delshad A A, hadi Bahadori M, Mohamadi J, Roozbehi A. Repair of peripheral nerve defects using a polyvinylidene fluoride channel containing nerve growth factor and collagen gel in adult rats. Cell Journal (Yakhteh). 2011; 13(3):137). They also implanted the piezoelectric PVDF-TrFE conduit into a rat sciatic nerve with a 10 mm gap and observed bridging of myelinated axons in 4 weeks, demonstrating the capability of PVDF-TrFE as a nerve guidance conduit for nerve regeneration (Delaviz H, Faghihi A, Mohamadi J, Roozbehi A. Ultrastructural Changes in Spinal Motoneurons and Locomotor Functional Study after Sciatic Nerve Repair in Conduit Tube. Iranian journal of basic medical sciences. 2012; 15(4):990). More recently, a group of researchers exploited and patented the enhanced piezoelectricity of PVDF-TrFE scaffolds synthesized by electrospinning to accelerate neurite outgrowth of dorsal root ganglion neurons or promote neural differentiation of human neural stem/progenitor cells in vitro (Lee Y-S, Arinzeh T L. The influence of piezoelectric scaffolds on neural differentiation of human neural stem/progenitor cells. Tissue Engineering Part A. 2012; 18(19-20):2063-72; Lee Y-S, Collins G, Arinzeh T L. Neurite extension of primary neurons on electrospun piezoelectric scaffolds. Acta biomaterialia. 2011; 7(11):3877-86; Arinzeh T, Collins G, Lee Y S. System and Method For A Piezoelectric Scaffold For Nerve Growth and Repair. Google Patents; 2017; and Arinzeh T, Collins G, Lee Y S. Method for nerve growth and repair using a piezoelectric scaffold. Google Patents; 2016). In spite of favorable results in these in vivo and in vitro studies, they were likely unable to utilize the true potential of piezoelectricity as it requires dynamic straining of the materials to generate electric potentials. They attributed the enhancement of cellular behaviors to piezoelectric responses of the PVDF scaffold by cell exerting forces, but considering minimal straining possible by the cells, the effects were probably due to intrinsic surface charges of the material.

SUMMARY OF THE INVENTION

A lack of therapeutic technologies that enable electrically stimulating nervous tissues in a facile and clinically relevant manner has partly hindered the advancement in treating nerve injuries for full functional recovery. We have developed a novel strategy to: 1) synthesize piezoelectric scaffolds, and 2) remotely activate the scaffolds without physically connected electric wires, to produce optimal electric fields in vitro and in vivo for the enhanced nerve regeneration. Unlike biochemical-embedded conduit in which the release of neurotrophic factors is limited by loading or electro-conductive conduit in which only passive electrical stimulation by autologous cells is possible without intrusive electrodes, the piezoelectric conduit provides unlimited opportunity to properly stimulate the neuronal cells in vivo. Specifically, a piezoelectric scaffold was developed using electrospinning technology and its piezoelectric performance was optimized by controlling the fiber diameter and scaffold thickness. The effects of electrical stimulation via acoustic activation of the scaffolds were examined on neuronal cells including neurons, Schwann cells and neural stem cells, where the stimulation enhanced neurite formation and elongation in neuronal cells, and promoted the maturation of Schwann cells to myelinating phenotype and the production of neurotrophic protein, and induced the differentiation of neural stem cells towards the functional cell types of the central nervous system including neurons, oligodendrocytes, and astrocytes. Therefore, this invention describes a novel method for enhancing nerve regeneration by modulating neuron and glial cell functionality for the repair of nerve injuries.

The piezoelectric neuroconduit guide scaffolds for supporting axon regeneration in neural tissues comprising a plurality of aligned piezoelectric polymer nanofibers. In some embodiments, the fibers have an average diameter of from 10-2000 nm. Average diameters may be 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm 950 nm, 1000 nm, 1150 nm, 1200 nm, 1250 nm, 1300 nm, 1350 nm, 1400 nm, 1450 nm, 1500 nm, 1550 nm, 1600 nm, 1650 nm, 1700 nm, 1750 nm, 1800 nm, 1850 nm, 1900 nm 1950 nm or 2000 nm. The scaffold comprises a fiber mat thickness of 10 to 1500 μm. In some embodiments, the fiber mat thickness is 20 μm, 30 μm, 40 μm, 50 μm, 60 μm, 70 μm, 80 μm 90 μm 100 μm, 110 μm, 120 μm, 130 μm, 140 μm, 150 μm, 160 μm, 170 μm, 180 μm, 190 μm 200 μm to 210 μm, 220 μm, 230 μm, 240 μm, 250 μm, 260 μm, 270 μm, 280 μm 290 μm 300 μm 350 μm, 400 μm, 450 μm or 500 μm.

Methods disclosed herein stimulate nerve tissue regeneration or reinnervation across a nerve gap. The nerve gap may be less or equal to 30 mm (e.g., 10 mm, 20 mm) or they may be greater than 30 mm, for example 40 mm, 50 mm, 100 mm, 150 mm, 200 mm, 250 mm, 300 mm, 350 mm, 400 mm, 450 mm or 500 mm.

Some embodiments relate to a piezoelectric neuroconduit guide scaffold for supporting axon regeneration in neural tissues including a plurality of aligned piezoelectric polymer nanofibers, wherein the fibers have an average diameter of from 100-1000 nm and wherein the scaffold comprises a fiber mat thickness of 40 to 400 μm.

In some embodiments, the fibers are all aligned within 200 of the neutral axis.

In some embodiments, the fibers are heat-treated.

In some embodiments, the piezoelectric polymer is poly (vinylidene fluoride) (PVDF) or a derivative thereof.

In some embodiments, the derivative of PVDF is P(VDF-trifluoroethanol) (PVDF-TrFE).

Some embodiments relate to a method of activating a piezoelectric neuroconduit guide scaffold as disclosed herein, the method including mechanically stimulating the piezoelectric neuroconduit guide scaffold with hydro-acoustic waves or shockwaves to remotely activate a piezoelectric effect of the nanofibrous scaffolds that induces a mechano-electrical stimulus on neuronal cells cultured on the scaffold, wherein the mechano-electrical stimulus promotes nerve fiber outgrowth from the neuronal cells.

In some embodiments, the piezoelectric scaffold is mechanically stimulated in a non-contact manner in vitro using a cell culture chamber with a vertical actuator.

In some embodiments, the method includes applying a mechanical strain having a strain of 0.02% to 0.04% with hydro-acoustic waves.

In some embodiments, the piezoelectric neuroconduit guide scaffold is mechanically stimulated in a non-contact manner in vivo using extracorporeal shockwave therapy (ESWT).

In some embodiments, the method includes applying a sonic pulse of mechanical energy having a positive peak within about 10 ns, followed by a negative peak up to about $-10$ MPa, with a total life cycle of about 10 μs.

In some embodiments, the hydro-acoustic waves or shockwaves generate a peak-to-peak voltage from the piezoelectric scaffolds of about 200 mVp-p, by simultaneously controlling individual fiber diameter and fiber mat thickness.

In some embodiments, the neuronal cells are selected from the group consisting of neurons, Schwann cells and neural stem cells.

Some embodiments relate to a method of engineering a nerve tissue including:

(a) seeding individual components of neural tissues including neuron and Schwann cells, or neural stem cells on the piezoelectric neuroconduit guide scaffold, and (b) hydro-acoustic stimulation of the cell/scaffold constructs to induce neural tissue formation.

In some embodiments, the neural tissue formation is in vitro.

Some embodiments relate to a method of stimulating nerve tissue regeneration or reinnervation including:

(a) implanting a piezoelectric neuroconduit guide scaffold of as disclosed herein in a damaged neural tissue, wherein the piezoelectric neuroconduit guide scaffold is positioned to bridge a nerve gap in the damaged neural tissue, and (b) activating the piezoelectric neuroconduit guide scaffold by the application of shockwaves to promote nerve fiber outgrowth, wherein the implanted scaffold and neurite outgrowth bridges the nerve gap to induce nerve regeneration or reinnervation of the damaged neural tissue.

In some embodiments, the neural tissue is in vivo.

In some embodiments, the nerve gap is larger than 30 mm.

In some embodiments, cellular activities of Schwann cells, or myelinating oligodendrocytes and extracellular matrix-producing astrocytes promote nerve regeneration within a PNS or CNS injury, respectively.

In some embodiments, the damaged neural tissue is in the peripheral nervous system (PNS).

In some embodiments, activating the piezoelectric neuroconduit guide scaffold induces upregulation of gene expression of one or more of pro-myelinating Schwaan cell markers, NGF, Krox20 or PMP22 and/or suppression of the immature Schwaan cell marker, NCAM-1.

In some embodiments, the damaged neural tissue is in the central nervous system (CNS).

In some embodiments, activating the piezoelectric neuroconduit guide scaffold induces upregulation of gene expression of one or more of oligodendrocyte cell markers, Olig1, Cldn11 and Mog and/or one or more astrocyte cell markers, Gfap, Cspg4 and Ntf3.

US 12,616,779 B1

11 cation of (B) the percentage of cell population bearing neurites, (C) the percentage of neurite-bearing cells possessing neurite lengths, within a certain range, greater than the nuclei length, and (D) the average neurite length. (Scale bar=100 μm)

Figure 21:
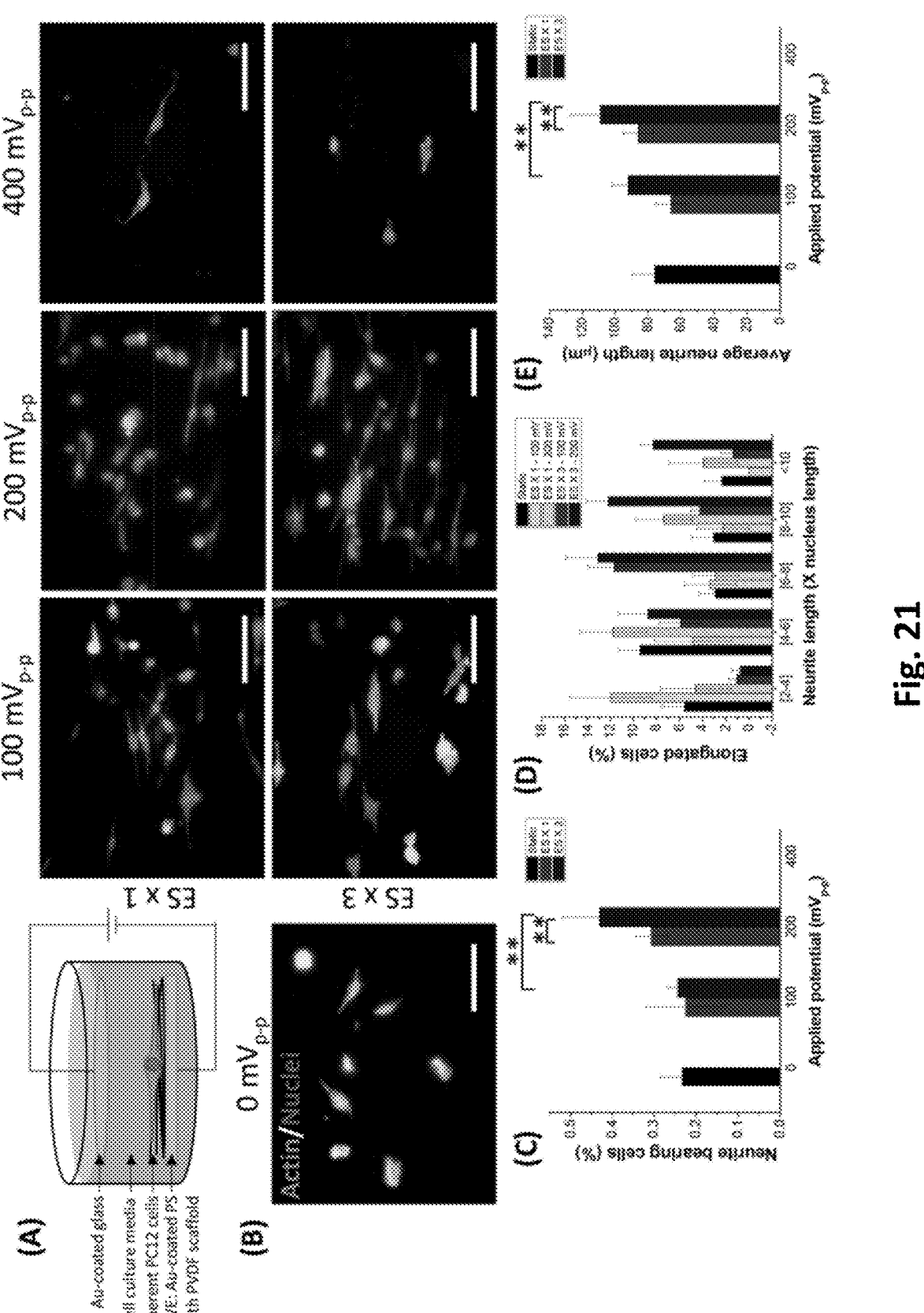

FIG. 21. Effect of electrical stimulation on neurite formation and elongation. (A) A schematic of the electrical stimulation set up. (B) Representative immunofluorescence images showing actin morphology of PC12 cells subjected to a single or multi-day application of 100, 200, and 400 mVp-p. Quantification of (C) the percentage of cell population bearing neurites, (D) the percentage of neurite-bearing cells possessing neurite lengths, within a certain range, greater than the nuclei length, and (E) the average neurite length. (Scale bar=100 μm)

Figure 22:
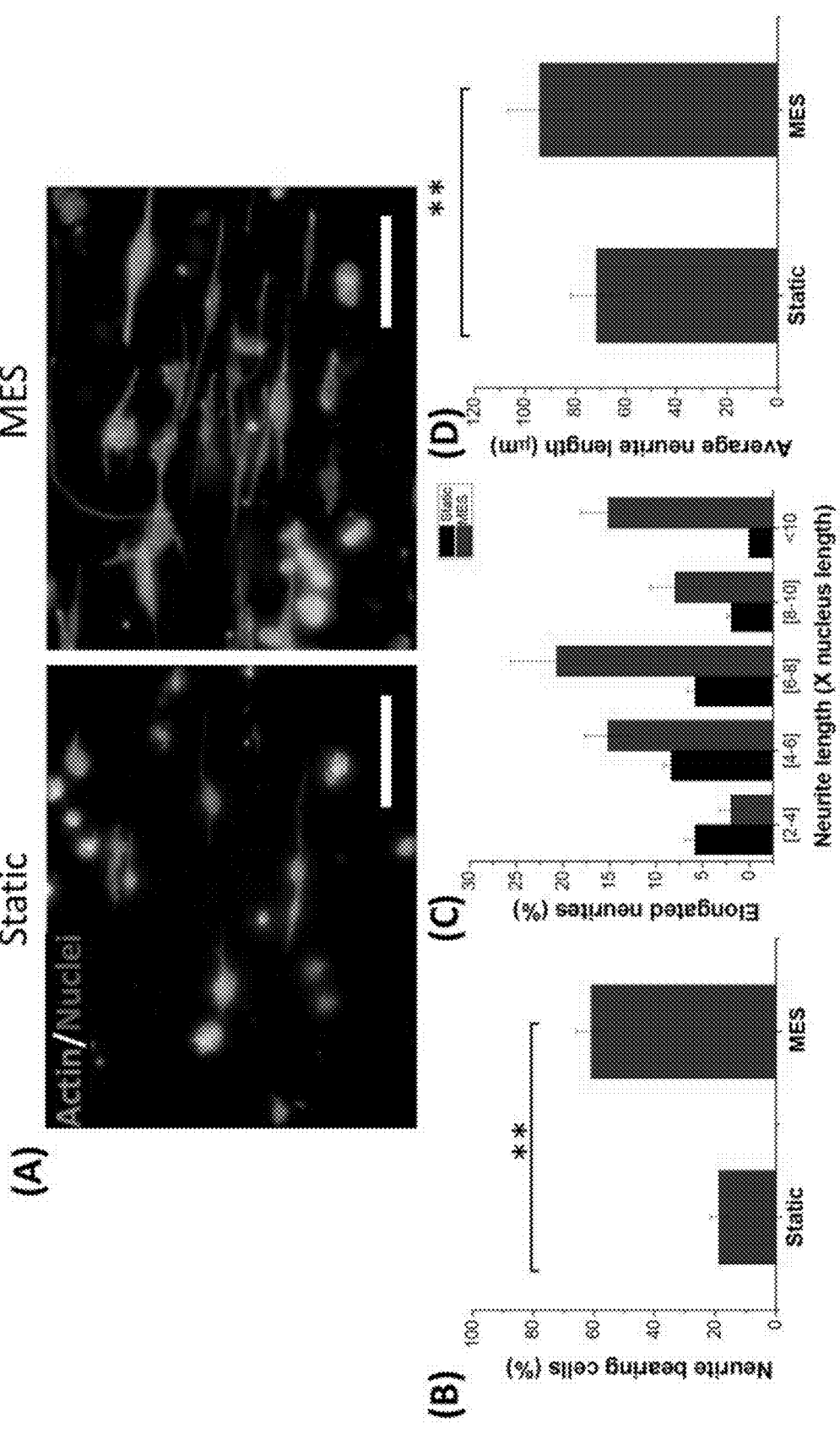

FIG. 22. Effects of mechanical/electrical stimulation on neurite formation and elongation. (A) Representative immunofluorescence images showing actin morphology of PC12 cells subjected to multi-day mechanical/electrical stimulation and static. Quantification of (B) the percentage of cell population bearing neurites, (C) the percentage of neurite-bearing cells possessing neurite lengths, within a certain range, greater than the nuclei length, and (D) the average neurite length. (Scale bar=100 μm)

Figure 23:
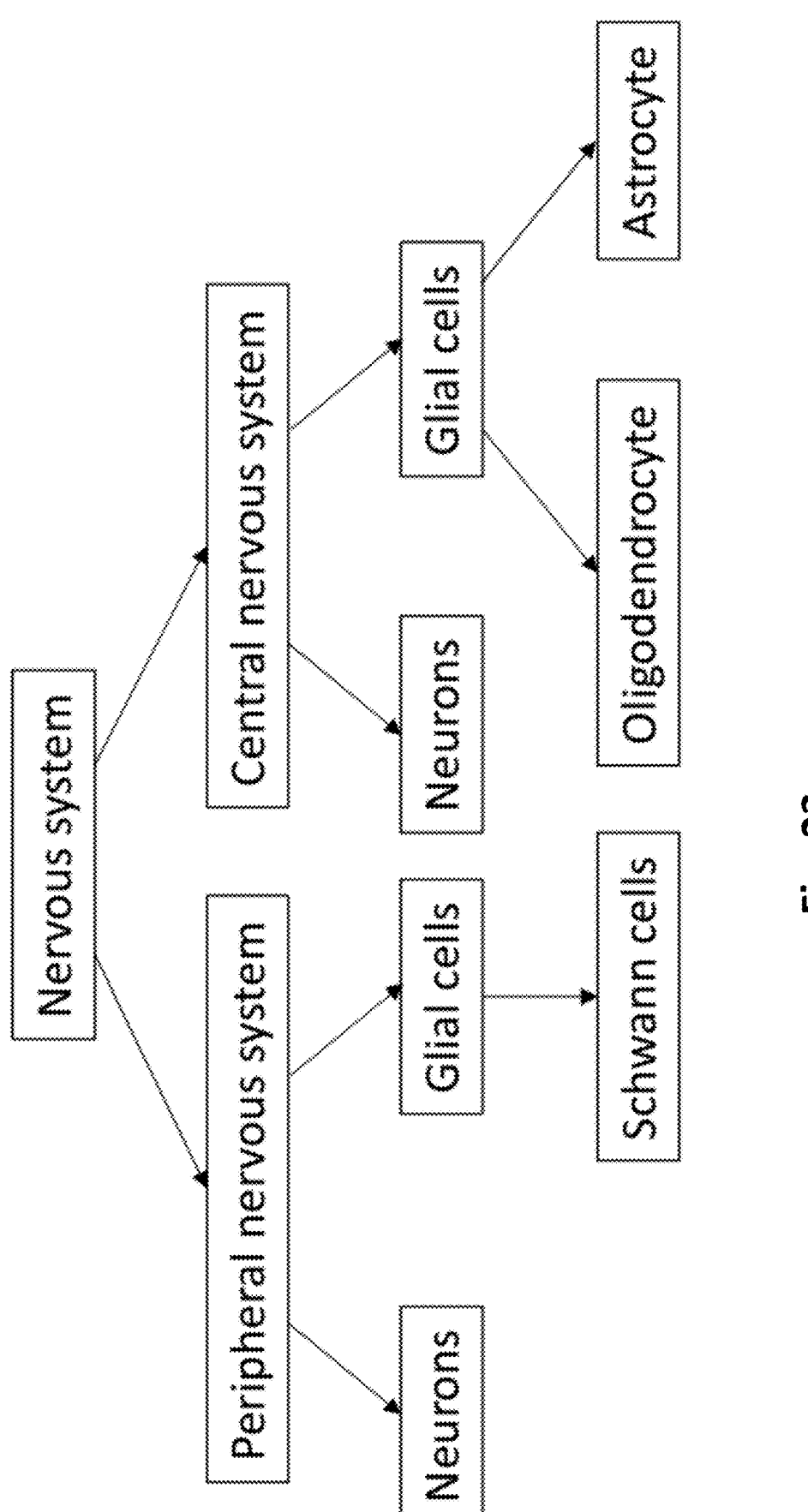

FIG. 23. Cellular components of the nervous system. The nervous system is broken down into the peripheral and central nervous system. Each system possesses their own neuronal and glial cell types.

Figure 24:
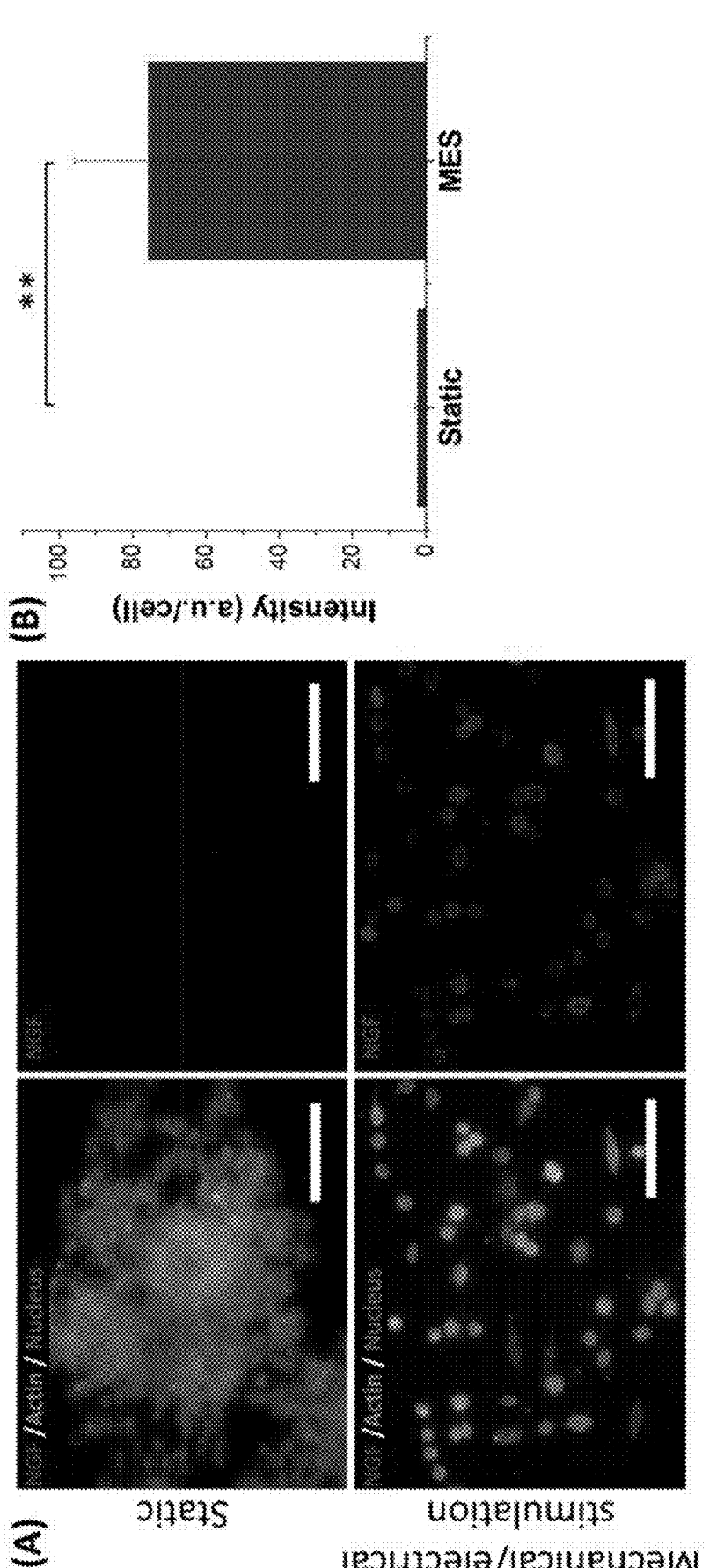

FIG. 24. NGF protein expression of RSC96 cells subjected to mechanical/electrical stimulation for 7 days. (A) Protein expression for secretory protein, NGF, of myelinating RSC96 cells cultured (A) statically or (B) subjected to mechanical/electrical stimulation on PVDF-TrFE. (B) The fluorescent intensity was compared between the two conditions. (Scale bar=100 μm)

Figure 25:
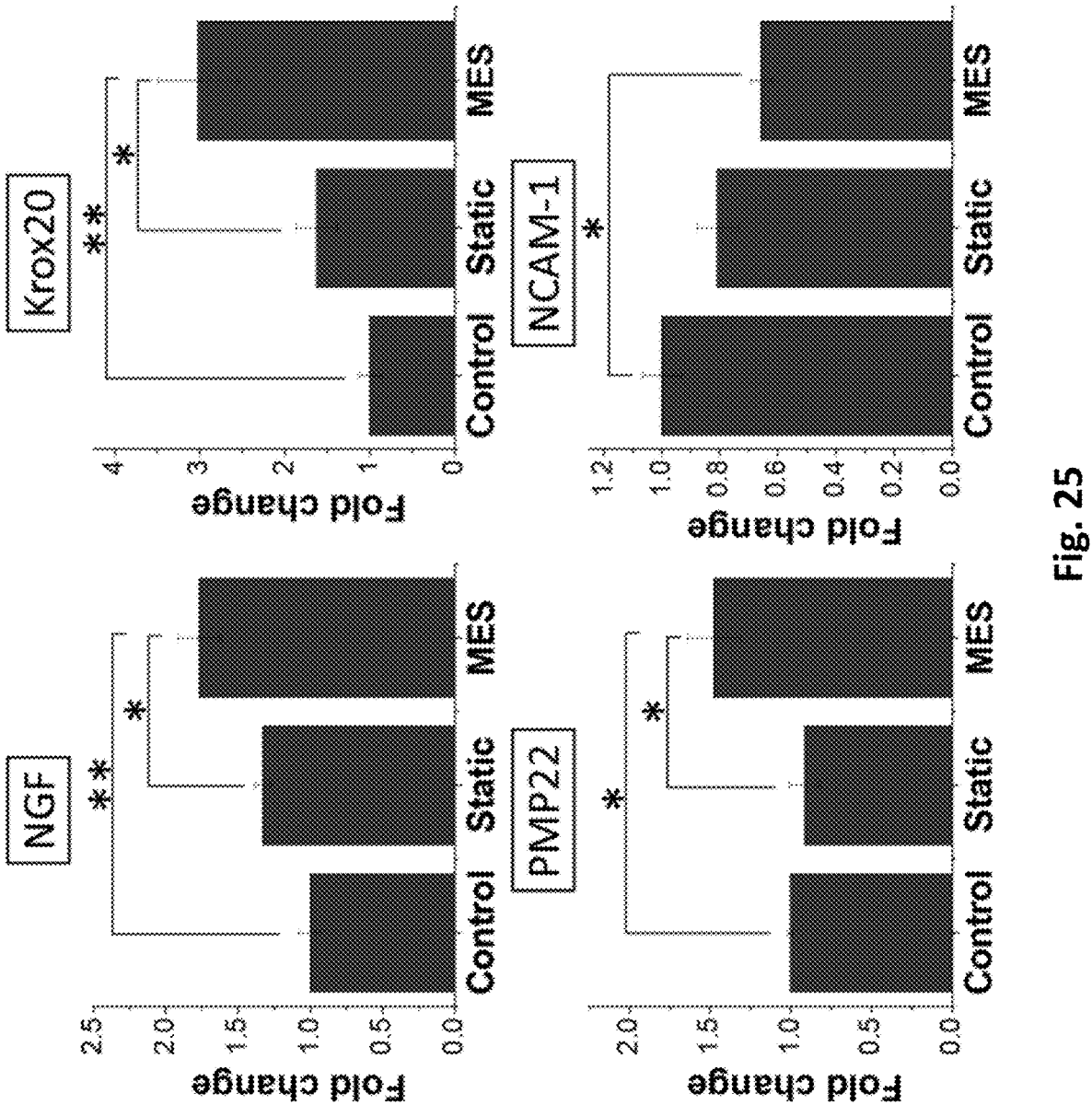

FIG. 25. The relative gene expression of RSC96 subjected to mechanical/electrical stimulation for 7 days determined by RT-PCR. Myelination markers (Krox20, PMP22, and NCAM-1) and secretion of NGF. The gene expression of RSC96 cultured on tissue culture plates was used as a control.

Figure 26:

FIG. 26. Nestin protein expression of mNSCs subjected to mechanical/electrical stimulation for 7 days. (A) Protein expression for neural stem cell marker, Nestin, of mNSC cultured statically or subjected to mechanical/electrical stimulation on PVDF-TrFE. (B) The fluorescent intensity was compared between the two conditions. (Scale bar=100 μm)

Figure 27:
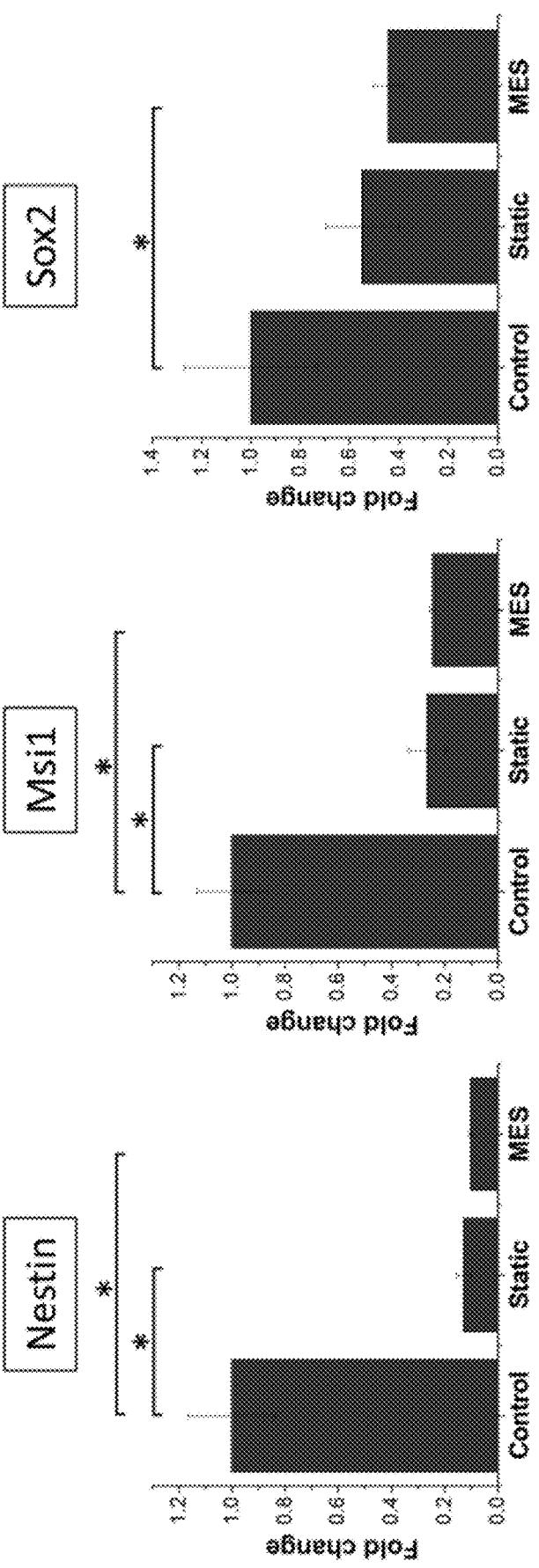

FIG. 27. The relative gene expression of neural stem cell markers of mNSCs subjected to mechanical/electrical stimulation for 7 days determined by RT-PCR. The gene expression of mNSC cultured on tissue culture plates was used as a control.

Figure 28:
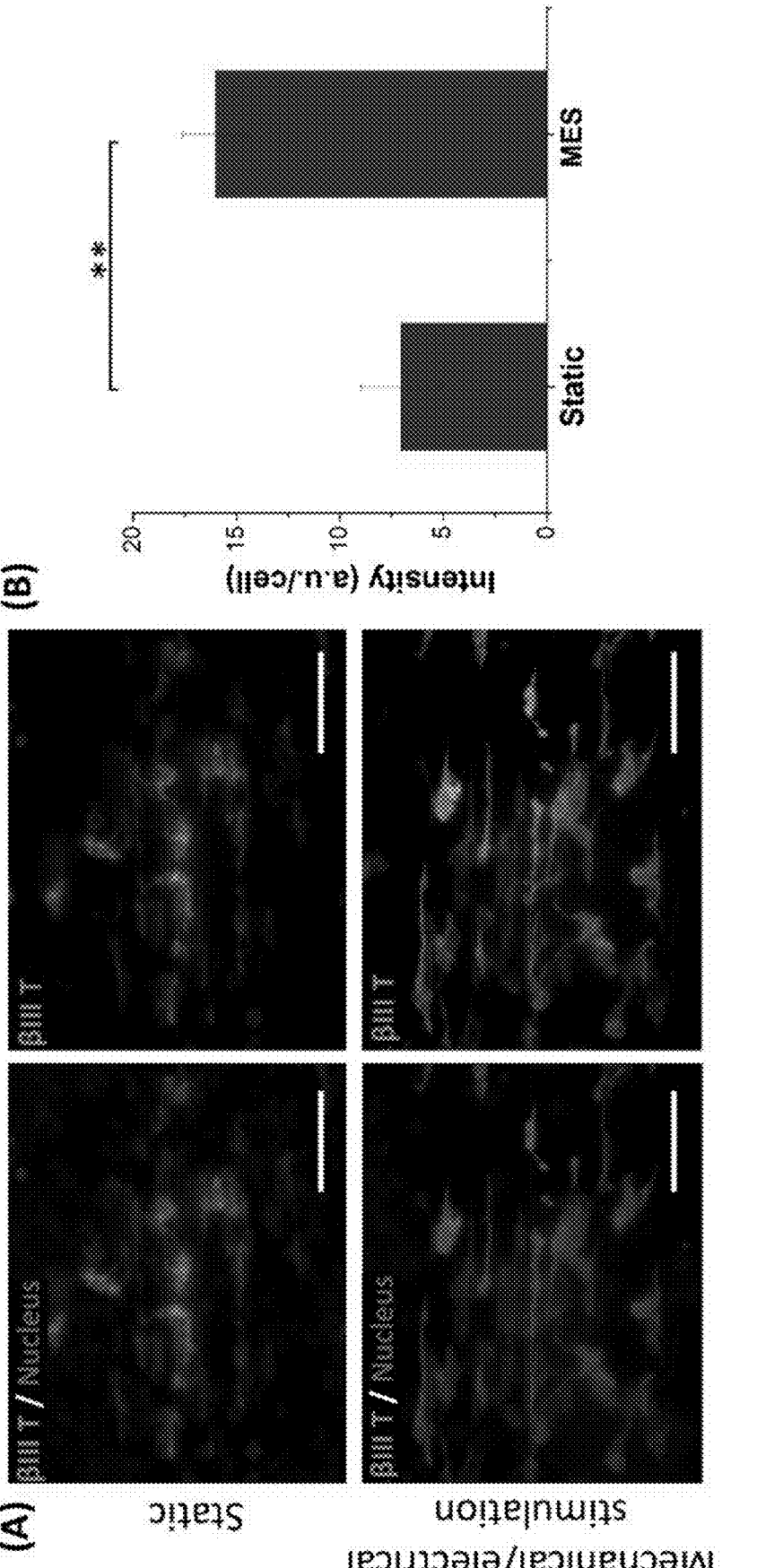

FIG. 28. βIII tubulin protein expression of mNSCs subjected to mechanical/electrical stimulation for 7 days. (A) Protein expression for neuronal marker, βIII tubulin, of mNSC cultured statically or subjected to mechanical/electrical stimulation on PVDF-TrFE. (B) The fluorescent intensity was compared between the two conditions. (Scale bar=100 μm)

Figure 29:
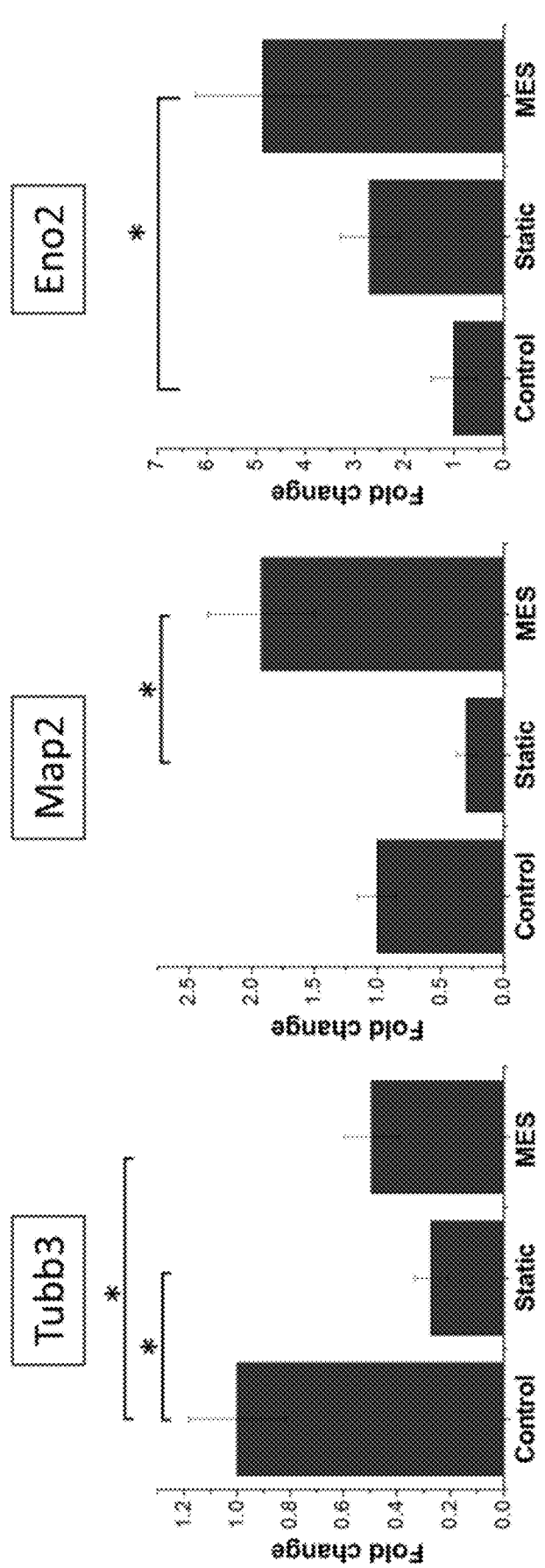

FIG. 29. The relative gene expression of neuron makers of mNSCs subjected to mechanical/electrical stimulation for 7 days determined by RT-PCR. The gene expression of mNSC cultured on tissue culture plates was used as a control.

Figure 30:
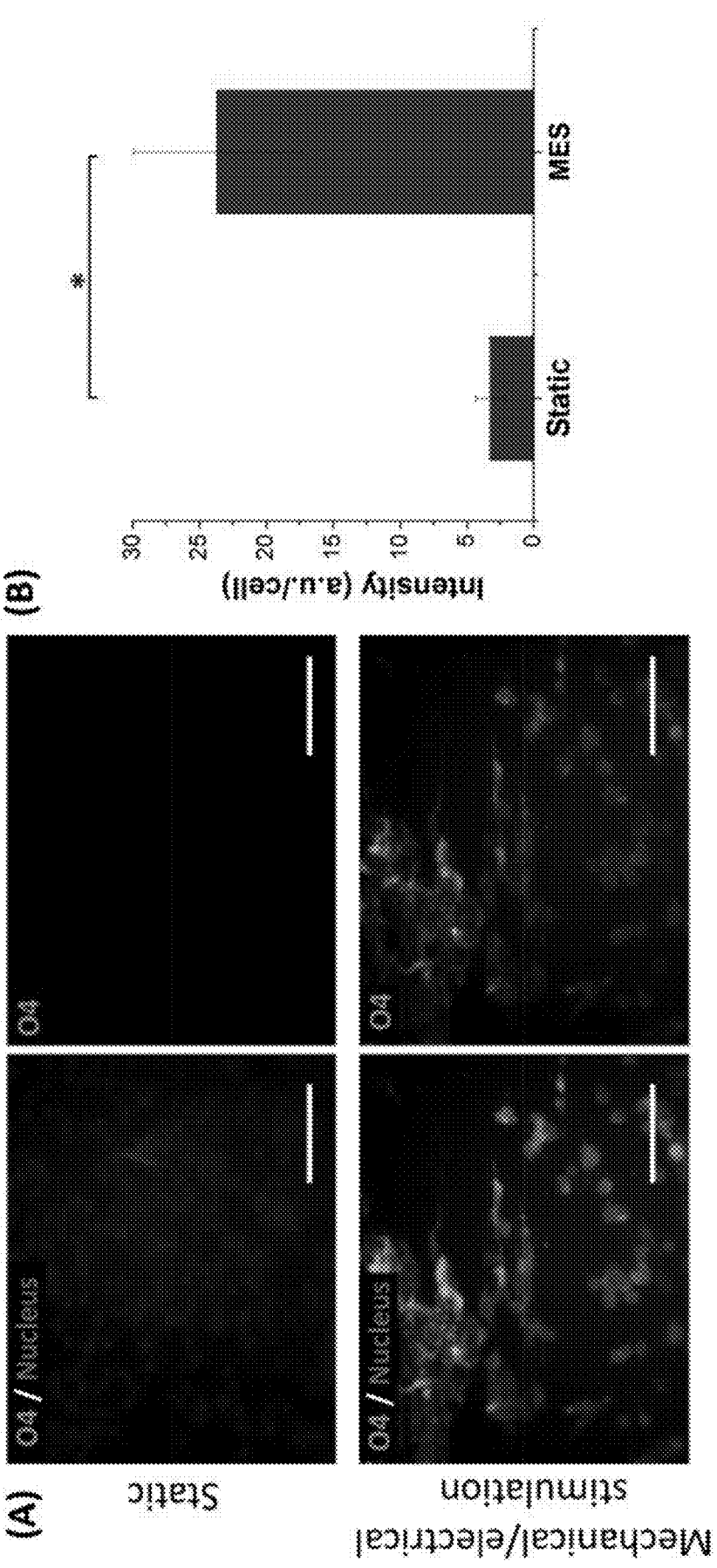

FIG. 30. O4 protein expression of mNSCs subjected to mechanical/electrical stimulation for 7 days. (A) Protein expression for oligodendrocyte marker, O4, of mNSC cultured statically or subjected to mechanical/electrical stimulation on PVDF-TrFE. (B) The fluorescent intensity was compared between the two conditions. (Scale bar=100 μm)

Figure 31:
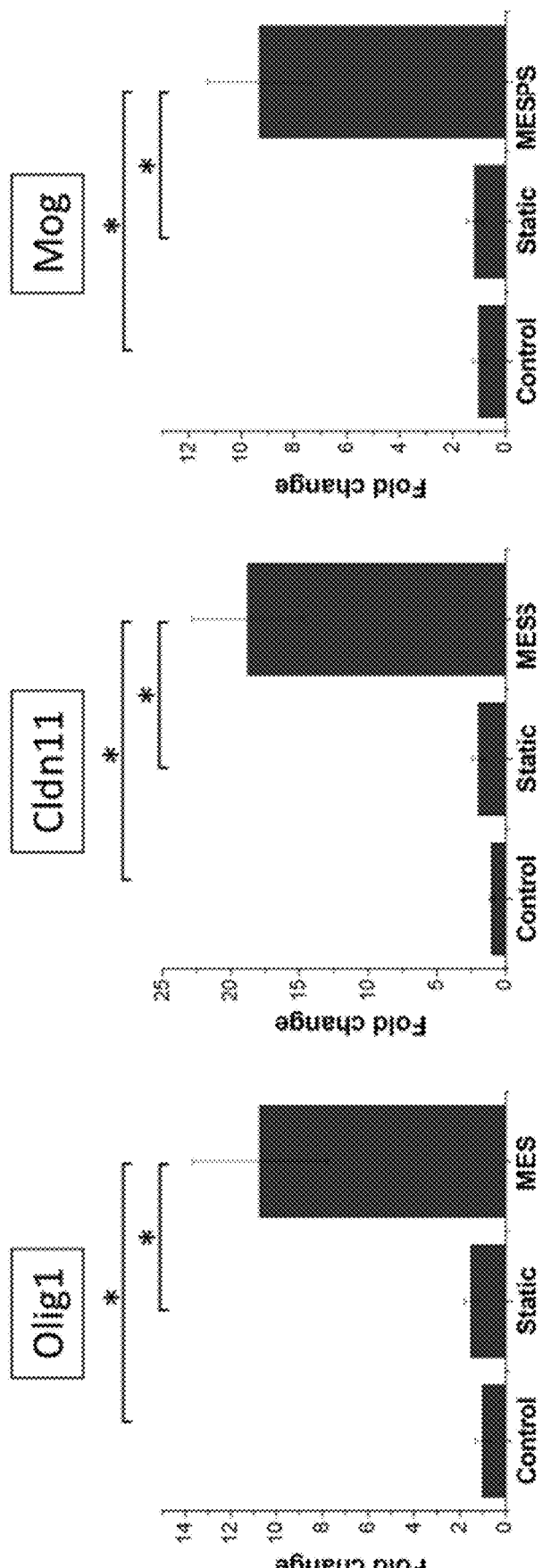

FIG. 31. The relative gene expression of oligodendrocyte markers of mNSCs subjected to mechanical/electrical stimulation for 7 days determined by RT-PCR. The gene expression of mNSC cultured on tissue culture plates was used as a control.

Figure 32:
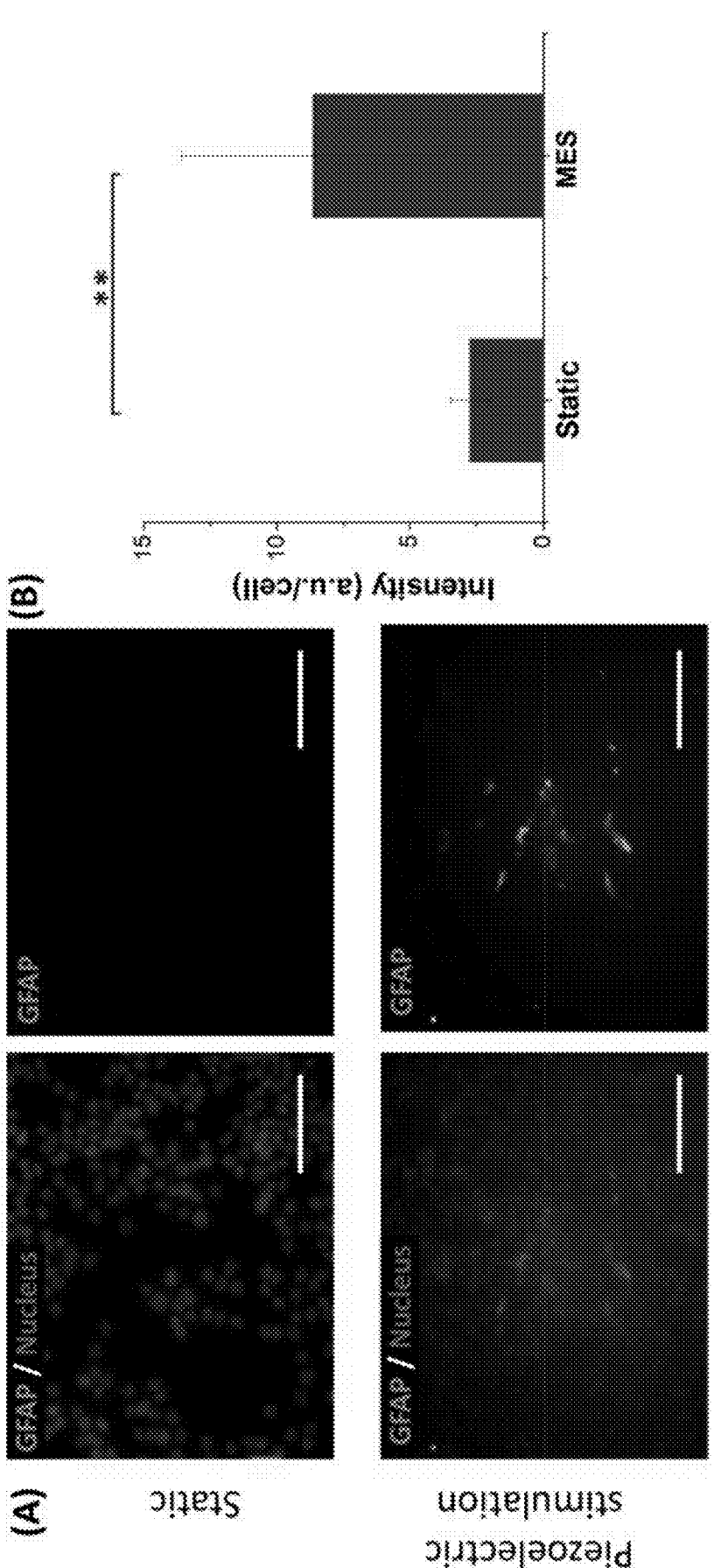

FIG. 32. GFAP protein expression of mNSCs subjected to mechanical/electrical stimulation for 7 days. (A) Protein expression for astrocyte marker, GFAP, of mNSC cultured statically or subjected to mechanical/electrical stimulation on PVDF-TrFE. (B) The fluorescent intensity was compared between the two conditions. (Scale bar=100 μm)

Figure 33:
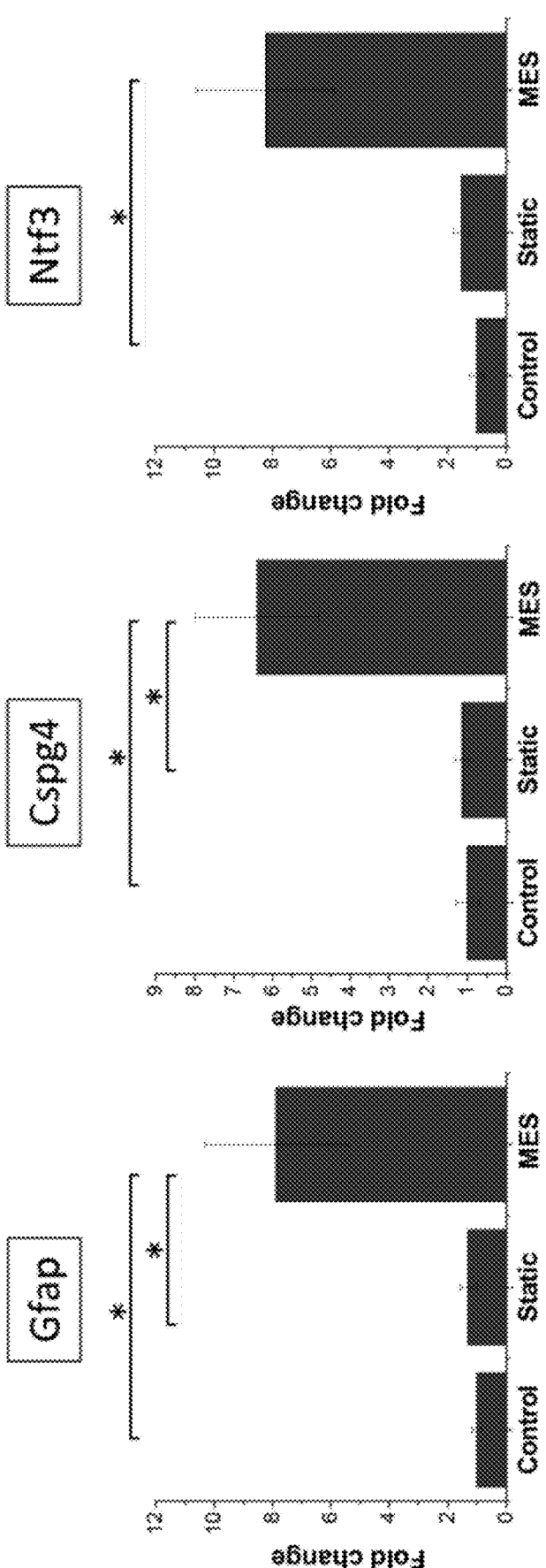

FIG. 33. The relative gene expression of astrocyte markers of mNSCs subjected to mechanical/electrical stimulation for 7 days determined by RT-PCR. The gene expression of mNSC.

Figure 34:
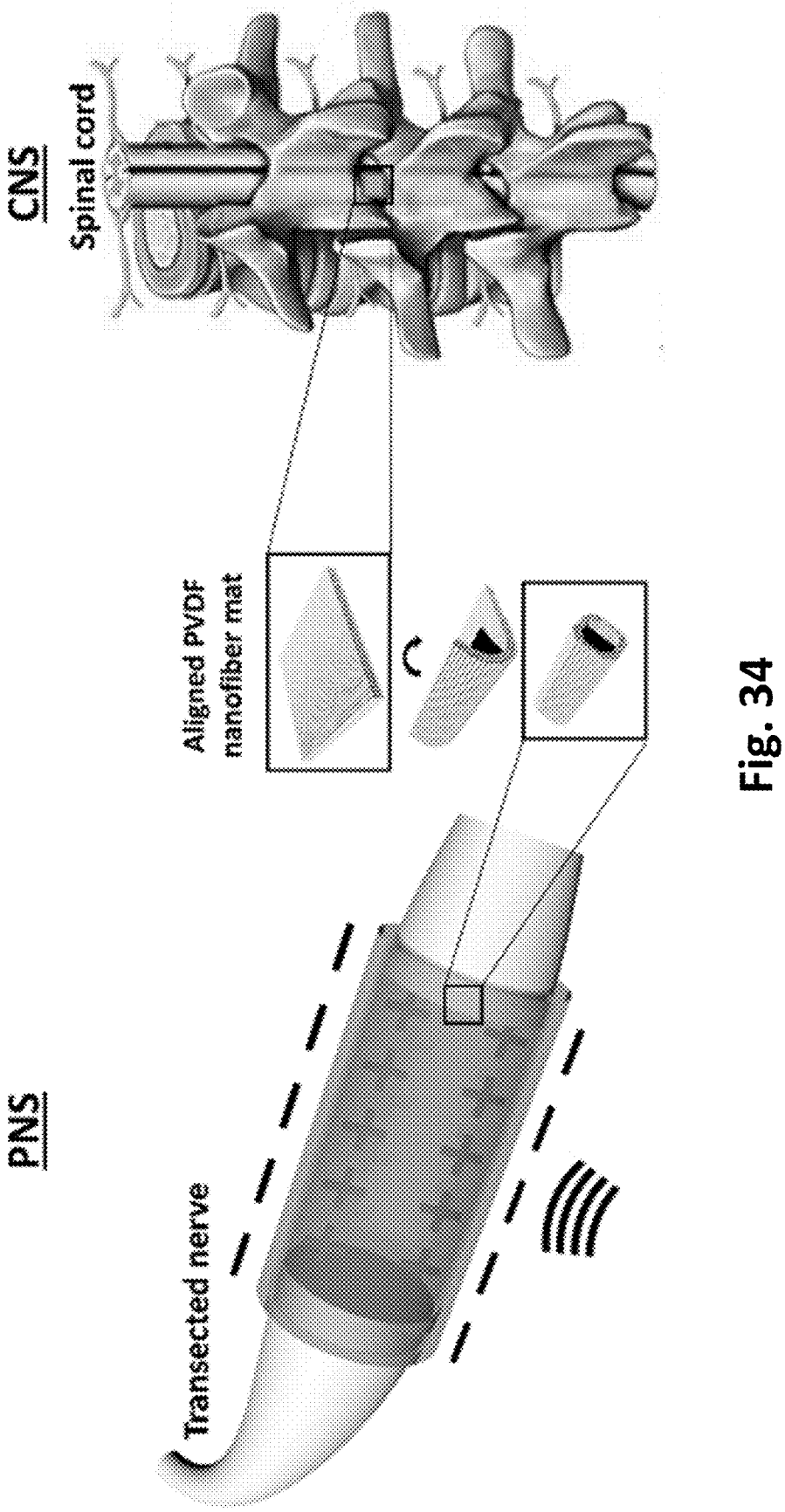

FIG. 34. A schematic of a piezoelectric neuroconduit composed of electrospun aligned PVDF-TrFE. Neuronal and glial cells are subjected to mechanical/electrical stimulation to enhance its outgrowth and functionality. The engineered tissue is used as an implanted neuroconduit which can be activated by externally applied mechanical stimulation to produce electric fields for enhancing and promoting nerve regeneration in the PNS and CNS.

Figure 35:
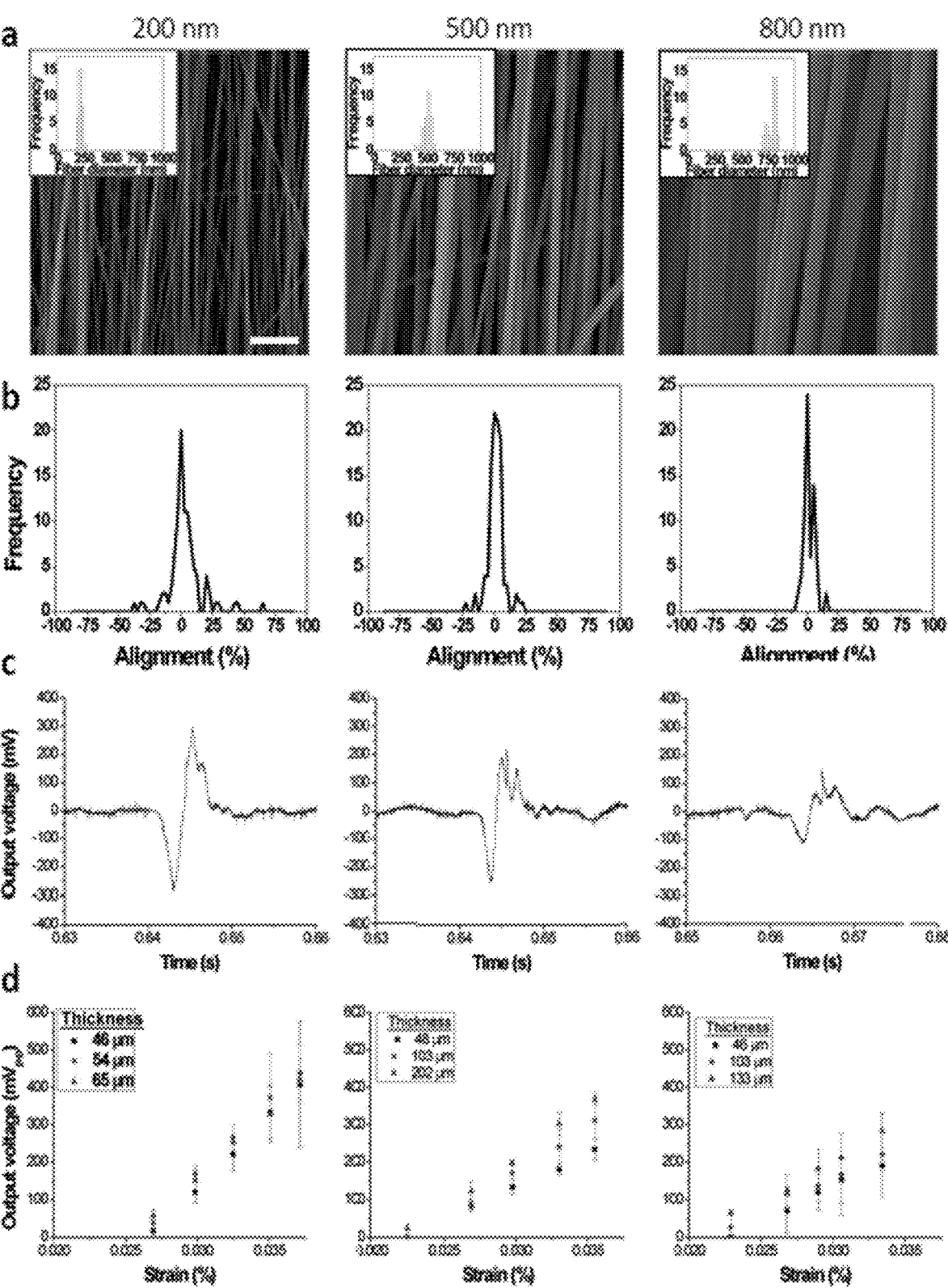

FIG. 35. Electrospun fiber. (a) Average fiber diameters of 200, 500, or 800 nm (inset: fiber diameter histogram, scale bar=2 μm). (b) High fiber alignment within 200 of the neutral axis. (c) Output voltage at a similar applied strain. (d) potential generation increased as the scaffold thickness increased for all fiber sizes.

Figure 36:
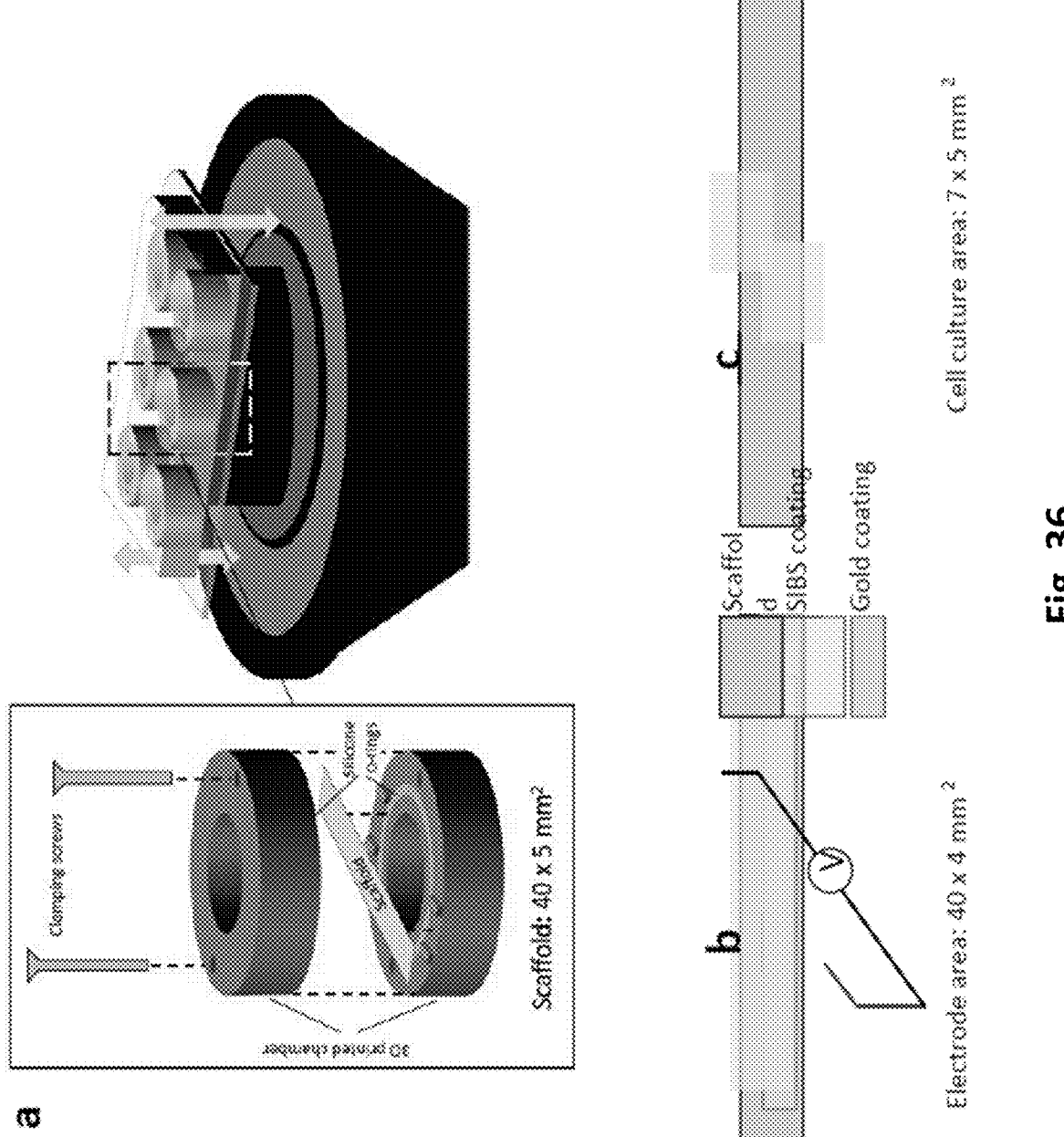

FIG. 36. (A) Fiber size-dependent piezoelectric performance of the electrospun PVDF scaffolds was determined by subjecting the samples to a vertical actuator at 3 Hz in an aqueous condition. (B) and (C) Gold electrodes with the dimension 40×4 mm² were sputtered on both sides of the scaffolds.

Figure 37:
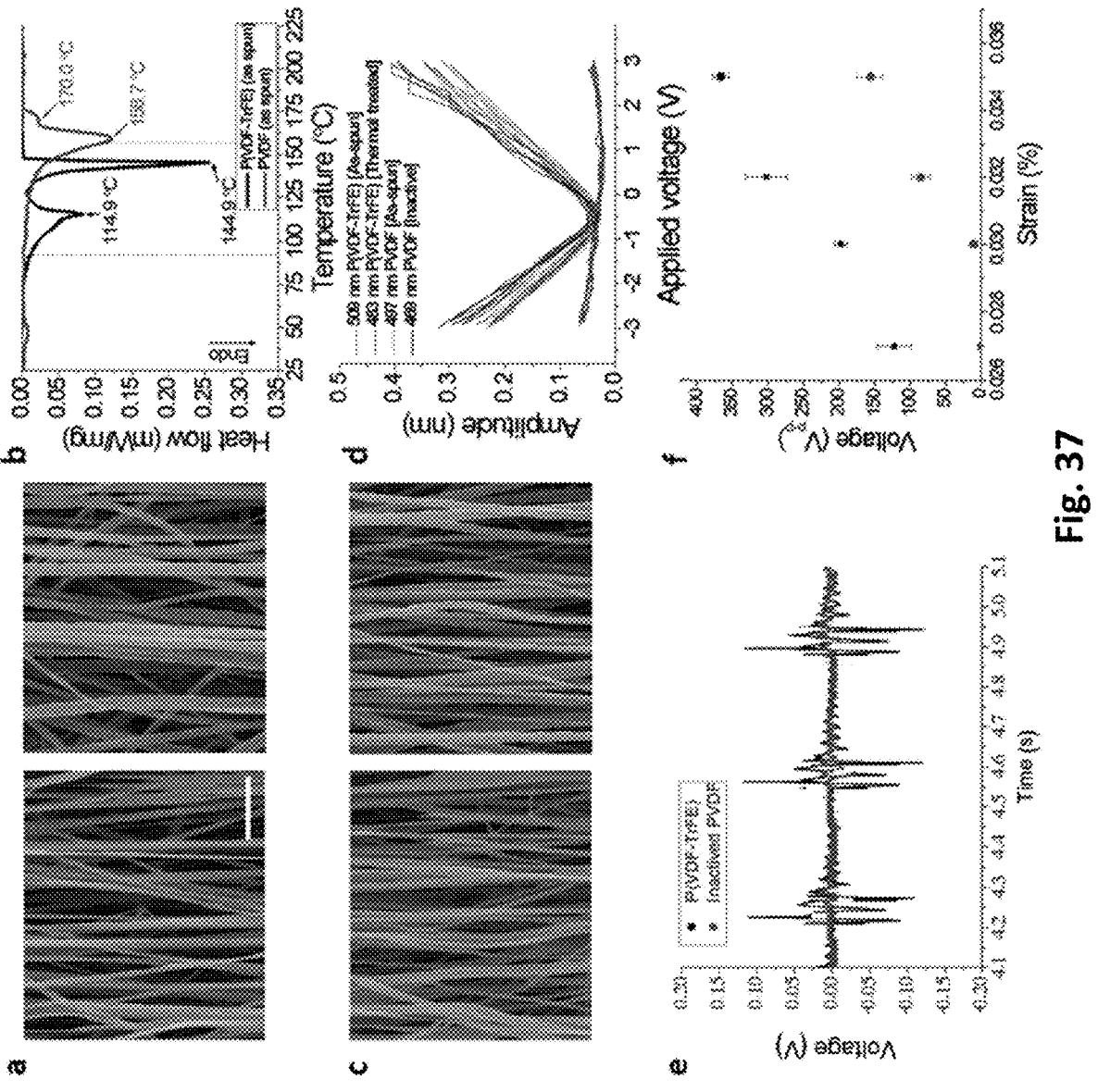

FIG. 37. (a) PVDF scaffolds. (b) To enhance the piezoelectricity in the P(VDF-TrFE) fibers, a thermal treatment below the Curie temperature (114.9° C.) at 90° C. was carried out to promote the slight re-arrangement of the crystalline polarized domains without causing a full transition from the ferro- to para-electric phase. (c) Thermal treatments, 90° C. for 24 hrs for P(VDF-TrFE) and 158° C. for 1 hr for PVDF, have no effect on the morphology of the nanofiber scaffolds. (d) piezo-response force microscopy (PFM). (e) The electrical characteristics of these heat-treated scaffolds were measured using the hydro-acoustic actuation system. (f) As a function of applied strain, the peak-to-peak voltage generated at the surface of the scaffolds showed a linear trend for P(VDF-TrFE).

Figure 38:
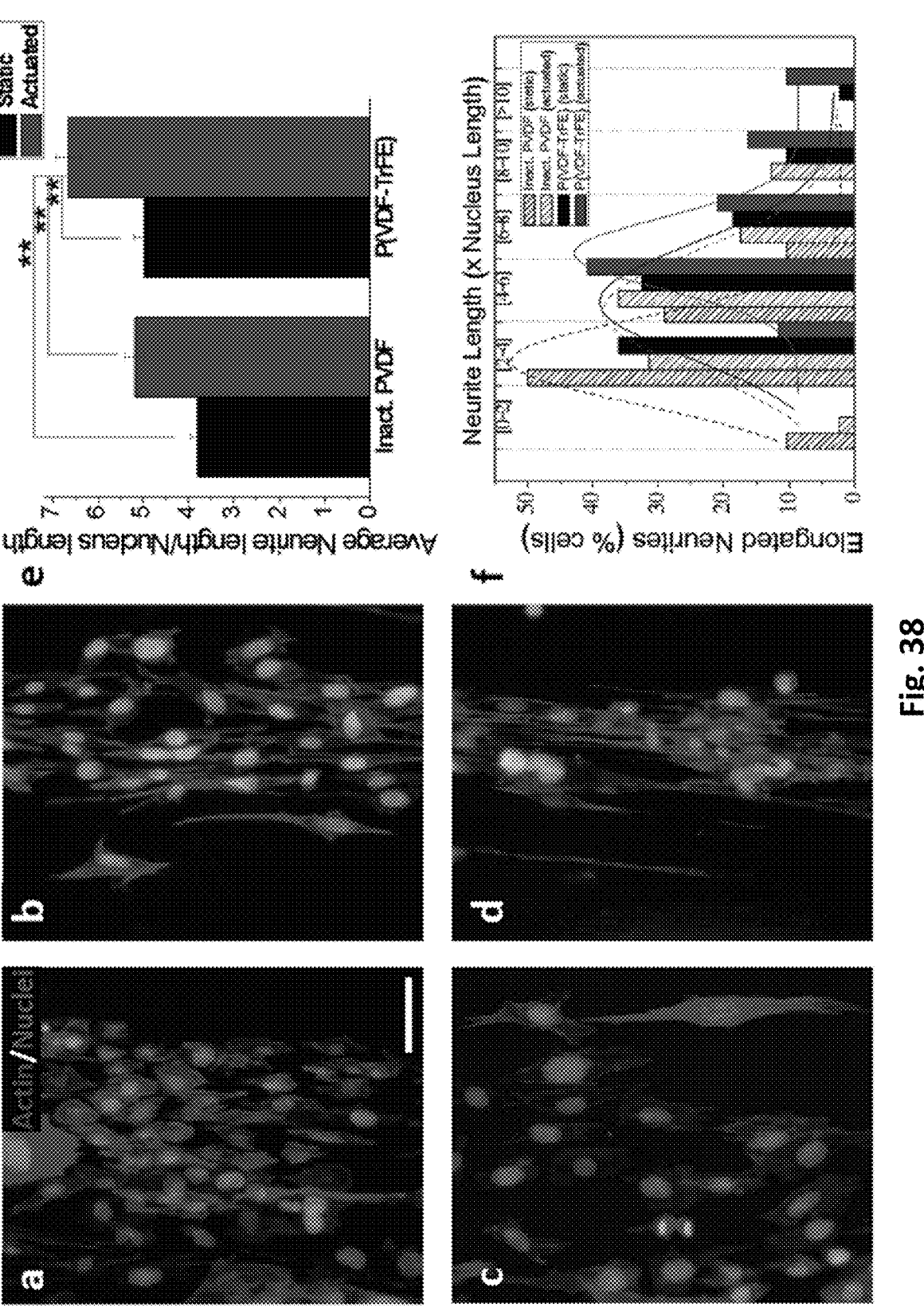

FIG. 38. (a)-(d) Immunofluorescent imaging was utilized to examine the neurite length relative to the nucleus length in each condition. (e) average neurite length/nucleus length. (f) Percentage of elongated neurites.

Figure 39:
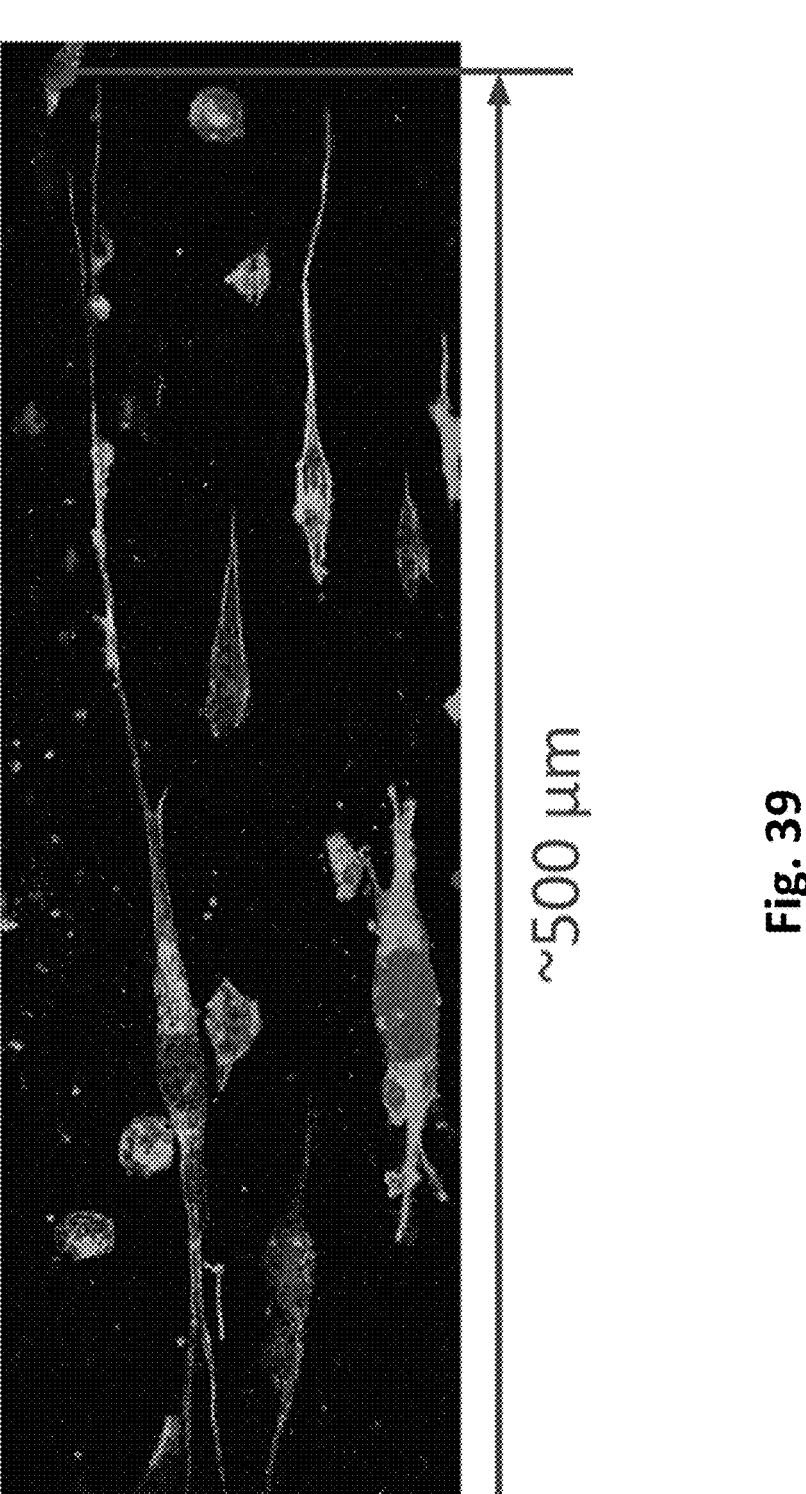

FIG. 39. Cells exposed to multi-day piezoelectric stimulation using the optimized P(VDF-TrFE) scaffolds, exhibited significantly enhanced neurite formation up to 500 μm in merely five days of stimulation and 60% of the population possessed neurites.

Figure 40:
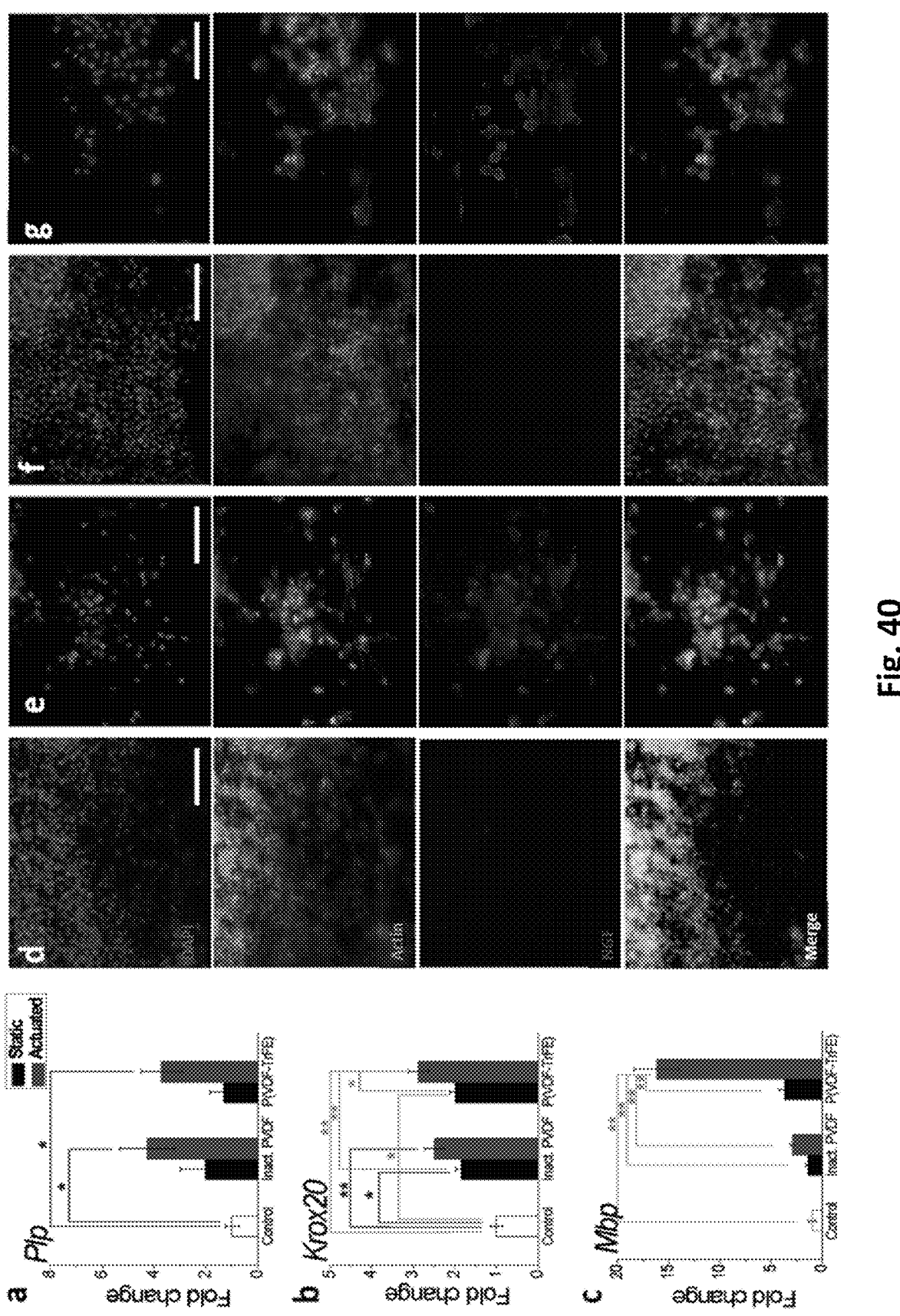

FIG. 40. (a)-(c) Gene expression of Schwann cell markers including myelin-specific proteolipid protein (Plp), early growth response protein 2 (Krox20 or Egr2), and myelin basic protein (Mbp). (d) and (f) Immunofluorescent imaging showed that the cells grew in large colonies on both scaffolds under static culture, similar to the cells cultured on tissue culture plates. (e) and (g): Actuated culture for both scaffolds induced more single cell formation.

Figure 41:
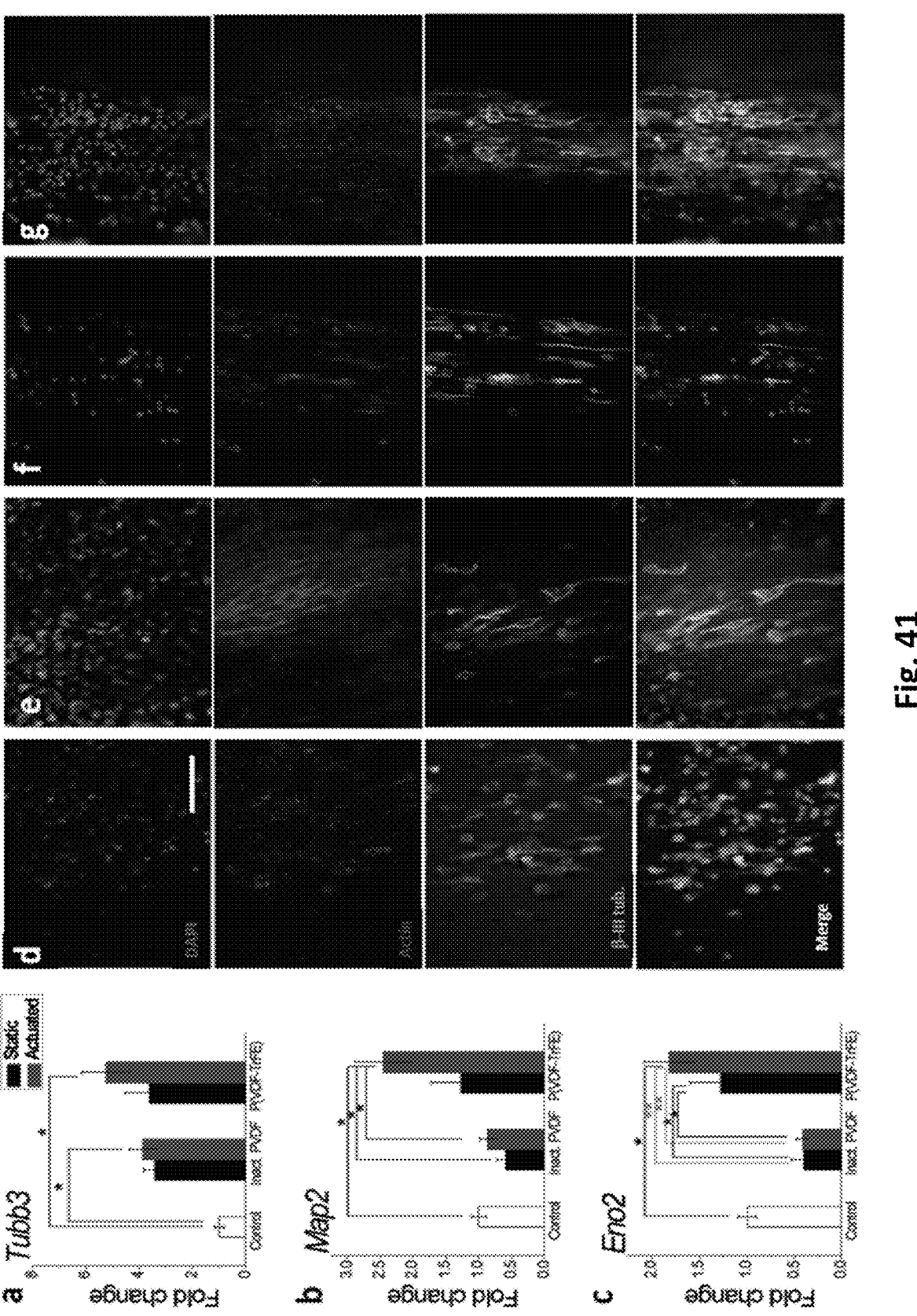

FIG. 41. (a)-(g): Mechano-electrical stimulation on the differentiation capacity of NSCs towards neuronal cells.

Figure 42:
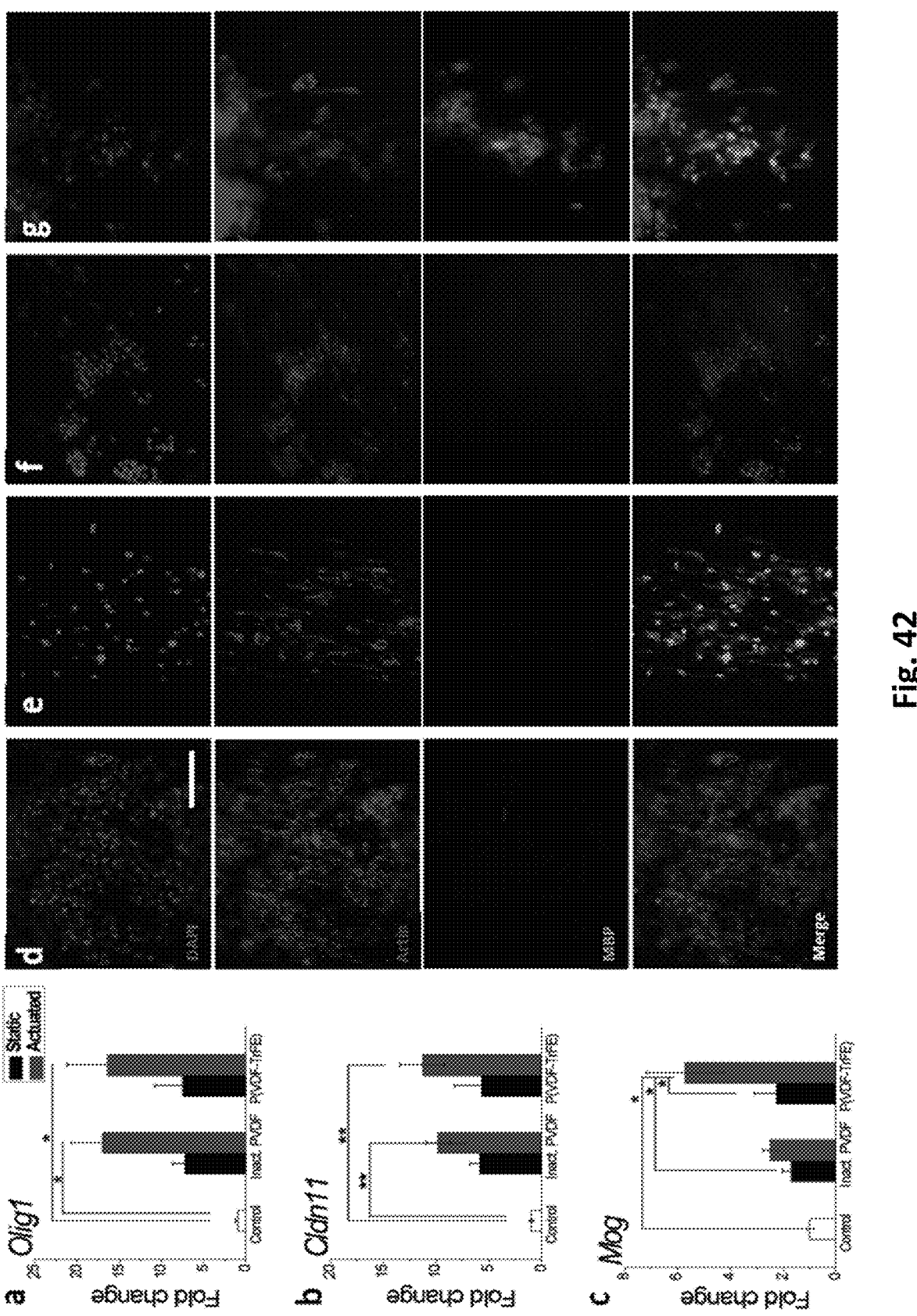

FIG. 42. (a)-(g): Mechano-electrical stimulation on the differentiation capacity of NSCs towards oligodendrocytic cells.

Figure 43:
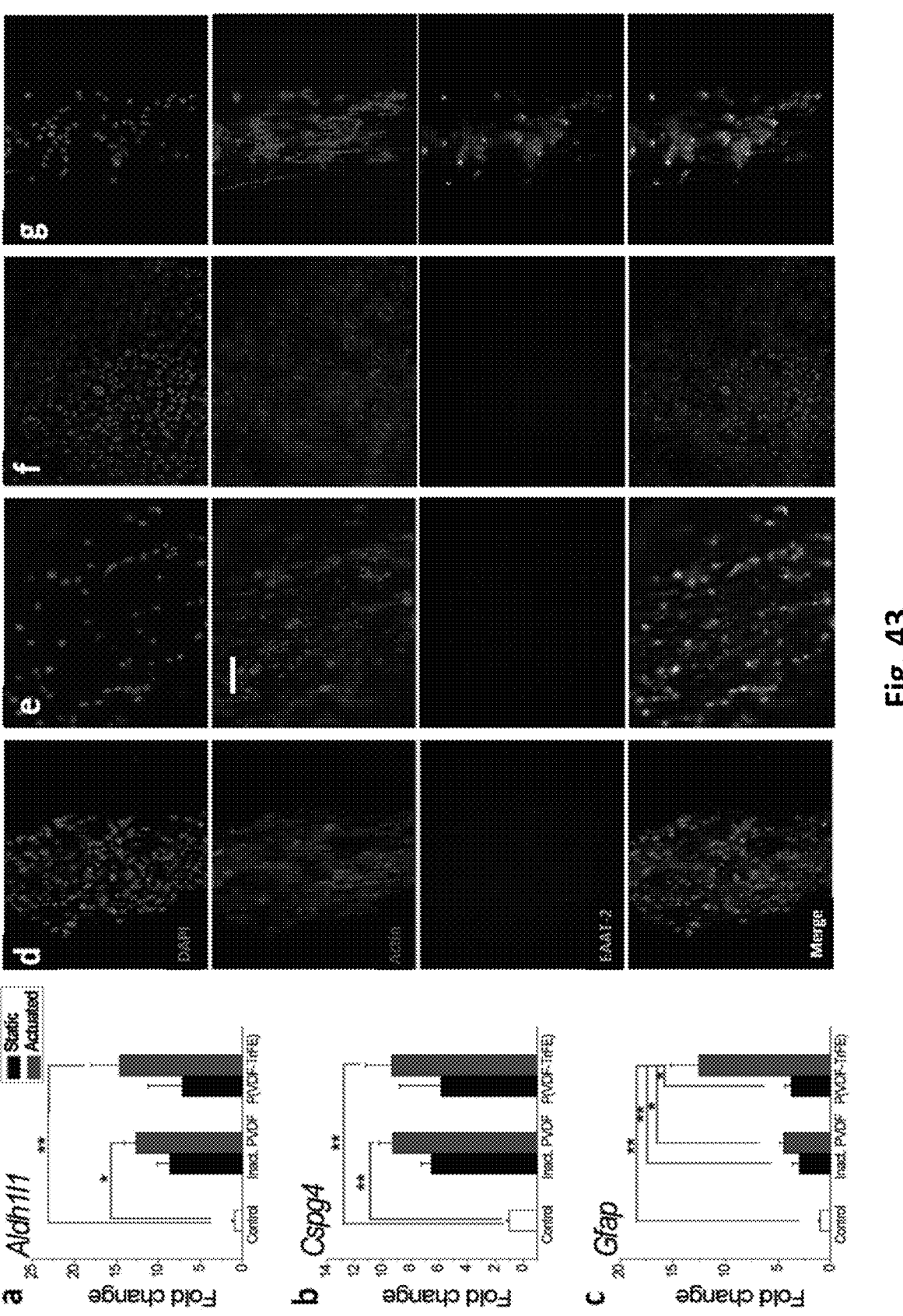

FIG. 43. (a)-(g): Mechano-electrical stimulation on the differentiation capacity of NSCs towards astrocytic cells.

Figure 44:
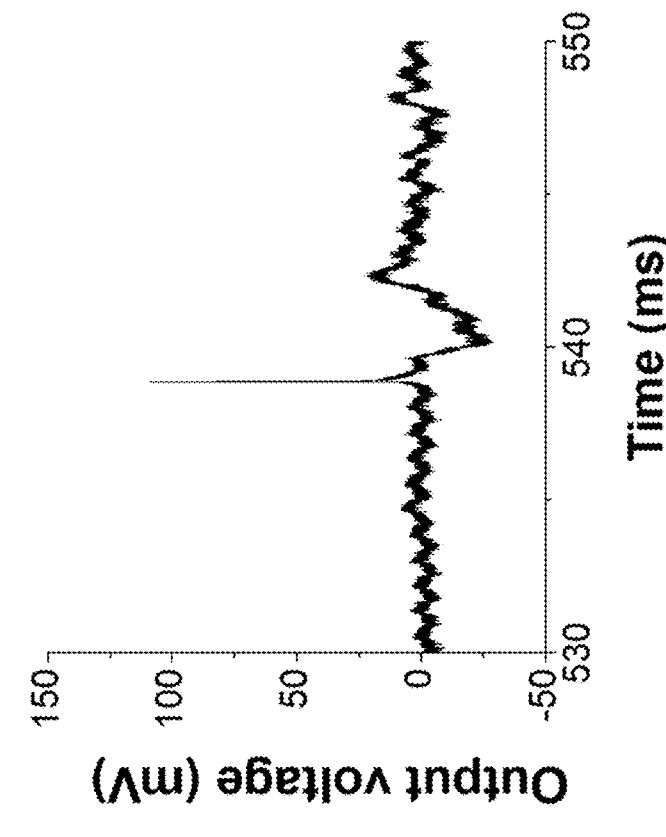
Figure 44:
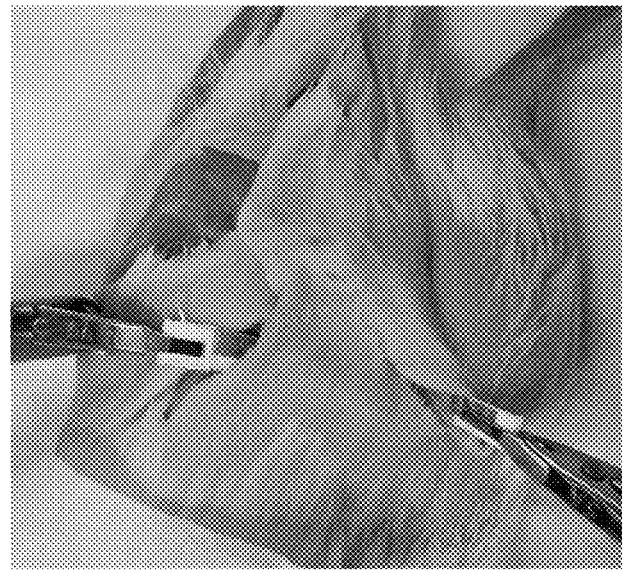

FIG. 44. Activation of piezoelectric scaffold in a deceased rat. (a) A picture showing a piezoelectric PVDF-TrFE scaffold (with electrodes connected to measure voltage outputs) embedded near a sciatic nerve in a rat. (b) A representative graph showing electric field generation of the embedded scaffold by an applied impact energy flux of 0.1 mJ/mm². This confirms the feasibility of utilizing physiologically safe impact loading to activate the piezoelectric neuroconduit.

DETAILED DESCRIPTION

Anatomy of a Nerve

The nervous system is composed of the central and peripheral nervous systems. The central nervous system (CNS) consists of the brain and spinal cord, and is responsible for integrating information and coordinating activity from the entire body. In contrast, the peripheral nervous system (PNS) refers to the nerves outside of the CNS, processing bio-directional electrical signals of the motor and sensory neurons. There are two types of neural cells found in both nervous systems: neurons and glial cells. Neurons transmit information to other nerve cells, muscles, or gland cells. Most neurons possess long axons that extend from the cell body that are either myelinated or unmyelinated.

Figure 1:
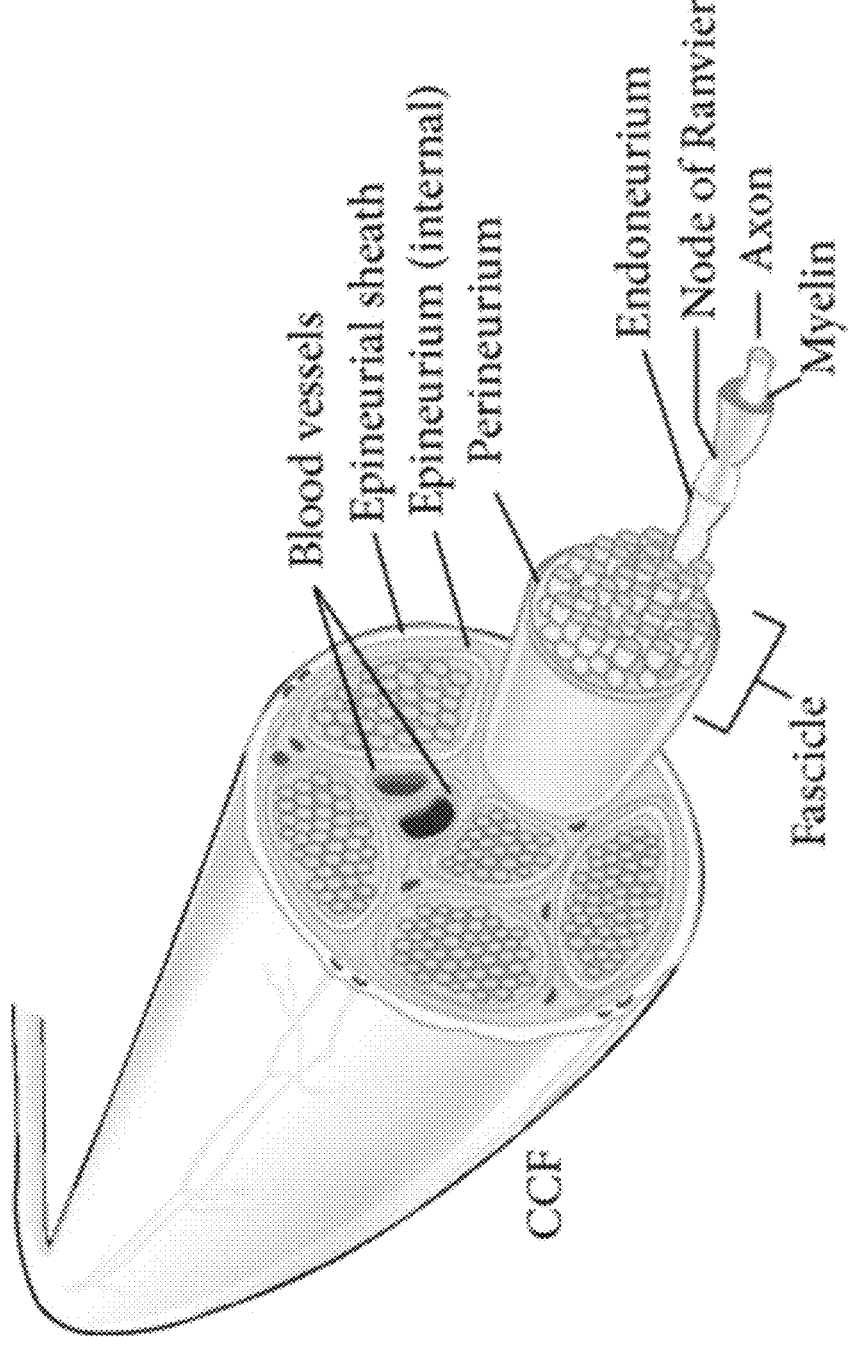
FIG. 1. Microanatomy of nerve bundle. A nerve bundle is a multi-structured tissue comprised of a bundle of myelinated or unmyelinated axons that are wrapped in connective tissue and blood vessels. (see, Siemionow, M. and G. Brzezicki, Current techniques and concepts in peripheral nerve repair. International review of neurobiology, 2009. 87: p. 141-172).

Glial cells are axillary cells that are responsible for maintaining the function of nerves. Schwann cells in the PNS and oligodendrocytes in the CNS are the glial cells that encapsulate the axon with myelin and provide neurotrophic factors. Myelin increases conduction velocity of the electrical signal along the axon by limiting ionic transfer to the nodes of Ranvier, resulting a faster action potential propagation. Astrocytes, another glial cell of the CNS, anchor neurons to their blood supply to help regulate its surroundings by removing excess ions and neurotransmitters. In addition to these cells immediately neighboring the axon, many layers of connective tissue surround the axon. The layer closest to the myelinated axon is the endoneurium, which helps contains the nutrient fluid. The perinerium surrounds bundles of endoneurium-covered axons to form fascicles. Lastly, the epinerium is the outermost connective tissue layer of the nerve. The epifascicular epinerium fills in the spaces between the fascicles, while the epineural epinerium completely surrounds the nerve trunk. Blood vessels are dispersed throughout the nerve to provide the axons with nutrients. A bundle of axons is called a nerve in the PNS and tract in the CNS (FIG. 1).

Nerve Pathophysiology

Nerve injuries are classified into five categories, ordered by the degree of damage on the overall structure of the nerve (Table 1) (Sunderland, S. and F. Walshe, Nerves and nerve injuries. 1968). The mildest form of injury, Grade I or neuropraxia, is defined as damage to the myelin sheath without any damage to the axons or the connective tissue layers. Grade II through IV, or axonotmesis, involve damage to the myelin sheath as well as the axon itself. The surrounding connective tissue layers remain intact. The grade of injury increases with the amount of damage to the endoneurium, perinerium, and epinerium. The most severe form of nerve injury, Grade V or neurotmesis, is when the nerve is completely transected. The capability of nerve regeneration depends on the degree of nerve damage.

TABLE 1

| Seddon's classification | Sunderland's classification | Tissues Injured |
| --- | --- | --- |
| Neurapraxia | Grade I | Myelin |
| Axonotmesis | Grade II | Myelin, axon |
| Axonotmesis | Grade III | Myelin, axon, endoneurium |
| Axonotmesis | Grade IV | Myelin, axon, endoneurium, perineurium |
| Neurotmesis | Grade V | Myelin, axon, endoneurium, perineurium, epineurium |

Peripheral Nervous System

Figure 2:
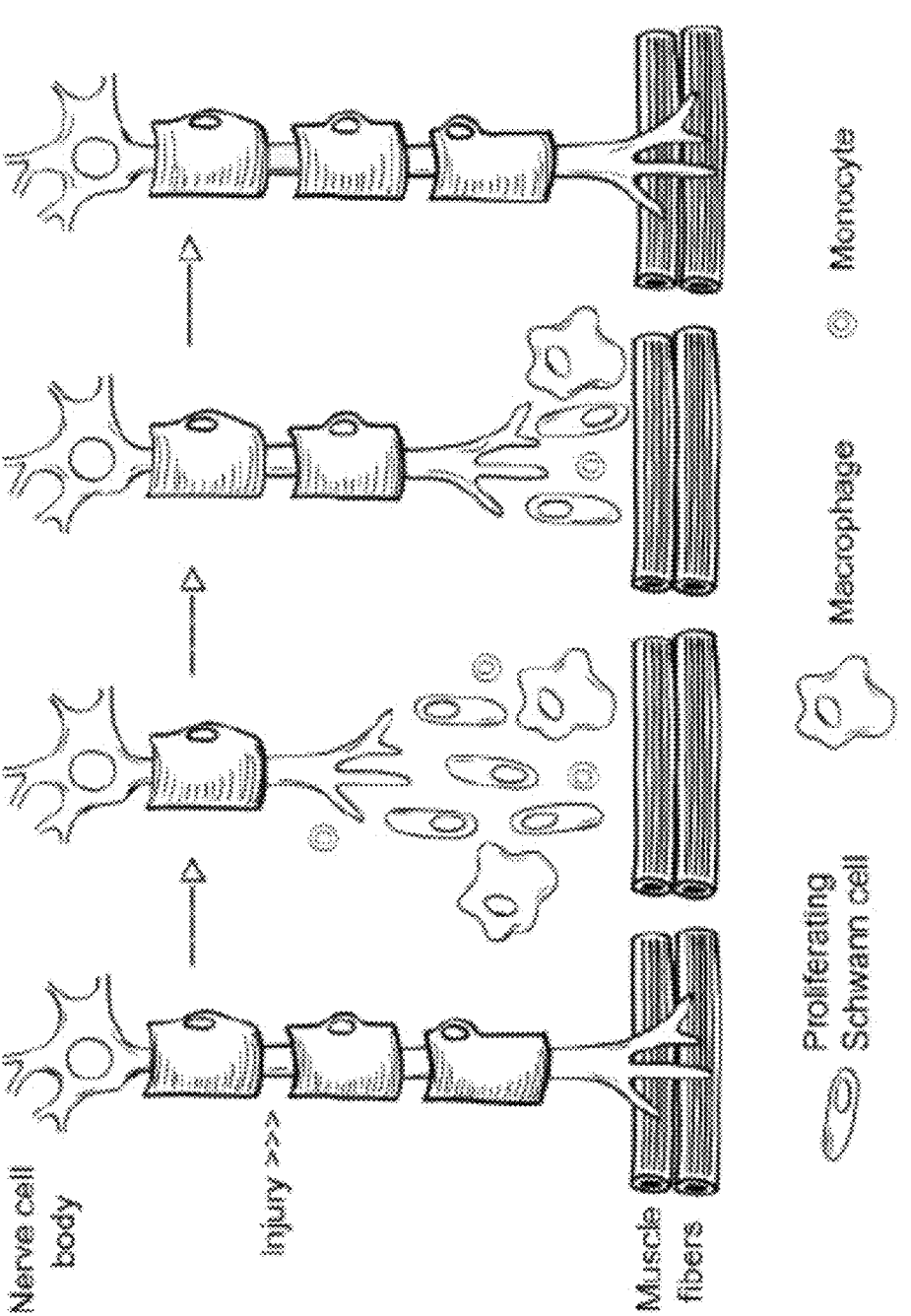
FIG. 2. Process following nerve injury in the peripheral nervous system. When a peripheral nerve is injured, compressed or transected, Wallerian degeneration begins to remove old nerve from injury site to target muscle/organ leaving behind a connective tissue tube. Once the old nerve is degenerated, peripheral nerve regeneration begins to a certain capacity. (see, Ba, M. and F. Bonhoeffer, Perspectives on axonal regeneration in the mammalian CNS. Trends in neurosciences, 1994. 17(11): p. 473-479).

The PNS has a much greater capacity for nerve self-regeneration than the central nervous system (FIG. 2). When a traumatic injury to the axon of a PNS neuron occurs, either compressed or transected, initially, a retrograde signal is sent to the nucleus by importin, an early injury responsive protein. Importins form a complex with dynein, a cytoskeletal motor protein responsible for driving retrograde axonal transport, on the axon and sends a cocktail of transcription factors associated with regeneration, such as c-Jun, Oct6, Sox11, and p53, to determine the fate of the injured neuron (Patodia, S. and G. Raivich, Role of Transcription Factors in Peripheral Nerve Regeneration. Frontiers in Molecular Neuroscience, 2012. 5: p. 8).

When these signaling cascades are initiated, the distal end of the injured axon undergoes molecular changes to create an environment for axon regeneration. The process, known as Wallerian degeneration, that begins in the axon on the distal end of the injured nerve completely degenerates the axon by removing and recycling axonal and myelin-derived components towards the target tissue. Existing Schwann cells clear the axonal and myelin debris, leaving behind an empty endoneurial tube. Macrophages are recruited to the injury site, releasing growth factors to induce the proliferation of Schwann cells and fibroblasts. The proliferating Schwann cells line the inner surface of the empty endoneurial tube, which form the bands of Bungner, to direct the regenerating axon through the distal nerve stump towards the target tissue. On the proximal end of the injury site, the axon degenerates up to the adjacent node of Ranvier, where subsequent axon regrowth begins. These series of events play an important role in creating a supportive environment for successful axon regeneration.

Once the debris is cleared from the distal nerve stump, a cascade of cellular events occur to regenerate the axon from the adjacent node of Ranvier of the proximal nerve stump into the distal segment. About 50-100 nodal sprouts develop from the node of Ranvier into a growth cone. Neurotrophic factors from the target tissue and denervated motor and sensory receptors signal the growth cone to elongate. From the growth cone, many axon extensions elongate until they connect with a receptor. If a receptor or the endoneurial tube is not reached, the growth cone continues to elongate in a disorganized manner forming a neuroma. The more severe the injury is, the more disorder occurs, therefore less effective axon regeneration. Therefore, there is a need for tissue engineering strategies to aid in the elongation process by environmental, cellular, and biochemical factors.

Central Nervous System

Figure 3:
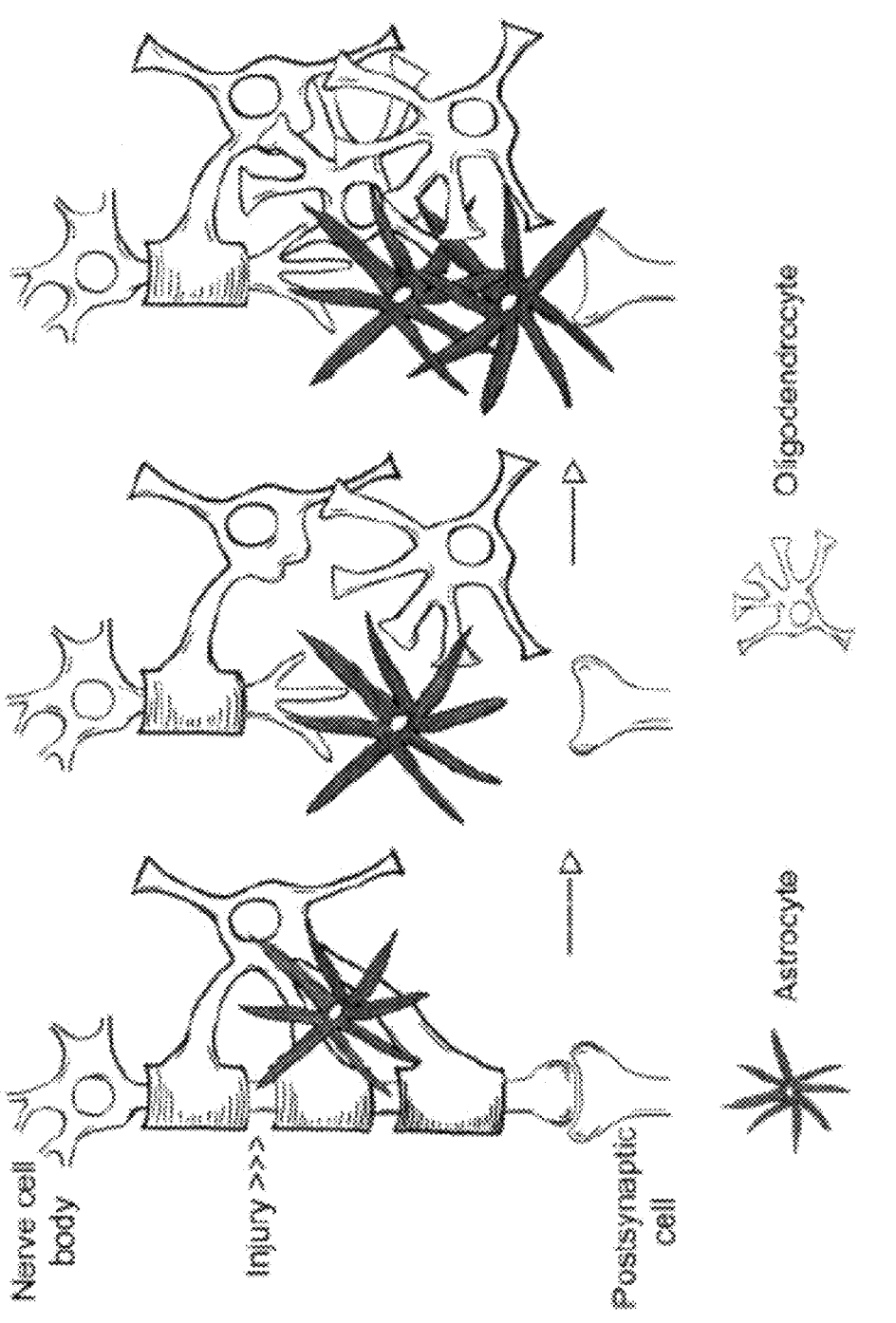
FIG. 3. Process following nerve injury in the central nervous system. Natively, the central nervous system has a limited capacity of nerve regeneration. When a central nerve is injured, glial cells infiltrate the injury site to begin repair, forming scar tissue. (see, Ba, M. and F. Bonhoeffer, Perspectives on axonal regeneration in the mammalian CNS. Trends in neurosciences, 1994. 17(11): p. 473-479).

When the brain or spinal cord is injured, complex cellular and molecular interactions occur in attempt to repair the damaged tissue (FIG. 3). Unlike the PNS neurons, CNS neurons have not been shown to possess the innate ability to regenerate the axon of a damaged nerve. It was shown that the CNS lacks the permissive environment for proper axonal regeneration (Ramon y Cafal, S., Degeneration and Regeneration of the Nervous System, R M May, ed. and transl. Hafner, New York, 1928). However, several studies found that CNS axons are capable of small amounts of regeneration, short distance neurite growth within the lesion site under certain conditions (Davies, S. J., et al., Regeneration of adult axons in white matter tracts of the central nervous system. Nature, 1997. 390(6661): p. 680; David, S. and A. J. Aguayo, Axonal elongation into peripheral nervous system "bridges" after central nervous system injury in adult rats. Science, 1981. 214(4523): p. 931-933; and Richardson, P., U. McGuinness, and A. Aguayo, Axons from CNS neurones regenerate into PNS grafts. Nature, 1980. 284 (5753): p. 264-265). The main factors responsible for intrinsically limiting CNS axon regeneration have been believed to be inhibitors found within myelin and the formation of glial scars.

Myelin-associated inhibitors (MIAs) are secreted by oligodendryocytes. Three types of MIAs have been identified, Nogo, myelin-associated glycoprotein (MAG), and oligodendrocyte myelin glycoprotein (OMG) (Cadelli, D., C. Bandtlow, and M. Schwab, Oligodendrocyte- and myelin-associated inhibitors of neurite outgrowth: their involvement in the lack of CNS regeneration. Experimental neurology, 1992. 115(1): p. 189-192). Nogo, found on the surface of oligodendrocytes and the innermost surface of the myelin membrane in contact with the axon, induces the collapse of the axon growth cone. On the other hand, MAG, found in the periaxonal membrane which is in contact with axonal receptors, inhibits neurite elongation of mature neurons. Lastly, OMG, found next to the Node of Ranvier, inhibits neurite elongation as well as induces growth cone collapse.

Glial scars are formed by astrocytes when the CNS is injured. The scar creates a physical barrier to prevent axon regeneration from occurring. Also, the molecular composition of the glial scar and the synthesis of inhibitory molecules, such as certain chondroitin sulfate proteoglycans (CSPGs) and cytotactin/tenascin (CT), contribute to regeneration failure (Fitch, M. T. and J. Silver, CNS injury, glial scars, and inflammation: Inhibitory extracellular matrices and regeneration failure. Experimental neurology, 2008. 209(2): p. 294-301; and Fawcett, J. W. and R. A. Asher, The glial scar and central nervous system repair. Brain research bulletin, 1999. 49(6): p. 377-391). The upregulation of CSPGs near glial scars has been associated with the creation of non-permissive neurite growth environment in the CNS (Sofroniew, M. V., Molecular dissection of reactive astrogliosis and glial scar formation. Trends in neurosciences, 2009. 32(12): p. 638-647). Therefore, strategies to reduce inhibitory factors and promote permissive factors will help overcome the limitation of nerve regeneration of the CNS.

Functional Restoration of Nerve

Peripheral Nervous System

Despite advancement of surgical technologies, complete functional recovery following nerve damages is rarely achieved due to the poor or absent inherent neural regenerative capabilities of the peripheral nervous system. Damages can be caused by traumatic injuries, infectious diseases, degeneration, autoimmune disorders, and tumors. The functional success of surgical nerve repair following a nerve injury is determined by the degree of injury, the type of repair performed on the damage nerve, delay before surgical intervention, and patient's age. Understanding how these factors affect the result of nerve regeneration can be beneficial for designing and optimizing tools to enhance recovery for both PNS and CNS. For regeneration to occur, it is a prerequisite for the proximal end of the axons must be able to regrow, the distal site of the injury must be able to support regrowth, and for the target tissue to accept new axons. Different biomaterial and cellular approaches have been attempted to achieve such requirements to enhance nerve regeneration.

Nerve Grafts

In the case of nerve gaps greater than 30 mm, the current gold standard to repair transected nerves is autologous nerve grafting. This method provides the structural support to guide axon regeneration, preventing the formation of neuromas (Millesi, H., Bridging defects: autologous nerve grafts. How to improve the results of peripheral nerve surgery, 2007: p. 37-38). Because it is surgically removed from the patient's own body, the autograft, most commonly taken from the sural nerve of the calf region, acts as an immunogenically inert scaffold, providing viable Schwann cells and appropriate neurotrophic factors for axon regeneration (Dahlin, L. and G. Lundborg, Use of tubes in peripheral nerve repair. Neurosurgery Clinics of North America, 2001. 12(2): p. 341-352). However, this technique possesses many limitations, including the necessity of multiple surgeries, the induction of functionally impaired region where graft was taken from, and disproportion of graft to nerve tissue in size and structure. Furthermore, the patient is at high risk of a neuroma formation in the transplanted area. Alternative clinical options include cadaver allografts (Grand, A. G., et al., Axonal regeneration after cold preservation of nerve allografts and immunosuppression with tacrolimus in mice. Journal of neurosurgery, 2002. 96(5): p. 924-932; Mackinnon, S. E., et al., Clinical outcome following nerve allograft transplantation. Plastic and reconstructive surgery, 2001. 107(6): p. 1419-1429; and Kim, B. S., J. J. Yoo, and A. Atala, Peripheral nerve regeneration using acellular nerve grafts. Journal of biomedical materials research Part A, 2004. 68(2): p. 201-209), veins and arteries as grafts (Battiston, B., et al., Nerve repair by means of tubulization: literature review and personal clinical experience comparing biological and synthetic conduits for sensory nerve repair. Microsurgery, 2005. 25(4): p. 258-267), and natural/synthetic conduits, but each of these possess their own disadvantages. When using allografts, patients risk a systemic immunoresponse and is not suitable for nerve gaps greater than 30 mm (Udina, E., E. Verdn, and X. Navarro, Effects of the immunophilin ligand FK506 on nerve regeneration in collagen guides seeded with Schwann cells in rats. Neuroscience letters, 2004. 357(2): p. 99-102); vein and artery grafts also cannot bridge nerve gaps greater than 30 mm (Karabekmez, F. E., A. Duymaz, and S. L. Moran, Early clinical outcomes with the use of decellularized nerve allograft for repair of sensory defects within the hand, 2009, SAGE Publications Sage CA: Los Angeles, CA); and lastly, current clinically-approved natural and synthetic conduits are have not been able to fully repair transected nerves with nerve gaps greater than 30 mm to regain full functionality (Kehoe, S., X. F. Zhang, and D. Boyd, FDA approved guidance conduits and wraps for peripheral nerve injury: A review of materials and efficacy. Injury, 2012. 43(5): p. 553-572). To address these limitations, tissue engineering strategies seek to develop nerve guidance conduits to address these limitations.

Nerve Guidance Conduits

When selecting a biomaterial for developing a neuroconduit, the physicochemical, biomechanical, and biological properties must be considered. The material should possess the proper permeability and porosity for nutrition and ion transport. The mechanical properties, such as stiffness and elasticity, should match the native tissue for better integration with surrounding tissue. Lastly, it should be biocompatible and possess the proper surface chemistry.

Natural Conduits

Natural biomaterials for neuroconduits are typically either: (1) autologous non-neural tissues and decellularized allogenic/xenogenic neural/non-neural tissues or (2) naturally-derived polymers including ECM proteins (collagen, laminin, hyaluraonan) and polysaccharides (agarose, chitosan). Avance® offers commercially available human decellularized nerve allografts. Studies showed that Avance® improved nerve functional recovery of sensory, motor, and mixed nerves with nerve gaps up to 30 mm (Neubauer, D., J. B. Graham, and D. Muir, Chondroitinase treatment increases the effective length of acellular nerve grafts. Experimental neurology, 2007. 207(1): p. 163-170; and Whitlock, E. L., et al., Processed allografts and type I collagen conduits for repair of peripheral nerve gaps. Muscle & Nerve, 2009. 39(6): p. 787-799). However, the use of the allografts requires additional administration of immunosuppressants for 18 months as well as it is limited in the gap length. Naturally-derived polymeric neuroconduits are immunologically inert. There are several of these neuroconduits that have been FDA approved and are commercially available to use in the clinical setting. NeuroGen®, a commercially available conduit made of collagen type I, showed improved sensory scores for a variety of nerves, but was limited to nerve gaps of an average 13 mm (Whitlock, E. L., et al., Processed allografts and type I collagen conduits for repair of peripheral nerve gaps. Muscle & Nerve, 2009. 39(6): p. 787-799). The common limitation of the wide variety of tested materials is that none have shown reliable success for nerve gaps greater than 30 mm.

Synthetic Conduits

Silicone neuroconduits were the first to demonstrate the feasibility of synthetic materials for nerve repair by bridging nerve defects up to 15 mm (Merle, M., et al., Complications from silicon-polymer intubulation of nerves. Microsurgery, 1989. 10(2): p. 130-133). However, due to its immunogenic non-permeable properties, the implanted conduit induced permanent fibrotic tissue formation ultimately leading to nerve compression. This led to the development of absorbable synthetic conduits. Biodegradable synthetic biomaterials, including polyglycolic acid (PGA) and poly(D,L-lactide-co-F-caprolactone) (PCL), have been investigated as a scaffolding material for nerve regeneration. PGA, an FDA-approved biomaterial, has been shown have 86% meaningful recovery of nerve defects less than 30 mm (Mackinnon, S. E. and A. L. Dellon, Clinical nerve reconstruction with a bioabsorbable polyglycolic acid tube. Plastic and reconstructive surgery, 1990. 85(3): p. 419-424). However, PGA rapidly degrades to lactic acid in 90 days, possibly before the completion of nerve regeneration (de Tayrac, R., et al., Long-lasting bioresorbable poly (lactic acid)(PLA94) mesh: a new approach for soft tissue reinforcement based on an experimental pilot study. International Urogynecology Journal, 2007. 18(9): p. 1007-1014). PCL, another FDA-approved biomaterial, produces less acidic degradation byproducts (Sun, H., et al., The in vivo degradation, absorption and excretion of PCL-based implant. Biomaterials, 2006. 27(9): p. 1735-1740). However, it has reported only a 25% meaningful recovery of nerve defects up to 20 mm (Chiriac, S., et al., Experience of using the bioresorbable copolyester poly (DL-lactide-F-caprolactone) nerve conduit guide Neurolac™ for nerve repair in peripheral nerve defects: report on a series of 28 lesions. Journal of Hand Surgery (European Volume), 2012. 37(4): p. 342-349). NEUROTUBE®, made of PGA, and NEUROLAC®, made of poly(D,L-lactide-co-F-caprolactone) are neuroconduits that are FDA-approved and commercially available.

The issue with large nerve gaps is limited by the rate of axonal elongation. Native Schwann cells eventually advance ahead of the regenerating axons, no longer providing a sufficient environment for axon growth (Son, Y.-J., J. T. Trachtenberg, and W. J. Thompson, Schwann cells induce and guide sprouting and reinnervation of neuromuscular junctions. Trends in neurosciences, 1996. 19(7): p. 280-285). Another issue with large nerve gaps is that the disorganization of axon extensions from the growth cone continues to increase as the length of the nerve gap increases (Menorca, R. M., T. S. Fussell, and J. C. Elfar, Peripheral nerve trauma: mechanisms of injury and recovery. Hand clinics, 2013. 29(3): p. 317; and Ertürk, A., et al., Disorganized microtubules underlie the formation of retraction bulbs and the failure of axonal regeneration. Journal of Neuroscience, 2007. 27(34): p. 9169-9180). To enhance the outcome of peripheral nerve regeneration through the use of neuroconduits alone, efforts have focused on the incorporation of biochemical cues, such as supportive cells, growth factors and electrical input in order to provide a supportive environment for successful axon regeneration.

Cell-Based Therapy

A method to accelerate axon regeneration and bridging large nerve gaps is the addition of supportive cells to nerve injury site. The cell types currently researched include primary cells, such as Schwann cells and olfactory ensheathing cells (OECs), and stem cells, such as embryonic stem cells (ESCs), induced pluripotent stem cells (iPSCs), neural stem cells (NSCs), and mesenchymal stem cells (MSCs). Cell-based therapy has the potential to create a supportive environment by secretion of axon-promoting factors from these cells for peripheral nerve regeneration. Schwann cells play an important role in peripheral nerve regeneration, therefore they have been an ideal candidate as transplantable supportive cells. They produce many neurotrophic factors, such as nerve growth factor (NGF), brain-derived neurotrophic factor (BDNF), and plate-derived growth factor (PDGF), to promote the regeneration and enhance the survival of damaged axons (Frostick, S. P., Q. Yin, and G. J. Kemp, Schwann cells, neurotrophic factors, and peripheral nerve regeneration. Microsurgery, 1998. 18(7): p. 397-405; Menei, P., et al., Schwann cells genetically modified to secrete human BDNF promote enhanced axonal regrowth across transected adult rat spinal cord. European Journal of Neuroscience, 1998. 10(2): p. 607-621; Assouline, J. G., et al., Rat astrocytes and Schwann cells in culture synthesize nerve growth factor-like neurite-promoting factors. Developmental Brain Research, 1987. 31(1): p. 103-118; and Jessen, K., et al., The Schwann cell precursor and its fate: a study of cell death and differentiation during gliogenesis in rat embryonic nerves. Neuron, 1994. 12(3): p. 509-527). Experimentally, transplanted Schwann cells seeded in neuroconduits have been shown to enhance axon regeneration in vivo (Hadlock, T., et al., A polymer foam conduit seeded with Schwann cells promotes guided peripheral nerve regeneration. Tissue engineering, 2000. 6(2): p. 119-127; Keilhoff, G., et al., In vivo predegeneration of peripheral nerves: an effective technique to obtain activated Schwann cells for nerve conduits. Journal of neuroscience methods, 1999. 89(1): p. 17-24; and Evans, G. R., et al., Bioactive poly (L-lactic acid) conduits seeded with Schwann cells for peripheral nerve regeneration. Biomaterials, 2002. 23(3): p. 841-848).

Another source of glia cells, OECs, can synthesize neurotrophic factors. Under normal conditions, OECs can be found in both PNS and CNS. They can provide the neurotrophic support to regenerate nerves and contribute to the myelination process (Li, Y., P. M. Field, and G. Raisman, Repair of adult rat corticospinal tract by transplants of olfactory ensheathing cells. Science, 1997. 277(5334): p. 2000-2002; Li, Y., P. M. Field, and G. Raisman, Regeneration of adult rat corticospinal axons induced by transplanted olfactory ensheathing cells. Journal of Neuroscience, 1998. 18(24): p. 10514-10524; and Dombrowski, M. A., et al., Myelination and nodal formation of regenerated peripheral nerve fibers following transplantation of acutely prepared olfactory ensheathing cells. Brain research, 2006. 1125(1): p. 1-8). However, to obtain Schwann cells or OECs, a functional nerve must be sacrificed and both have limited expansion capabilities. Therefore, stem cells provide an alternative cell source with promising potential for the development of cell-based therapy for nerve regeneration.

ESCs and iPSCs have the potential to differentiate into derivatives of all three embryonic germ layers. They can provide an unlimited source of cells with long-term proliferation capacity and superior differentiation potential. ESCs have demonstrated the ability to differentiate into neural crest cells (Lee, G., et al., Isolation and directed differentiation of neural crest stem cells derived from human embryonic stem cells. Nature biotechnology, 2007. 25(12): p. 1468), which then can further transform into neurons (Okabe, S., et al., Development of neuronal precursor cells and functional postmitotic neurons from embryonic stem cells in vitro. Mechanisms of development, 1996. 59(1): p. 89-102) and Schwann cells (Joseph, N. M., et al., Neural crest stem cells undergo multilineage differentiation in developing peripheral nerves to generate endoneurial fibroblasts in addition to Schwann cells. Development, 2004. 131(22): p. 5599-5612) amongst other mesodermal and ectodermal lineage phenotypes (Tada, S., et al., Characterization of mesendoderm: a diverging point of the definitive endoderm and mesoderm in embryonic stem cell differentiation culture. Development, 2005. 132(19): p. 4363-4374; and D'Amour, K. A., et al., Efficient differentiation of human embryonic stem cells to definitive endoderm. Nature biotechnology, 2005. 23(12): p. 1534). However, ESCs can induce an immune response, have the potential of teratoma formation, and ethical issues of ESCs harvested during the blastocyst stage of embryos. iPSCs derived from somatic cells present an alternative cell source for patient-specific therapy, eliminating limitations of ESCs. Established protocols have been developed for iPSC differentiation towards neural lineages (Karumbayaram, S., et al., Directed Differentiation of Human-Induced Pluripotent Stem Cells Generates Active Motor Neurons. Stem cells, 2009. 27(4): p. 806-811; Dimos, J. T., et al., Induced pluripotent stem cells generated from patients with ALS can be differentiated into motor neurons. Science, 2008. 321(5893): p. 1218-1221; and Hu, B.-Y., et al., Neural differentiation of human induced pluripotent stem cells follows developmental principles but with variable potency. Proceedings of the National Academy of Sciences, 2010. 107(9): p. 4335-4340). However, similar to ESCs, efficient differentiation to end-type cell phenotypes remain challenging, limiting their clinical translatability.

NSCs, derived from the brain, can directly differentiate towards neuronal and glial phenotypes and have been studied for both peripheral and central nerve regeneration (Clarke, D. L., et al., Generalized potential of adult neural stem cells. Science, 2000. 288(5471): p. 1660-1663). A study determined the efficacy and mechanism of NSCs on sciatic nerve injury in rats (Xu, L., et al., Neural stem cells enhance nerve regeneration after sciatic nerve injury in rats. Molecular neurobiology, 2012. 46(2): p. 265-274). A silicon conduit filled with NSCs bridged a 10 mm nerve gap and observed that NSCs increased the expression of neurotrophic factors, NGF and HGF, of the sciatic nerve. Therefore, it was evident that NSCs have the potential to foster a supportive environment for nerve regeneration. In another study, NSCs implanted into a transected tibial nerve were able to restore function in a denervated rat muscle (Lin, S., et al., Optimal time-point for neural stem cell transplantation to delay denervated skeletal muscle atrophy. Muscle & Nerve, 2013. 47(2): p. 194-201). Within the transected area, NSC differentiated into neuron-like cells with positive expression of βIII tubulin and glial-like cells with positive expression of GFAP. Native Schwann cells secreted various neurotrophic factors that aided in the differentiation and survival of NSCs.

In contrast to ESCs and NSCs, MSCs derived from bone marrow and adipose tissue provide an easy access and autologous source to stem cells for transplantation therapies. Bone-marrow derived MSCs (BMSCs) and adipose-derived MSCs (ADSCs) can differentiate into neurons, astrocytes, and Schwann cell-like cells (Ahmadi, N., et al., Stability of neural differentiation in human adipose derived stem cells by two induction protocols. Tissue and Cell, 2012. 44(2): p. 87-94; Ning, H., et al., Neuron-like differentiation of adipose tissue-derived stromal cells and vascular smooth muscle cells. Differentiation, 2006. 74(9-10): p. 510-518; and Zhang, H.-T., et al., Neural differentiation ability of mesenchymal stromal cells from bone marrow and adipose tissue: a comparative study. Cytotherapy, 2012. 14(10): p. 1203-1214). Both BMSCs and ADSCs have shown enhanced axon regeneration and myelination capability when transplanted in cell-seeded scaffolds (Wang, J., et al., Bone marrow mesenchymal stem cells promote cell proliferation and neurotrophic function of Schwann cells in vitro and in vivo. Brain research, 2009. 1262: p. 7-15; Wang, Y., et al., Recellularized nerve allografts with differentiated mesenchymal stem cells promote peripheral nerve regeneration. Neuroscience letters, 2012. 514(1): p. 96-101; and Sun, F., et al., Combined use of decellularized allogeneic artery conduits with autologous transdifferentiated adipose-derived stem cells for facial nerve regeneration in rats. Biomaterials, 2011. 32(32): p. 8118-8128). When directly comparing the performance between BMSCs and ADSCs, there were no significant differences in performance. Low morbidity of harvest site, easy accessibility and wide availability, and superior stem cell characteristics have made ADSCs the preferred option for pre-clinical studies.

Central Nervous System

As compared to the PNS, the CNS has a much more limited capacity to self-regeneration. Therefore traumatic injuries and diseases are very debilitating to the patient, often leading to loss of motor, sensory, and cognitive functions, especially for injuries occurring in the C4 or C5 of the cervical spinal cord (Michael, J., J. S. Krause, and D. P. Lammertse, Recent trends in mortality and causes of death among persons with spinal cord injury. Archives of physical medicine and rehabilitation, 1999. 80(11): p. 1411-1419). The inability of neurons to regenerate after an injury is due to the inhibitive microenvironment created by the presence of inhibitory factors and lack of axon-growth promoting factors (Dumont, R. J., et al., Acute spinal cord injury, part I: pathophysiologic mechanisms. Clinical neuropharmacology, 2001. 24(5): p. 254-264). Currently there are no cures for injuries in the CNS, there are only a few treatment options to delay the progression of CNS diseases. Two main strategies for CNS treatment include: neuroprotection and neuroregeneration. Neuroprotection refers to the inhibition of the death of CNS neural cells. Neuroregeneration refers to the regeneration of severed axons and sprouting of existing axons to reinnervate denervated target muscle/organ.

Pharmacological Treatments

It is advantageous to immediately begin treatment at the onset of a traumatic injury to prevent complete neurological death. Specifically for spinal cord injury, after the patient is immobilized to prevent further neural damage, methylprednisolone, a glucocorticoid, can be administered within 8 hours of injury to reduce damage to nerve cells and decrease inflammation (Bracken, M. B., et al., Administration of methylprednisolone for 24 or 48 hours or tirilazad mesylate for 48 hours in the treatment of acute spinal cord injury: results of the Third National Acute Spinal Cord Injury Randomized Controlled Trial. Jama, 1997. 277(20): p. 1597-1604). Currently, methylprednisolone is the only approved pharmacotherapy for spinal cord injury, but it has not shown clinically significant effects. Therefore, neural tissue engineering strategies have aimed to address this severely limited area of treatment.

Cell-Based Therapy

Cell-based therapies aim to promote the survival of damaged neural cells or manipulate the local area to more conducive for regeneration by providing neurotrophic factors. MSCs and NSCs are the most investigated for treatment strategies to either regenerate damaged native tissue by replacing damaged cells and directly integrating into the tissue or secreting neurotrophic factors to promote neural regeneration or protection (Teng, Y. D., et al., Functional recovery following traumatic spinal cord injury mediated by a unique polymer scaffold seeded with neural stem cells. Proceedings of the National Academy of Sciences, 2002. 99(5): p. 3024-3029; Abematsu, M., et al., Neurons derived from transplanted neural stem cells restore disrupted neuronal circuitry in a mouse model of spinal cord injury. The Journal of clinical investigation, 2010. 120(9): p. 3255; Hofstetter, C., et al., Marrow stromal cells form guiding strands in the injured spinal cord and promote recovery. Proceedings of the National Academy of Sciences, 2002. 99(4): p. 2199-2204; Chopp, M., et al., Spinal cord injury in rat: treatment with bone marrow stromal cell transplantation. Neuroreport, 2000. 11(13): p. 3001-3005; Lu, P., et al., Neural stem cells constitutively secrete neurotrophic factors and promote extensive host axonal growth after spinal cord injury. Experimental neurology, 2003. 181(2): p. 115-129; and Ankeny, D. P., D. M. McTigue, and L. B. Jakeman, Bone marrow transplants provide tissue protection and directional guidance for axons after contusive spinal cord injury in rats. Experimental neurology, 2004. 190(1): p. 17-31). However, the clinical efficacy of cell transplantation strategies have been limited due to uncontrolled differentiation, poor cell survivability, and poor integration with the host tissue.

MSCs have been utilized as a short-term immunosuppressant to preserve threatened neurons and glial cells after injury. They have been shown to stimulate recovery from acute symptoms aggravated by inflammation (Zeng, X., et al., Bone marrow mesenchymal stem cells in a three-dimensional gelatin sponge scaffold attenuate inflammation, promote angiogenesis, and reduce cavity formation in experimental spinal cord injury. Cell Transplantation, 2011.

20(11-12): p. 1881-1899; and Nakajima, H., et al., Transplantation of mesenchymal stem cells promotes an alternative pathway of macrophage activation and functional recovery after spinal cord injury. Journal of neurotrauma, 2012. 29(8): p. 1614-1625). However, transplanted MSCs have low survival rate in the adult human CNS (Parr, A. M., C. H. Tator, and A. Keating, Bone marrow-derived mesenchymal stromal cells for the repair of central nervous system injury. Bone marrow transplantation, 2007. 40(7): p. 609).

Adult NSCs are capable of differentiating into the three types of neural cell types found in the CNS, neurons, oligodendrocytes, and astrocytes. They have been investigated in combination with growth factors and immunosuppression to treat spinal cord injury (61). NSCs displayed enhanced survival and differentiation into myelinating oligodendrocytes (Hammang, J., D. Archer, and I. Duncan, Myelination following transplantation of EGF-responsive neural stem cells into a myelin-deficient environment. Experimental neurology, 1997. 147(1): p. 84-95). More recently, investigators have challenged the negative reputation of astrocytes in CNS regeneration.

Injectable Hydrogel

Hydrogels mimic the physical, mechanical, and chemical properties of native extracellular matrix to promote cell adhesion, self-renewal, and differentiation (Banerjee, A., et al., The influence of hydrogel modulus on the proliferation and differentiation of encapsulated neural stem cells. Biomaterials, 2009. 30(27): p. 4695-4699). Combining biomolecules and neural cell strategies with hydrogel can further promote cell-material interactions. Studies have shown that NSCs are prone to neuronal differentiation on softer hydrogels, while glial differentiation is induced on stiffer scaffolds (Teixeira, A. I., et al., The promotion of neuronal maturation on soft substrates. Biomaterials, 2009. 30(27): p. 4567-4572; and Leipzig, N. D. and M. S. Shoichet, The effect of substrate stiffness on adult neural stem cell behavior. Biomaterials, 2009. 30(36): p. 6867-6878). Tseng et al. developed an injectable chitosan-based hydrogel and demonstrated the ability of neurosphere-like NSC aggregates to proliferate than differentiate towards neuronal-linages (Tseng, T. C., et al., An injectable, self-healing hydrogel to repair the central nervous system. Advanced materials, 2015. 27(23): p. 3518-3524). Next, they injected the NSC aggregate loaded hydrogel into zebrafish with neural system disorder and monitored the functional recovery. The zebrafish injected with NSC-hydrogel demonstrated the 81% functional recovery, as oppose to 38% recovery with just the hydrogel alone. Although these results show the promising potential of cell-based and hydrogel-based therapies, they are limited by their uncontrollable gelation kinetics, which may result in needle clogging during hydrogel delivery. Also, due to their slow gelation process, the embedded cell or drug may lose its function due to degradation or diffusion from the target area. Its applicability in humans with structurally distinctive mammalian nerve system is still questionable.

Neuroprosthetics

Individuals with C4 or C5 damage in the spinal cord suffer from tetraplegia, the functional loss of upper and lower extremities. Damage occurring at the C5 range results in limitation or completely loss of finger functionality; where as C4 damage also includes limited or loss of function of the hands and elbow movement (White, N.-H. and N.-H. Black, Spinal cord injury (SCI) facts and figures at a glance. 2016). Individuals lose their ability to accomplish basic daily tasks and their independence. Since currently there is no treatment to regenerate damaged axons in the spinal cord to regain full functional recovery, neuroprostheses based on functional electrical stimulation can compensate the loss of functional upper extremities. By electrically stimulating the downstream nerves in the forearms, individuals are given the ability to reach, grasp, and pinch with their hands.

Commercially available grasp neuroprostheses have been offered to patients at very early stage of rehabilitation (Rupp, R., et al., Functional rehabilitation of the paralyzed upper extremity after spinal cord injury by noninvasive hybrid neuroprostheses. Proceedings of the IEEE, 2015. 103(6): p. 954-968). Multiple surface electrodes are placed on the surface of the skin above muscles responsible for hand movement. A forearm sleeve securely wraps the electrodes and a metal splint is integrated into the sleeve to stabilize the wrist. The electrodes will deliver short electrical current impulses to formally excitable tissue. If a minimum charge density surpasses a threshold, the electrical pulses induce physiological action potentials on nerves, causing contractions of innervated, yet paralyzed muscles of the hands and the forearms. However, the grasp prostheses possess several disadvantages, such as reproducibility of desired grasping movements. There is significant variation of the grasp patterns in dependence of the wrist rotation angle. Individuals have also complained about complications of placement of electrodes at home, varying muscle function if not placed correctly. Therefore, on-going research is still seeking strategies to restoring full functionality by complete repair of CNS nerves.

Electrical Stimulation

Due to the innate electrical properties of the nervous system, the potential of utilizing electrical stimulation to enhance nerve regeneration and functional recovery has been widely investigated. Electrical stimulation has been shown to facilitate the processes of axonal regeneration by enhancing the secretion of neurotrophic factors from glial cells promoting neurite outgrowth (Kanzaki, S., et al., Glial cell line-derived neurotrophic factor and chronic electrical stimulation prevent VIII cranial nerve degeneration following denervation. Journal of Comparative Neurology, 2002. 454(3): p. 350-360; and Al-Majed, A. A., et al., Brief electrical stimulation promotes the speed and accuracy of motor axonal regeneration. Journal of Neuroscience, 2000. 20(7): p. 2602-2608). Several in vivo studies demonstrated the efficacy of electrical stimulation promoting nerve outgrowth in rat models of nerve injury, resulting in earlier muscle reinnervation and functional recovery. When electrical stimulation was applied at the time of nerve repair, this resulted in an increased number of sensory neurons that expressed BDNF and its trkB receptor, subsequently accelerating nerve regeneration (Geremia, N. M., et al., Electrical stimulation promotes sensory neuron regeneration and growth-associated gene expression. Experimental neurology, 2007. 205(2): p. 347-359). When electrical stimulation was applied for 14 days to damaged motor neurons, evident by motor reinnervation occurred at 21 days rather than at approximately 42 days and all the motor neurons had regenerated their axons into the motor nerve branch within 21 days instead of 56-70 days observed in the sham control (Brushart, T., Motor axons preferentially reinnervate motor pathways. Journal of Neuroscience, 1993. 13(6): p. 2730-2738).

The first human clinical trial showed a promising potential of therapeutic electrical stimulation, where improved post-surgical outcomes were achieved by localized low frequency of electrical stimulation on patients with carpal tunnel syndrome (Gordon, T., et al., Brief post-surgical electrical stimulation accelerates axon regeneration and muscle reinnervation without affecting the functional measures in carpal tunnel syndrome patients. Experimental neurology, 2010. 223(1): p. 192-202). Despite these positive outcomes, the application of electrical stimulation in the clinical setting is limited by several factors; most significantly, its invasive nature requires the implantation of electrodes protruding through the skin. Furthermore, the electrode approach can activate only neuron(s) in direct contact with or close proximity to the electrodes, resulting in a small localized effective area.

Piezoelectric Materials

Piezoelectric materials can self-generate electric fields under dynamic mechanical strain. Under the direct piezoelectric effect, the materials induce an electric charge separation due to the re-orientation of dipole domains in response to mechanical deformation (tension or compression), providing a means to produce electric potentials without a separate electrical source (Vijaya, M., Piezoelectric materials and devices: applications in engineering and medical sciences2012: CRC Press). Due to its flexibility and biocompatibility, piezoelectric polymers have been used for biomedical applications over its piezoceramic counterparts. There have been several attempts to utilize piezoelectric properties for nerve regeneration (Fine, E. G., et al., Improved nerve regeneration through piezoelectric vinylidenefluoride-trifluoroethylene copolymer guidance channels. Biomaterials, 1991. 12(8): p. 775-780; and Aebischer, P., et al., Piezoelectric guidance channels enhance regeneration in the mouse sciatic nerve after axotomy. Brain research, 1987. 436(1): p. 165-168). Especially, poly(vinylidene fluoride) (PVDF) and its copolymer poly(vinylidene fluoride-trifluoroethylene) (PVDF-TrFE), have been extensively studied for such applications due to their excellent biocompatibility and relatively high piezoelectricity (Teixeira, L., et al., In vitro biocompatibility of poly (vinylidene fluoride-trifluoroethylene)/barium titanate composite using cultures of human periodontal ligament fibroblasts and keratinocytes. Acta biomaterialia, 2010. 6(3): p. 979-989; and Beloti, M. M., et al., In vitro biocompatibility of a novel membrane of the composite poly (vinylidene-trifluoroethylene)/barium titanate. Journal of biomedical materials research Part A, 2006. 79(2): p. 282-288).

Figure 4:
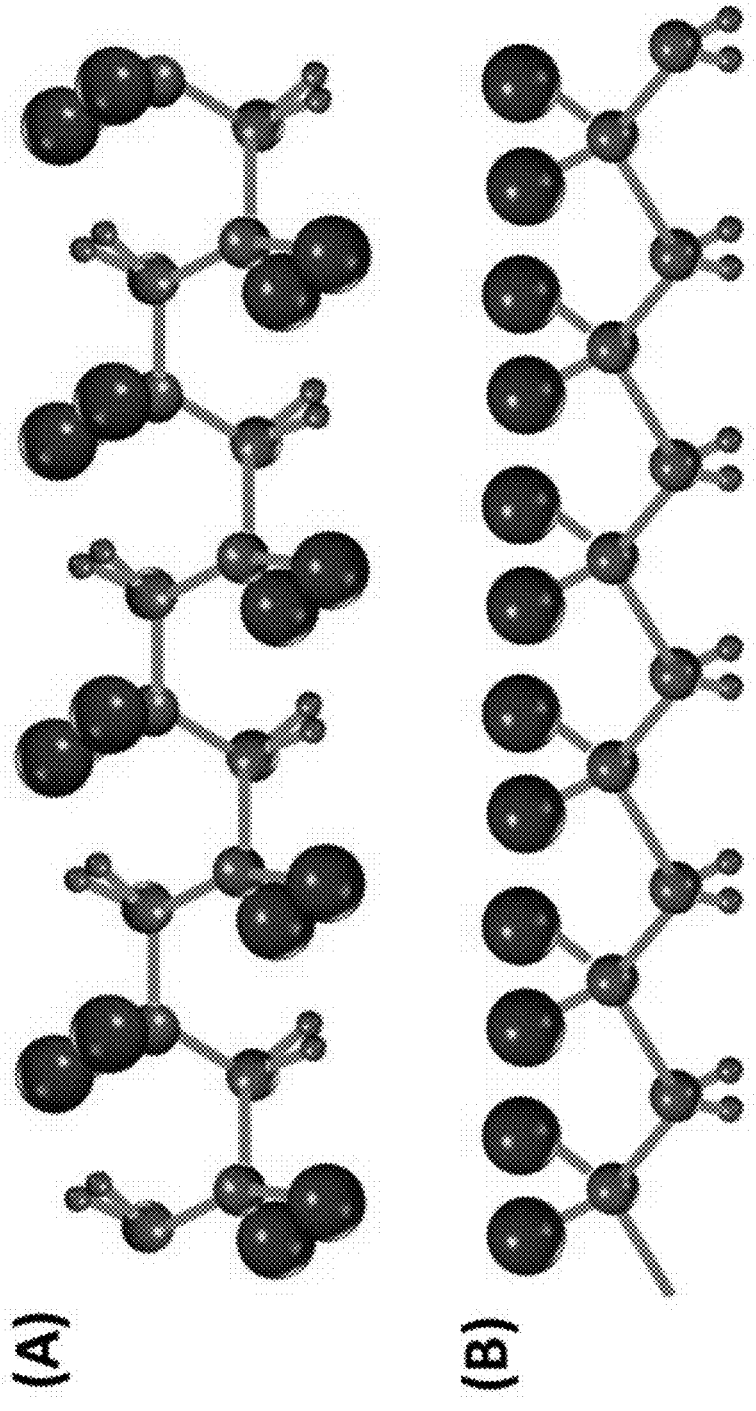
FIG. 4. Molecular structures of piezoelectric poly(vinylidene fluoride) (PVDF) and their effects on piezoelectricity. PVDF can exist in the (A) non-piezoelectric $\alpha$ crystal phase and (B) piezoelectric $\beta$ crystal phase.

PVDF may exist in four crystalline phases, $\alpha$, $\beta$, $\gamma$, and $\delta$ phases, depending on the molecular chain conformations as trans or gauche linkages (FIG. 4). It is non-polar in the $\alpha$ crystal phase, while it is polar in the $\beta$ and $\gamma$ crystal phases. In order to induce its piezoelectric properties by traditional synthesis methods, the polymer is mechanically stretched to 300% strain followed by poling to induce a net dipole of trans linkage, transforming into the highly polar $\beta$ crystal phase (Gregorio, R. and E. Ueno, Effect of crystalline phase, orientation and temperature on the dielectric properties of poly (vinylidene fluoride)(PVDF). Journal of Materials Science, 1999. 34(18): p. 4489-4500). Once it is poled, PVDF becomes a ferroelectric polymer, exhibiting both piezoelectric and pyroelectric properties. On the other hand, PVDF-TrFE is directly crystallized into the polar $\beta$ crystal phase, because TrFE acts as a phase stabilizer. Its degree of crystallinity, thus piezoelectric performance can be further enhanced by thermal treatment.

The first use of PVDF and PVDF-TrFE as a nerve guidance conduit was demonstrated in a rat model. The poled PVDF conduit was implanted into the sciatic nerve of a rat with a 4 mm gap. 4 weeks after implantation, there were a significantly higher amount of myelinated axons than the control group (Delaviz, H., et al., Repair of peripheral nerve defects using a polyvinylidene fluoride channel containing nerve growth factor and collagen gel in adult rats. Cell Journal (Yakhteh), 2011. 13(3): p. 137). They also implanted the piezoelectric PVDF-TrFE conduit into a rat sciatic nerve with a 10 mm gap and observed bridging of myelinated axons in 4 weeks, demonstrating the capability of PVDF-TrFE as a nerve guidance conduit for nerve regeneration (Delaviz, H., et al., Ultrastructural Changes in Spinal Motoneurons and Locomotor Functional Study after Sciatic Nerve Repair in Conduit Tube. Iranian journal of basic medical sciences, 2012. 15(4): p. 990).

Figure 5:
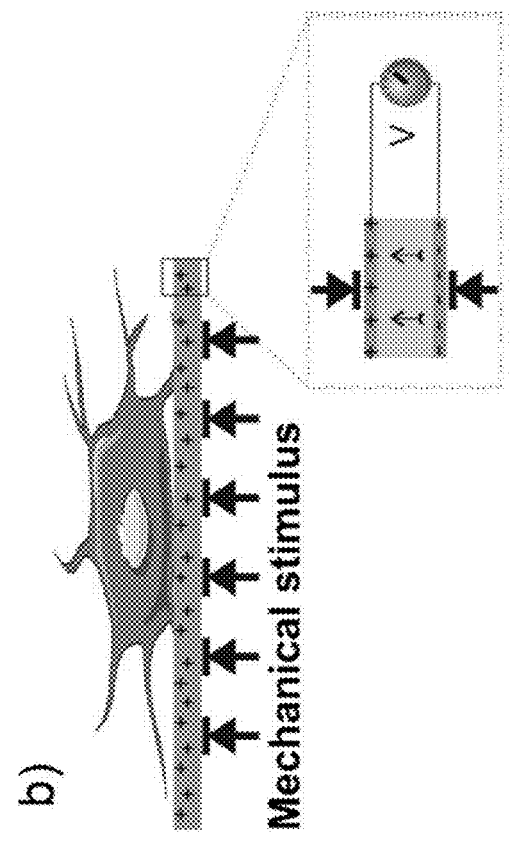
FIG. 5. Mechanical/electrical stimulation modulates cellular behavior. (a) The static state with native surface charges and (b) activated state under mechanical stress generates surface electric charges that can directly affect adherent cells. (see, Ribeiro, C., et al., Piezoelectric polymers as biomaterials for tissue engineering applications. Colloids and Surfaces B: Biointerfaces, 2015. 136: p. 46-55).
Figure 5:
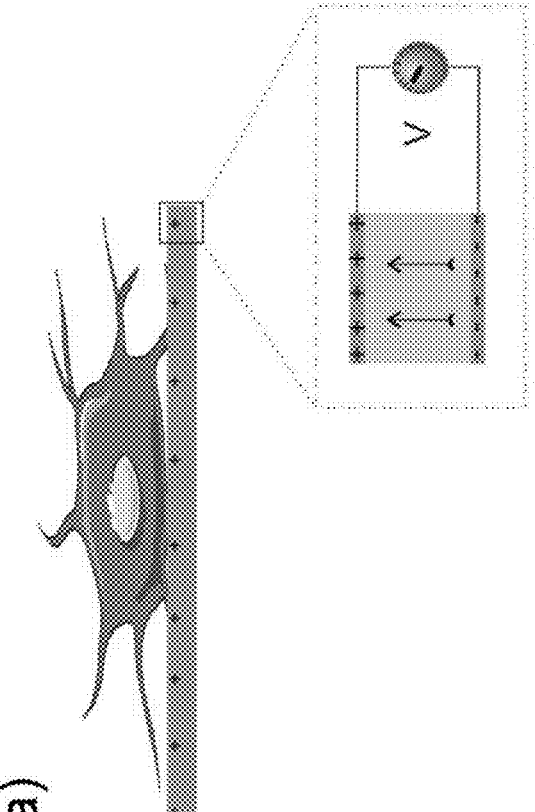

More recently, a group of researchers exploited the enhanced piezoelectricity of PVDF-TrFE scaffolds synthesized by electrospinning to accelerate neurite outgrowth of dorsal root ganglion neurons (Lee, Y.-S., G. Collins, and T. L. Arinzeh, Neurite extension of primary neurons on electrospun piezoelectric scaffolds. Acta biomaterialia, 2011. 7(11): p. 3877-3886) or promote neural differentiation of human neural stem/progenitor cells in vitro (Lee, Y.-S. and T. L. Arinzeh, The influence of piezoelectric scaffolds on neural differentiation of human neural stem/progenitor cells. Tissue Engineering Part A, 2012. 18(19-20): p. 2063-2072). In spite of favorable results, these studies were likely unable to utilize the true potential of piezoelectricity as it requires dynamic straining of the materials to generate electric potentials. They attributed the enhancement of cellular behaviors to piezoelectric responses of the PVDF scaffold by cell exerting forces, but considering minimal straining possible by the cells, the effects were probably due to intrinsic surface charges of the material (FIG. 5).

Electrospinning

Figure 6:
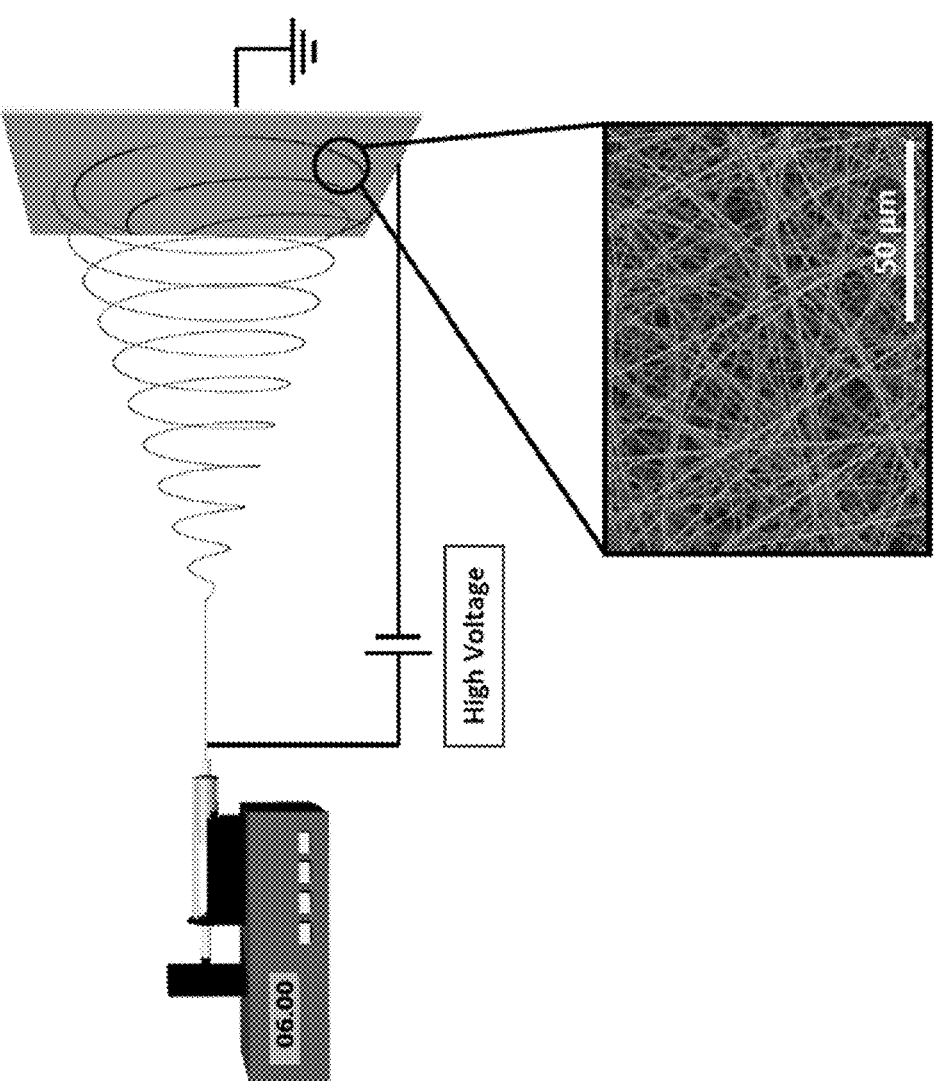
FIG. 6. Electrospinning produces native extracellular matrix (ECM)-like structures. An electric field elongates a polymeric solution to synthesize fibrous structures with enhanced piezoelectric properties that resemble native ECM.

The development of fibrous scaffolds processed by the electrospinning technique has received much attention for neural tissue engineering applications to facilitate the regrowth of damaged nerves (Yang, F., et al., Electrospinning of nano/micro scale poly (L-lactic acid) aligned fibers and their potential in neural tissue engineering. Biomaterials, 2005. 26(15): p. 2603-2610). The technique can produce a non-woven or aligned network of fibers that mimic native extracellular matrix (FIG. 6). An engineered scaffold can be loaded with cells and growth factors to promote functional restoration. The surface and mechanical properties of the scaffold, similar to the environmental cues in the extracellular matrix, can stimulate cell self-renewal and differentiation (Maldonado, M., et al., The effects of electrospun substrate-mediated cell colony morphology on the self-renewal of human induced pluripotent stem cells. Biomaterials, 2015. 50: p. 10-19; and Maldonado, M., et al., Enhanced Lineage-Specific Differentiation Efficiency of Human Induced Pluripotent Stem Cells by Engineering Colony Dimensionality Using Electrospun Scaffolds. Advanced healthcare materials, 2016. 5(12): p. 1408-1412). It also possesses the same architecture as native extracellular matrix, which high surface to volume ratio, allowing more contact between the cells and the scaffold. A wide range of polymers can be used to manipulate the physical and biological properties of the scaffold, from biodegradability, mechanical properties, and surface wettability. The electrospinning process consists of a high voltage power source, syringe and needle, syringe pump, and a grounded collector. A polymer dissolved in a solvent is loaded into a syringe with a needle and placed on a syringe pump. The polymer solution is ejected at a controlled flow rate by the syringe pump. A high voltage charges the polymer solution and when the electrostatic force overcomes the surface tension of the polymer solution at the tip of the needle, a Taylor cone is formed, elongating the polymer solution into a jet. The charged jet is deposited on to a grounded collector due to the electric field between the needle tip and targeted collector. Randomly-oriented fibers can be collected on a static flat collector, while aligned fibers are typically collected on a high speed rotating mandrel, which allows the fibers to collect in the direction of rotation.

The polymer solution properties (viscosity, conductivity and surface tension), electrospinning parameters (electric field, solution flow rate, and collector type), and environmental conditions (temperature and relative humidity) are the main governing parameters to precisely control the fiber diameter and orientation (Beachley, V. and X. Wen, Effect of electrospinning parameters on the nanofiber diameter and length. Materials Science and Engineering: C, 2009. 29(3): p. 663-668). It was found that the factor that has the greatest impact on fiber diameter is solution properties, more specifically the solution viscosity, while electro-conductivity and dielectric properties of the solution significantly affect individual fiber morphology.

Structural characteristics of electrospun scaffolds, such as fiber diameter and alignment have been shown to modulate cellular behaviors, especially neural cell types. NSCs have been shown to exhibit the greatest differentiation potential towards neurons on aligned microfibers than that of random and nano-sized electrospun fibers, due to having a larger platform to extend its neurites in one direction (Yang, F., et al., Electrospinning of nano/micro scale poly (L-lactic acid) aligned fibers and their potential in neural tissue engineering. Biomaterials, 2005. 26(15): p. 2603-2610). An aligned electrospun platform also enhanced Schwann cell maturation (Chew, S. Y., et al., The effect of the alignment of electrospun fibrous scaffolds on Schwann cell maturation. Biomaterials, 2008. 29(6): p. 653-661). These results demonstrate the potential of aligned electrospun scaffolds to prime cells for neural applications.

Figure 7:
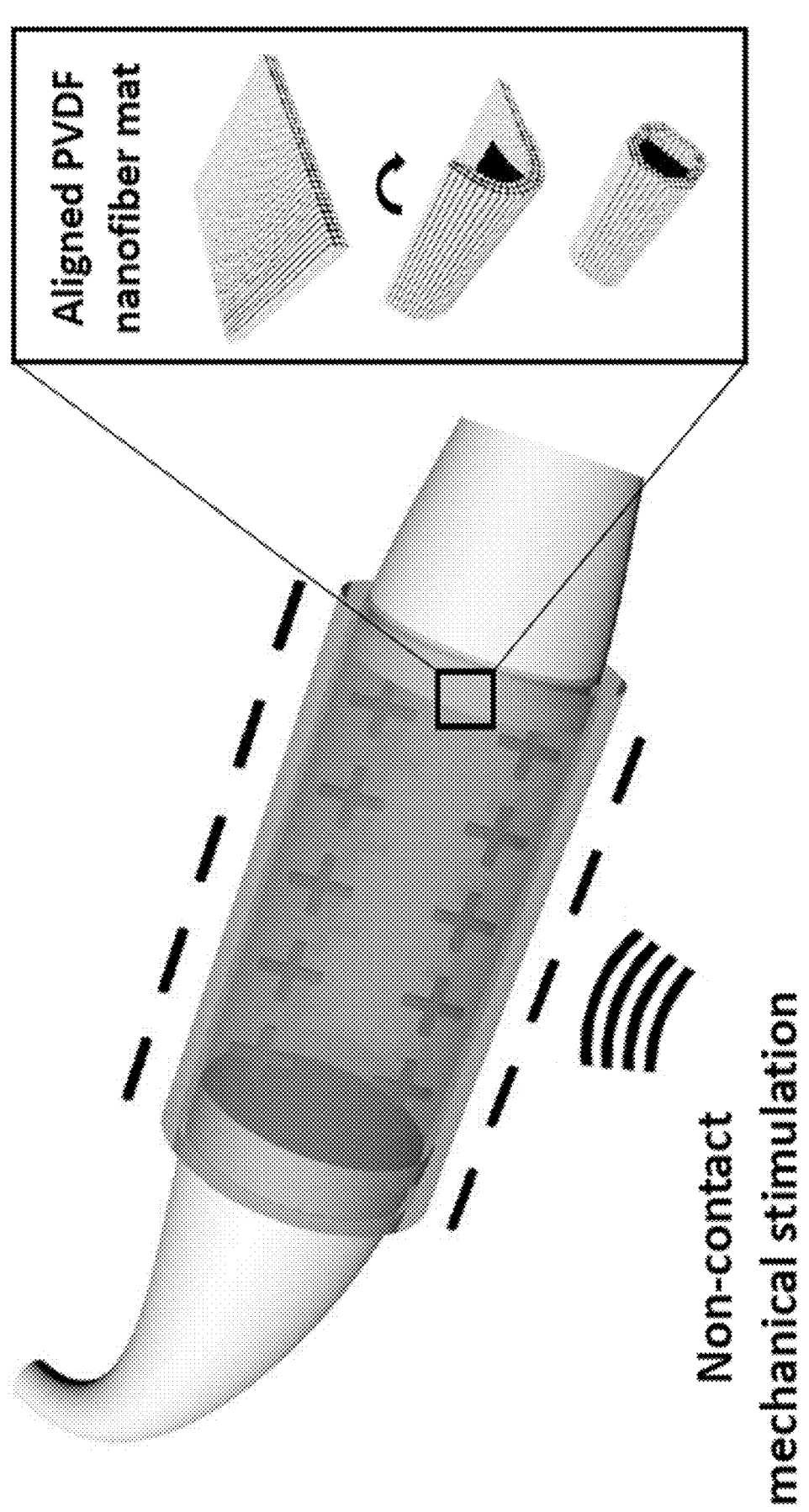
FIG. 7. A schematic of a piezoelectric neuroconduit composed of electrospun aligned PVDF-TrFE. The implanted neuroconduit can be activated by externally applied mechanical stimulation to produce electric fields for enhancing and promoting nerve regeneration in the PNS and CNS.

A lack of technologies that enable electrically stimulating nervous tissues in a facile and clinically relevant manner has partly hindered the advancement in treating nerve injuries for full functional recovery. In this regard, have developed a mechanical/electrical stimulation system. Optimized levels of electrical stimulation are applied to damaged tissue by remotely activating the conduit wrapping around injured nerves via acoustically-driven piezoelectricity. Unlike biochemical-embedded conduit in which the release of neurotrophic factors is limited by loading or electro-conductive conduit in which only passive electrical stimulation by autologous cells is possible without intrusive electrodes, the piezoelectric conduit provides unlimited opportunity to properly stimulate the neuronal cells in vivo. We have developed a novel method of peripheral and central nerve treatment that allows functional recovery of nerve injuries with a previously untreatable large gap in a shorter duration (FIG. 7).

Example 1

Development of a Piezoelectric Cell Culture System for Neuroengineering Studies

Due to the innate electrical behavior of nerve tissue, the use of electrical stimulation to enhance nerve regeneration is widely investigated. The activation of neural cells by electrical stimulation has been demonstrated to play a significant role in enhancing functional recovery of degenerated neurons. However, the application of electrical stimulation for axon regrowth has been limited in the clinical setting due to the invasiveness of electrodes and limited effective area. In the present study, we designed and developed a cell culture system to deliver electrical stimulation to neural cells in vitro, by non-contact activation of a piezoelectric-responsive polyvinylidene fluoride trifluoroethylene (PVDF-TrFE) to demonstrate the feasibility of using piezoelectric materials for nerve regeneration. The electrospinning technique was utilized to synthesize aligned nanofibrous structures to control the nanostructure of the PVDF-TrFE. We demonstrate the capability the piezoelectric cell culture system to precisely control the electric potential generation of the PVDF-TrFE by modulating the fiber diameter and scaffold thickness while the system provides a means to sterilely culture cells. This cell culture system can be utilized for various neuroengineering studies to examine the effects of mechanical/electrical stimulation on nerve regeneration.

Nerve damage due to traumatic injuries or degenerative diseases, such as diabetic neuropathy or neurofibromatosis, is not only potentially fatal, but also have a debilitating effect on the quality of life. Despite surgical intervention, full functional recovery is rarely achieved. The deficiency of complete axon regeneration is not due to the lack of cellular capability, rather the unfavorable growth environment within the damage tissue preventing axon regeneration. To overcome this, tissue engineering strategies have focused on altering the cellular, molecular, and physical environment to promote proper nerve regeneration. Researchers have incorporated various types of stem cells, including induced pluripotent stem cells (iPSCs) (Uemura, T., et al., *Long-term efficacy and safety outcomes of transplantation of induced pluripotent stem cell-derived neurospheres with bioabsorbable nerve conduits for peripheral nerve regeneration in mice*. Cells Tissues Organs, 2014. 200(1): p. 78-91; and Ikeda, M., et al., *Acceleration of peripheral nerve regeneration using nerve conduits in combination with induced pluripotent stem cell technology and a basic fibroblast growth factor drug delivery system*. Journal of biomedical materials research Part A, 2014. 102(5): p. 1370-1378), neural stem cells (NSCs) (Zhang, H., et al., *Implantation of neural stem cells embedded in hyaluronic acid and collagen composite conduit promotes regeneration in a rabbit facial nerve injury model*. Journal of translational medicine, 2008. 6(1): p. 67; and Hsu, S.h., C. H. Su, and I. M. Chiu, *A novel approach to align adult neural stem cells on micropatterned conduits for peripheral nerve regeneration: a feasibility study*. Artificial Organs, 2009. 33(1): p. 26-35), and mesenchymal stem cells (MSCs) (Keilhoff, G., et al., *Transdifferentiation of mesenchymal stem cells into Schwann cell-like myelinating cells*. European journal of cell biology, 2006. 85(1): p. 11-24; and Hu, J., et al., *Repair of extended peripheral nerve lesions in rhesus monkeys using acellular allogenic nerve grafts implanted with autologous mesenchymal stem cells*. Experimental neurology, 2007. 204(2): p. 658-666) into implantable neuroconduits to enhance axonal regeneration. In addition to these cellular strategies, nerve growth factor (NGF), a neurotrophic protein, has been incorporated to further stimulate nerve regeneration (7; 8; and 9). However, such biochemical factors have a short half-life and fast diffusion rate, limiting its use in vivo for axonal regeneration that requires long-term stimulation.

As a biophysical cue, electrical stimulation has been shown to have the ability to initiate an action potential of a damaged neuron to enhance the axon regeneration process (7; 8; and 9). When a neuron is exposed to electrical current, i.e., by ion movement across the cell membrane, it creates a gradient of extracellular electrical potential. If the electrical potential is above a threshold, it induces the depolarization of the axon membrane, generating an action potential. Exogenous electrical stimulation has been also shown to initiate such signaling processes, which induce anabolic activities of neural cells, collectively promoting nerve regeneration. In this regard, conductive materials have been commonly used as an electrical substrate suitable for the electrical stimulation of neural cells (Lee, A. C., et al., *Controlled release of nerve growth factor enhances sciatic nerve regeneration*. Experimental neurology, 2003. 184(1): p. 295-303; Brown, M. C., et al., *Macrophage dependence of peripheral sensory nerve regeneration: possible involvement of nerve growth factor*. Neuron, 1991. 6(3): p. 359-370; and Rich, K. M., et al., *Nerve growth factor enhances regeneration through silicone chambers*. Experimental neurology, 1989. 105(2): p. 162-170). However, their invasive implantations of electrodes to activate the conductive materials make its translational usage limited.

To address this issue, piezoelectric materials have drawn attention as a potential generating material activated by mechanical stimulation. Especially, polyvinylidene fluoride (PVDF), a piezoelectric polymer, provides an opportunity to develop nerve conduits due to its high piezoelectricity, biocompatibility, and mechanical compliance. Indeed, several studies have shown enhanced nerve regeneration by the utilization of the PVDF in vitro, such as neurite elongation dorsal root ganglion (Lee, Y.-S., G. Collins, and T. L. Arinzeh, *Neurite extension of primary neurons on electrospun piezoelectric scaffolds*. Acta biomaterialia, 2011. 7(11): p. 3877-3886), and in vivo, such as partial functional recovery when a PVDF conduit was implant (Lee, Y. S., et al., *Enhanced noradrenergic axon regeneration into schwann cell-filled PVDF-TrFE conduits after complete spinal cord transection*. Biotechnology and bioengineering, 2017. 114 (2): p. 444-456).

Electrospinning is a facile technique to synthesize nanofibers of almost any polymers, including PVDF, producing a structure that closely resembles the native extracellular matrix (ECM) of tissues (Yang, F., et al., *Electrospinning of nano/micro scale poly (L-lactic acid) aligned fibers and their potential in neural tissue engineering*. Biomaterials, 2005. 26(15): p. 2603-2610; and Lannutti, J., et al., *Electrospinning for tissue engineering scaffolds*. Materials Science and Engineering: C, 2007. 27(3): p. 504-509). Modification of the electrospinning process easily controls the physical properties of the scaffold, such as fiber diameter and alignment, which affect the piezoelectricity of PVDF and modulate cellular behaviors (Lee, Y.-S., G. Collins, and T. L. Arinzeh, *Neurite extension of primary neurons on electrospun piezoelectric scaffolds*. Acta biomaterialia, 2011. 7(11): p. 3877-3886; and Martins, P., et al., *Effect of poling state and morphology of piezoelectric poly (vinylidene fluoride) membranes for skeletal muscle tissue engineering*. Rsc Advances, 2013. 3(39): p. 17938-17944). The fiber diameter of electrospun PVDF regulates the uniformity and alignment of piezoelectric domains, determining piezoelectric constants (Ico, G., et al., *Size-dependent piezoelectric and mechanical properties of electrospun P (VDF-TrFE) nanofibers for enhanced energy harvesting*. Journal of Materials Chemistry A, 2016. 4(6): p. 2293-2304). Such changes in substrate morphology also affect cellular behaviors. When comparing neurite growth of neural cell types on randomly-oriented and aligned fiber mats, the cells displayed enhanced neurite elongation on the aligned morphology, likely due to the native elongated structure of neurons (Lee, Y.-S., G. Collins, and T. L. Arinzeh, *Neurite extension of primary neurons on electrospun piezoelectric scaffolds*. Acta biomaterialia, 2011. 7(11): p. 3877-3886).

In this regard, a system composed of a chamber with an insertable piezoelectric cell culture scaffold and a vertical translation stage, was develop to apply non-contact electrical stimulation to adherent cells to examine cellular behaviors for neural applications. Aligned piezoelectric fibers made of polyvinylidene fluoride trifluoroethylene (PVDF-TrFE) were synthesized by electrospinning and their morphological and piezoelectric properties were characterized. The effects of PVDF-TrFE fiber diameter and scaffold thickness on electric potential generation were investigated to determine an optimum condition for cellular studies.

Synthesis and Morphological Characterization of Nanofibrous PVDF-TrFE Scaffolds

Figure 8:
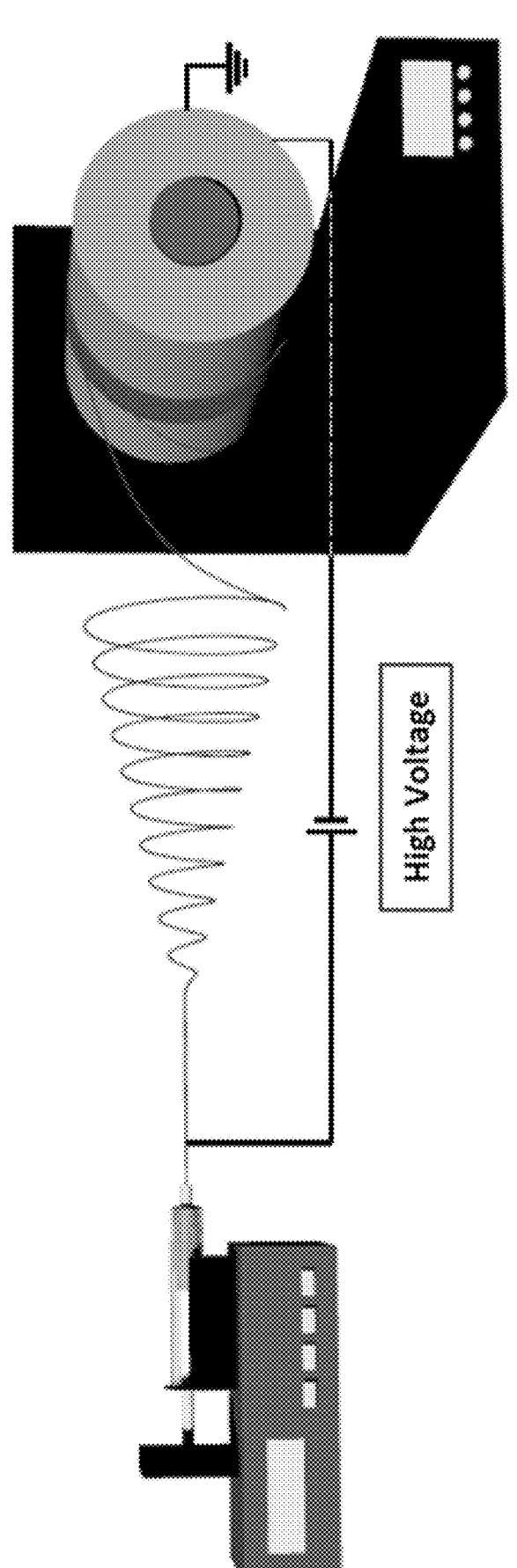
FIG. 8. Electrospinning using a rotating mandrel. An electric field elongates a polymeric solution onto a high speed rotating mandrel to synthesize an aligned fibrous structure that is ideal for culturing neural cell types.

PVDF-TrFE (Solvay, Belgium) was dissolved at various concentrations in different solvent systems to produce a range of different electrospun fiber diameters, similar to our previous report (ref). A 16 wt. % PVDF-TrFE (70:30 mol %) was dissolved in a 60/40 volume ratio of N,N-dimethylformamide (DMF) (Sigma Aldrich, St. Louis, MO) to methyl ethyl ketone (MEK) (Sigma Aldrich) solvent system. 11.5 wt. % and 7 wt. % PVDF-TrFE were dissolved in a 60/40 volume ratio of DMF to acetone solvent system, with the addition of 1 wt. % pyridinium formate (PF) buffer (Sigma Aldrich). The solutions were magnetically stirred at 1200 rpm for 3 hr at room temperature. The PVDF-TrFE solutions were individually electrospun using a high speed grounded mandrel rotating at 47.9 m/s to produce aligned fibers (FIG. 8). To further enhance the piezoelectric properties of PVDF-TrFE, the electrospun fiber mats were subjected to annealing at 90° C. for 24 hr.

The fiber morphology, diameter and alignment were characterized using scanning electron microscopy (SEM, Vega3, Tescan, Pleasanton, CA). The fibers were sputter-coated with gold to visualize under SEM. Using the ImageJ software, at least 100 individual fibers were assessed to determine the average fiber diameter and alignment. The thickness of the fiber mat was controlled by adjusting the deposition time.

Cell Culture Chamber Design

Figure 9:
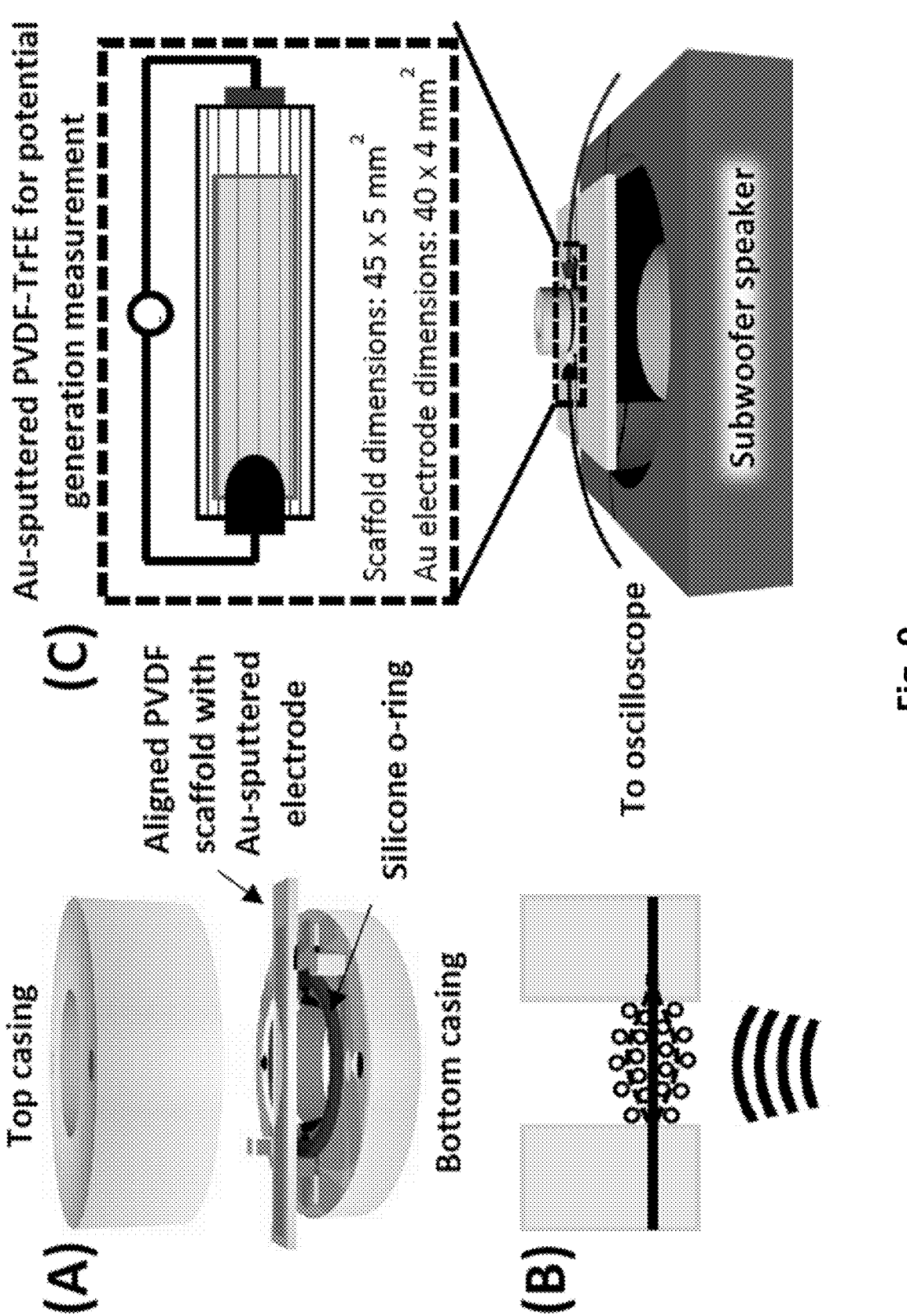
FIG. 9. Piezoelectric cell culture system. (A) A schematic of the expanded cell culture system. (B) Mechanism for driving PVDF-TrFE nanofibers to produce an electric potential. (C) A schematic of a subwoofer speaker set up for activating PVDF-TrFE scaffolds and measuring the potential generation.

A cell culture system was designed to apply non-contact mechanical/electrical stimulation to the nanofibrous PVDF-TrFE scaffolds while sterilely culture cells adherent to the scaffolds (FIG. 9, A). The device was designed to fit into a standard 6-well tissue culture plate. The top and bottom casings were 3D printed with acrylonitrile butadiene styrene (ABS) to sustain a silicone o-ring on both sides. When assembled, the PVDF scaffold is securely held by the silicone o-rings. Stainless steel screws were utilized to hold the two casings together. The hollow center provides a space to host a PVDF-TrFE scaffold having the dimensions of 15 mm×5 mm with cell culture media.

Potential Generation Measurement

To determine the potential generation of the PVDF-TrFE nanofibers, acellular nanofibrous scaffolds assembled in the cell culture system were subjected to non-contact mechanical stimulation (FIG. 9, B). PVDF-TrFE scaffolds were cut to the dimensions of 45 mm by 5 mm. The excess length allows the scaffold to protrude outside of the chamber for alligator clamp attachment to an oscilloscope. Gold electrodes with the dimension 40 mm by 4 mm were sputtered on both sides of the scaffolds. A hydrophobic polymer, poly(styrene-b-isobutylene-b-stryrene) (SIBS) was applied to the gold sputtered scaffolds in the location where it would be compressed by the silicone o-rings, to prevent damage to the fiber structures and solution leak. The scaffold was then assembled into the cell culture system and 3 mL of DI water was added to the center of the chamber. The chamber was placed on a vertical translation stage, actuated by a sub-woofer speaker (FIG. 9, C). The speaker was controlled by a function generator operated by LabView to stimulate the PVDF-TrFE scaffold inside the device at 3 Hz with various magnitudes. The strains experienced by the scaffolds under various magnitudes of actuation were calculated from the captured images of scaffolds under stimulation. The resulting voltage generation was recorded by an oscilloscope. The peak to peak output voltage was determined for 200, 500, and 800 nm fiber diameter at various scaffold thicknesses.

Synthesis of Piezoelectric PVDF-TrFE Nanofibers

Figure 10:
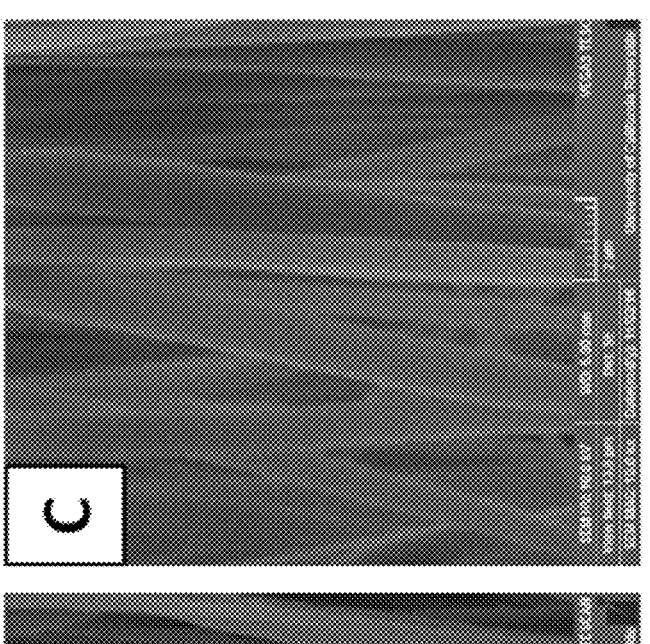
FIG. 10. Morphological characterization of electrospun PVDF-TrFE aligned nanofibers with various fiber diameters. Representative SEM micrographs of PVDF-TrFE aligned nanofibers from (A) 7% PVDF-TrFE dissolved in DMF/Acetone with PF buffer, (B) 11.5% PVDF-TrFE dissolved in DMF/Acetone with PF buffer, and (C) 16% PVDF-TrFE dissolved in DMF/MEK.
Figure 10:
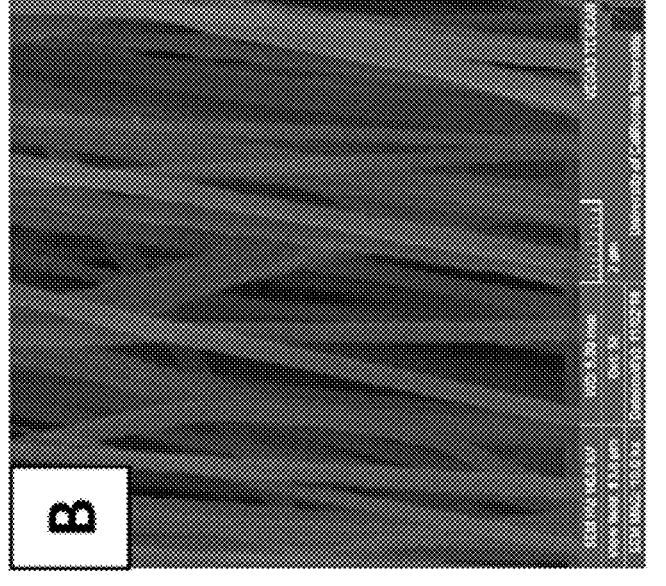
Figure 10:
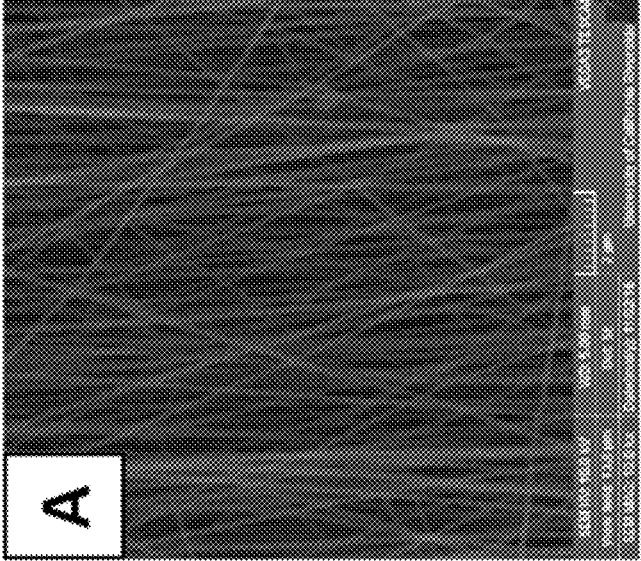
Figure 11:
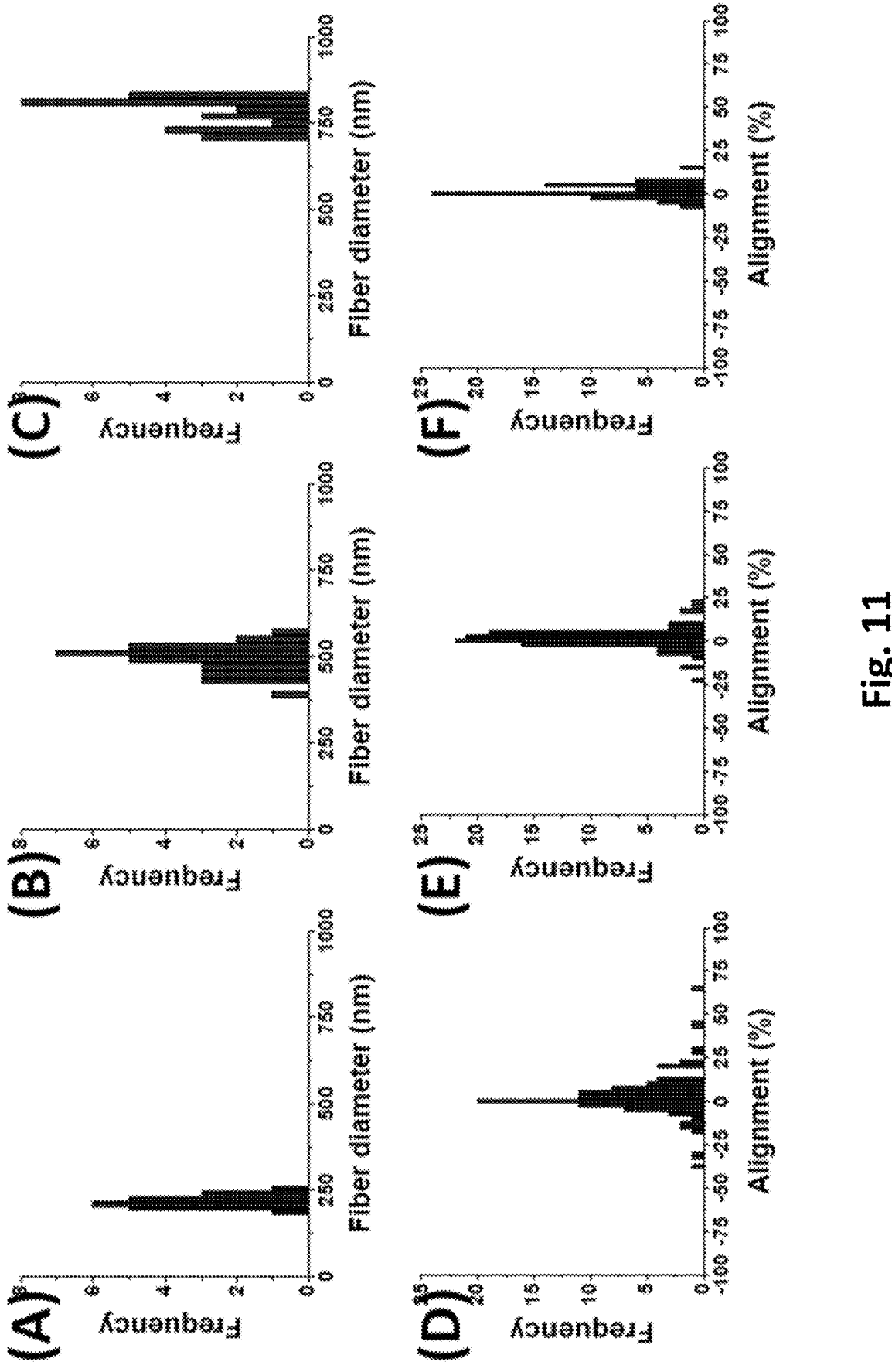
FIG. 11. Quantitative analysis of electrospun PVDF-TrFE aligned nanofiber morphologies. SEM images of PVDF-TrFE aligned nanofibers were quantified to determine (A-C) average fiber diameters and (D-F) alignment from (A,D) 7% PVDF-TrFE dissolved in DMF/Acetone with PF buffer, (B,E) 11.5% PVDF-TrFE dissolved in DMF/Acetone with PF buffer, and (C,F) 16% PVDF-TrFE dissolved in DMF/MEK.
Figure 12:
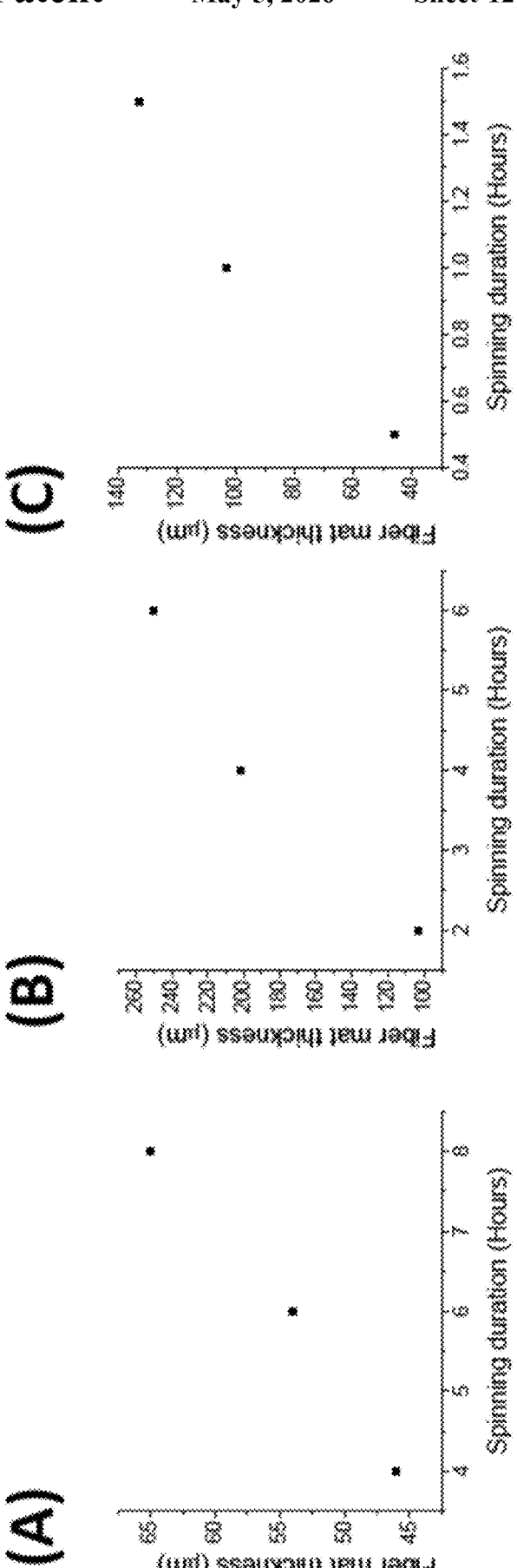
FIG. 12. Deposition rate of electrospun PVDF-TrFE fiber mat. A relationship between the thickness of fiber mat as a function of electrospinning duration was determined to control fiber mat thickness for (A) 200, (B) 500, and (C) 800 nm fiber diameter scaffolds.

FIG. 10 shows the microstructure of electrospun fibers synthesized by various concentrations of PVDF-TrFE examined by SEM. Due to the high angular velocity of the rotating mandrel, the fibers are aligned with a relatively uniform size having a typical cylindrical morphology. A quantitative analysis of the fibers indicates the tightly controlled average fiber diameter for the three conditions (FIG. 11, A-C). The average fiber diameter from 7% PVDF-TrFE dissolved in DMF/Acetone with PF buffer is 205±28 nm; 11.5% PVDF-TrFE dissolved in DMF/Acetone with PF buffer is 498±57 nm; and 16% PVDF-TrFE dissolved in DMF/MEK is 802±16 nm. Fiber diameters will be referred as 800, 500, and 200 nm from here on. The fiber alignment was also assessed by measuring tilt angles of individual fibers from an arbitrary neutral axis, showing above 90% within 200 deviation in all conditions (FIG. 11, D-F). A comprehensive table including the solution mixture, electrospinning parameters, and fiber morphological analyses can be found in Table 2. The thickness of the fiber mat was controlled by adjusting the electrospinning duration. The deposition rates for 200, 500, 800 nm fiber diameter scaffolds were approximately 11.5, 46.3, and 103.0 µm/hr, respectively (FIG. 12).

TABLE 2

Optimized electrospinning parameters of PVDF-TrFE nanofibrous scaffolds having various fiber diameters and their morphological characterization.

| | Solution | | |
|---|---|---|---|
| [Polymer] % | 7 | 11.5 | 16 |
| Solvent | DMV/Acetone/PF | DMV/Acetone/PF | DMV/MEK |
| | Electrospinning conditions | | |
| Flow rate (mL/hr) | 2 | 6 | 6 |
| Distance (cm) | | 10 | |
| Rotating speed (m/s) | | 4709 | |
| | Environmental conditions | | |
| RH (%) | | 40 | |
| T (° C.) | | 23 | |
| | Resulting fibers | | |
| Fiber diameter (nm) | 205 ± 28 | 498 ± 57 | 802 ± 17 |
| Alignment (% within 10°) | 79 | 86 | 93.5 |
| Alignment (% within 20°) | 92 | 94 | 98.4 |

Quantification of Potential Generation from PVDF-TrFE Nanofibers

Figure 13:
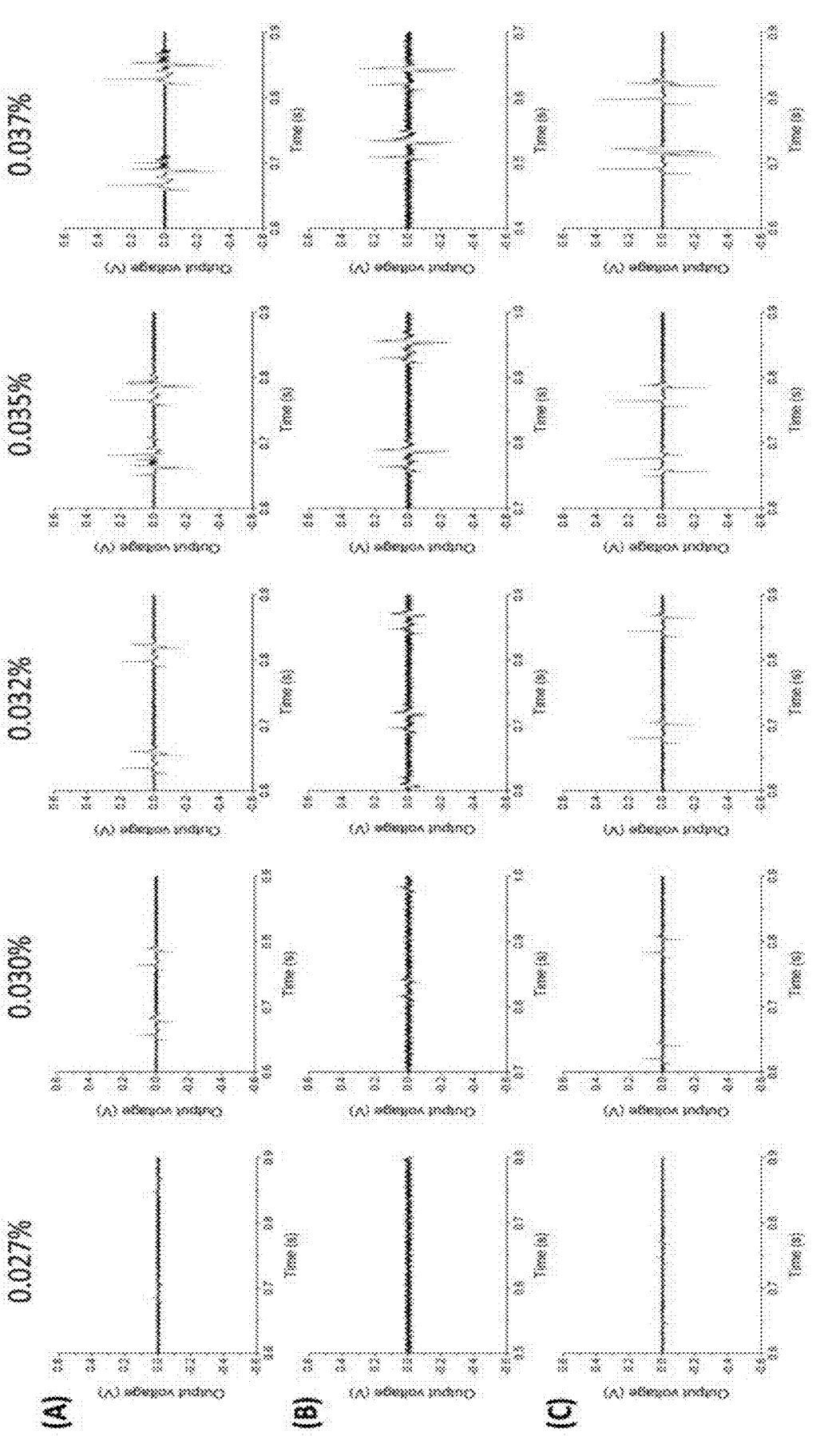
FIG. 13. Potential generation of PVDF-TrFE nanofibers with an average fiber diameter of 200 nm. Representative plots of the peak-to-peak voltage response to different strains at (A) 46, (B) 54, (C) 65 $\mu$m.
Figure 14:
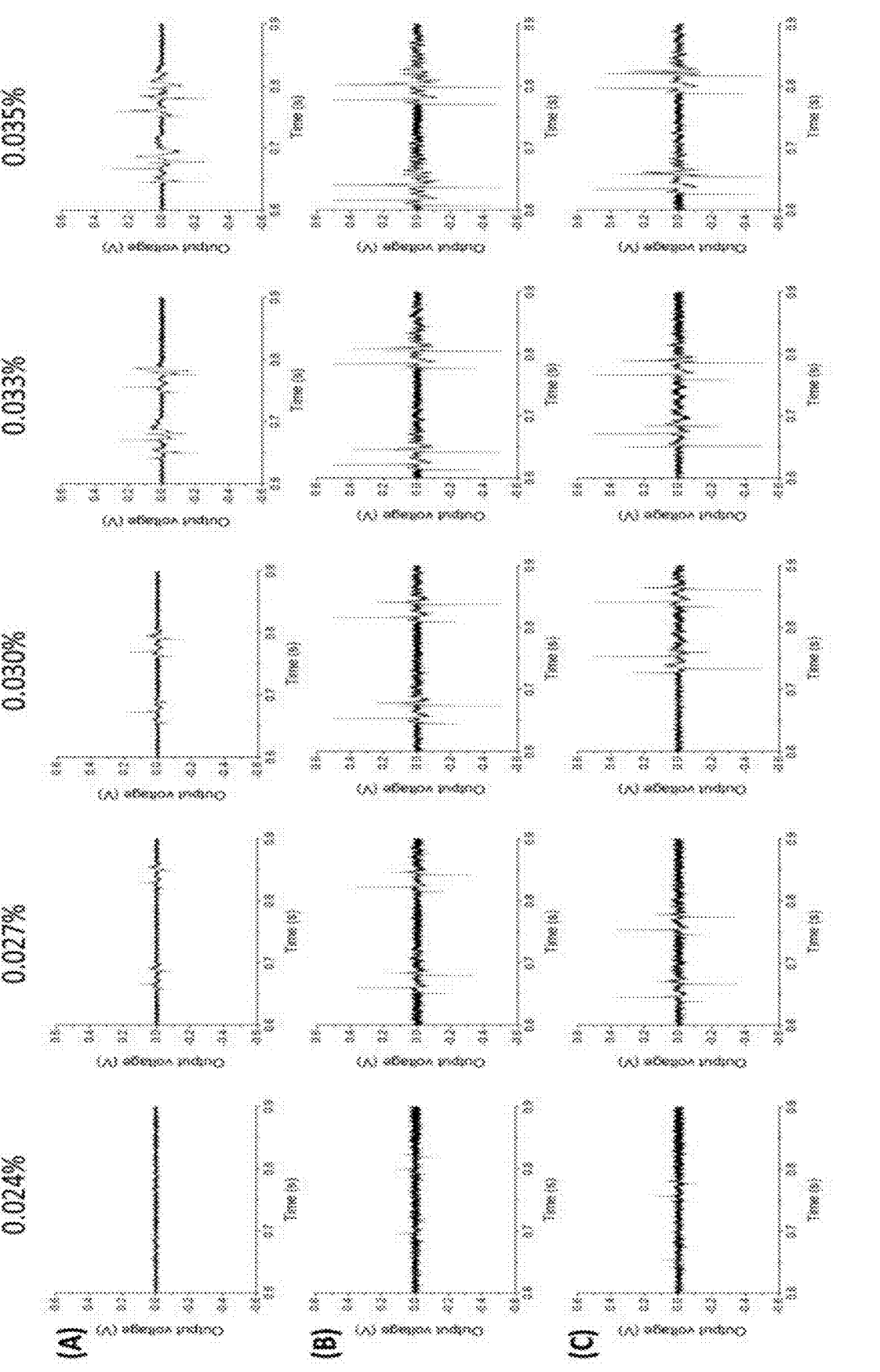
FIG. 14. Potential generation of PVDF-TrFE nanofibers with an average fiber diameter of 500 nm. Representative plots of the peak-to-peak voltage response to different strains at (A) 48, (B) 103, (C) 202 $\mu$m.
Figure 15:
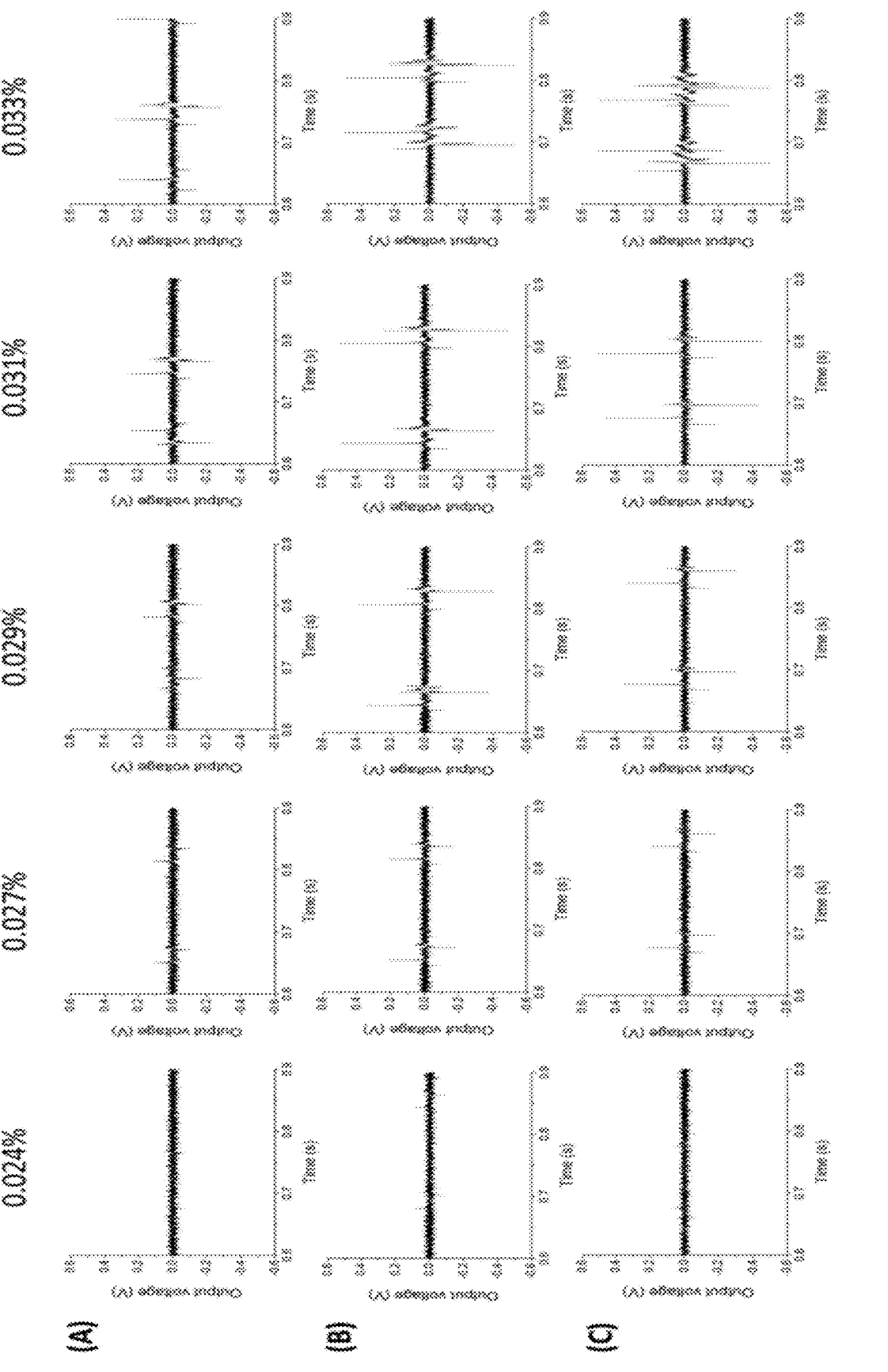
FIG. 15. Potential generation of PVDF-TrFE nanofibers with an average fiber diameter of 800 nm. Representative plots of the peak-to-peak voltage response to different strains applied at (A) 46, (B) 103, (C) 133 km.
Figure 16:
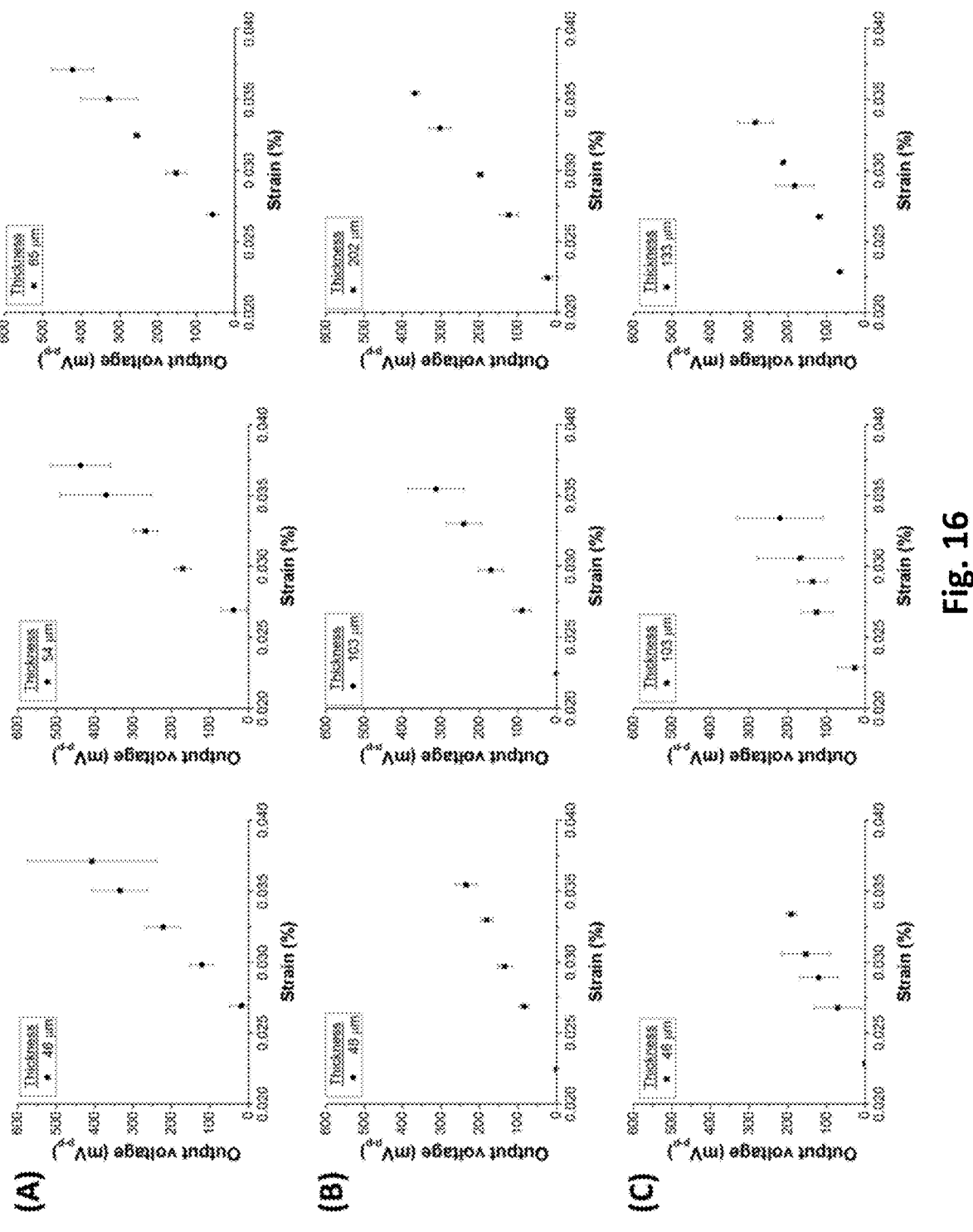
FIG. 16. Potential generation of PVDF-TrFE nanofibers with various fiber diameters and fiber mat thickness stimulated at different strains. A relationship between the peak-to-peak output voltage as a function of applied strain was determined for (A) 200, (B) 500, and (C) 800 nm fiber diameter scaffolds.

When the PVDF-TrFE scaffolds are subjected to mechanical stimulation within the piezoelectric cell culture system, a charge separation occurs with an opposing polarity on each side (FIG. 9B). This charge separation was recorded as a positive to negative voltage peak by an oscilloscope. The peak-to-peak voltage was recorded at various strains to determine a relationship between strain and output voltage. As expected, when the applied strain increased, the peak-to-peak voltage increased (FIGS. 13, 14, and 15). For a fiber mat with the fiber diameter of 200 nm and a fiber mat thickness of 54 μm, at the highest strain of 0.037%, the scaffold produced 437±78 mVp-p and at the lowest strain of 0.027%, it produced 38±34 mVp-p. At the same fiber mat thickness, a scaffold with the fiber diameter of 500 nm produced 234±27 mVp-p at 0.035% strain and 34±12 mVp-p at 0.024% strain; a scaffold with the fiber diameter of 800 nm produced 191±13 mVp-p at 0.033% strain and 27±17 mVp-p at 0.023% strain. Finally, the output voltage was recorded at various thicknesses. FIG. 16 shows the relationship between applied strain to the PVDF-TrFE scaffold and its output voltage production at 200, 500, and 800 nm fiber diameter at various thicknesses.

Due to the innate electro-responsive characteristics of neural cells, electrical stimulation has been widely studied to enhance neural cell behavior in vitro (Schmidt, C. E., et al., *Stimulation of neurite outgrowth using an electrically conducting polymer*. Proceedings of the National Academy of Sciences, 1997. 94(17): p. 8948-8953; Richardson, R. T., et al., *The effect of polypyrrole with incorporated neurotrophin-3 on the promotion of neurite outgrowth from auditory neurons*. Biomaterials, 2007. 28(3): p. 513-523; Fields, R. D., E. A. Neale, and P. G. Nelson, *Effects of patterned electrical activity on neurite outgrowth from mouse sensory neurons*. Journal of Neuroscience, 1990. 10(9): p. 2950-2964; and Wood, M. and R. K. Willits, *Short-duration, DC electrical stimulation increases chick embryo DRG neurite outgrowth*. Bioelectromagnetics, 2006. 27(4): p. 328-331) and in vivo (Kerns, J., et al., *Electrical stimulation of nerve regeneration in the rat: the early effects evaluated by a vibrating probe and electron microscopy*. Neuroscience, 1991. 40(1): p. 93-107; Brushart, T. M., et al., *Electrical stimulation promotes motoneuron regeneration without increasing its speed or conditioning the neuron*. Journal of Neuroscience, 2002. 22(15): p. 6631-6638; Alrashdan, M. S., et al., *Thirty minutes of low intensity electrical stimulation promotes nerve regeneration after sciatic nerve crush injury in a rat model*. Acta Neurologica Belgica, 2010. 110(2): p. 168-179; and Sisken, B., et al., *Stimulation of rat sciatic nerve regeneration with pulsed electromagnetic fields*. Brain research, 1989. 485(2): p. 309-316). Typically, this method was approached by implantation of external electrodes alone for a large stimulation area or combined with electro-conductive material for direct and localized electrical stimulation. In this regard, piezoelectric materials provide an opportunity to subject a precisely localized neural tissue area to electrical stimulation without invasive electrodes via non-contact mechanical perturbation. For example, PVDF-TrFE, a piezoelectric polymer, becomes a charged capacitor under mechanical strain to induce electric charge separation between to the two parallel surfaces.

Electrospinning provides a facile means of synthesizing nanofibrous scaffolds by controlling polymer solution properties, electrospinning parameters, and environmental conditions. It can also induce the formation of β crystal phase of PVDF-TrFE, the crystal structure making it piezoelectric (Ico, G., et al., *Size-dependent piezoelectric and mechanical properties of electrospun P (VDF-TrFE) nanofibers for enhanced energy harvesting*. Journal of Materials Chemistry A, 2016. 4(6): p. 2293-2304). During electrospinning, a high voltage source is applied to the polymeric solution to elongate into a very fine jet, making the polymer chains orientate along the fiber length. The molecular conformation for the β crystal phase has the longest chain length amongst the possible five crystal phases. Therefore, the intensive stretching by the electrospinning processes facilitates the conversion of PVDF into β crystal phase, while the solvent evaporation helps retain R crystal phase conformation in the solid fiber. β crystal phase has a direct relationship to voltage output, therefore, the greater the β crystal phase content, the greater the voltage output.

In order to mechanically stimulate the implanted piezoelectric material in a non-contact manner in vivo, extracorporeal shockwave therapy (ESWT) is an ideal candidate. ESWT is a widely utilized method to regenerate damaged tissue by externally applying focused acoustic energy on the skin surface of an injured area and has been an effective therapeutic tool in the field of regenerative medicine. It generates a sonic pulse of mechanical energy driving rapid changes in pressure in a 3-dimensional space. It is characterized by a positive peak within 10 ns, followed by a negative peak up to −10 MPa, with a total life cycle 10 s (Schuh, C. M., et al., *Extracorporeal shockwave treatment: A novel tool to improve Schwann cell isolation and culture*. Cytotherapy, 2016. 18(6): p. 760-770). It has been measured to impact tissues of bones, muscle, etc. ESWT has also been used to enhance nerve regeneration in rats (Wang, B., et al., *Low-Intensity Extracorporeal Shock Wave Therapy Enhances Brain-Derived Neurotrophic Factor Expression through PERK/ATF4 Signaling Pathway*. International journal of molecular sciences, 2017. 18(2): p. 433; and Mense, S. and U. Hoheisel, *Shock wave treatment improves nerve regeneration in the rat*. Muscle & Nerve, 2013. 47(5): p. 702-710). When applied with an energy flux rate of 0.1 mJ/mm2 at 3 Hz, an increase in myelination, increased expression of the neurotrophic factor, neurtrophin-3, and improved functional recovery were observed (Lee, J.-H. and S.-G. Kim, *Effects of extracorporeal shock wave therapy on functional recovery and neurotrophin-3 expression in the spinal cord after crushed sciatic nerve injury in rats*. Ultrasound in medicine & biology, 2015. 41(3): p. 790-796). In this regard, we developed a method to apply non-contact mechanical perturbation to the PVDF-TrFE scaffold to mimic the energy of ESWT by using a subwoofer speaker that oscillates at a controlled frequency and power.

To measure the potential generation of the electrospun PVDF-TrFE scaffold, a cantilever set up with two fixed points, adopted from Ico et al. (Sunderland, S. and F. Walshe, *Nerves and nerve injuries*. 1968), was developed to measure this surface electric charge separation, or voltage output, during mechanical oscillation at a fixed frequency and amplitude. Because water is transmitting environmental noise to the gold, the gold-sputtered electrodes on both sides of the PVDF-TrFE scaffolds were insulated with a flexible hydrophobic polymer, poly(styrene-b-isobutylene-b-stryrene) (SIBS), to prevent water infiltration. SIBS has been used as an encapsulating coating for biomedical applications that require devices to operate in a liquid environment.

To emulate the applied energy of the shockwave system, a subwoofer speaker controlled by a custom LabView problem was utilized to subject the PVDF-TrFE scaffolds to mechanical actuation within the assembled cell culture device. An oscilloscope recorded its potential generation from electric charge separation. A positive to negative potential peak was recorded. This profile occurs when the subwoofer drives down first, the PVDF-TrFE concaves upwards and produces a negative voltage signal. When the subwoofer returns back to the neutral state, the scaffold bends back to the neutral position, causing the signal to reverse and approach back to zero. As the speaker oscillates passed the neutral axis to its maximum point, the scaffold continues to bend and concave downwards due to the driving force of the media within the chamber, the potential continues towards its maximum positive potential. Finally, when the speaker returns back to the neutral state, the scaffold also returns back to the neutral position, thus the potential is zero again. There is a residual potential peaks due to continuous water movement within the chamber following a speaker oscillation.

The effect of various fiber diameters and thicknesses of electrospun PVDF-TrFE scaffolds were measured for potential generation under a range of strains. When measuring the effects of fiber diameter on potential generation, as expected, as the fiber diameter increases, the voltage output decreases. Fiber diameter is significantly affected by polymer concentration. It becomes more difficult to elongate and stretch a polymer solution with higher polymer concentration due to the high viscosity and stronger macromolecular chain entanglement (Shenoy, S. L., et al., *Role of chain entanglements on fiber formation during electrospinning of polymer solutions: good solvent, non-specific polymer-polymer interaction limit*. Polymer, 2005. 46(10): p. 3372-3384). Therefore, the β crystal phase content decreases with increasing fiber diameter, ultimately, leading to lower voltage production.

On the other hand, as the fiber mat thickness increased, an increase in voltage output was observed. Due to the capacitive nature of a PVDF nanofiber mat, as the fiber mat thickness increased, there is a greater charge separation, hence a greater output voltage. However, increasing the mat thickness could also decreased the amount the scaffold could strain, negatively affecting the performance of the piezoelectric scaffold.

Previous studies have shown that cell alignment for greater neurite outgrowth of neural cell types requires a certain minimum fiber size (Yang, F., et al., *Electrospinning of nano/micro scale poly (L-lactic acid) aligned fibers and their potential in neural tissue engineering*. Biomaterials, 2005. 26(15): p. 2603-2610; and Wang, H. B., et al., *Varying the diameter of aligned electrospun fibers alters neurite outgrowth and Schwann cell migration*. Acta biomaterialia, 2010. 6(8): p. 2970-2978). Neural cell types preferentially grows on larger fiber sizes, which would compromise the performance of the piezoelectric scaffold. Electrospun fiber morphology and scaffold thickness will collectively influence charge separation on the piezoelectric scaffold surface while the fiber diameter is the predominant factor affecting cellular alignment. Therefore, the scaffolding system needs to be optimized to balance the potential generation of PVDF-TrFE electrospun scaffolds with topographical cue to guide cellular alignment.

We demonstrated the ability to generate potentials from PVDF-TrFE scaffolds by non-contact mechanical stimulation using the developed cell culture system. We were able to precisely control the potential generation by controlling the fiber diameter and scaffold thickness via the electrospinning technique. This piezoelectric cell culture system allows us to generate electrical potentials by non-contact mechanical activation to stimulate neural cells for modulating their behaviors.

Example 2

Electrical Stimulation of Neuronal Cells Via Mechano-Responsive Piezoelectric Scaffolds Enhances their Functional Gain Through Neurite Elongation An estimated 20 million people in the US suffer from some form of peripheral neuropathy, a condition resulting from damage to the peripheral nervous system, by disease or injury. Due to the complex nature of nerve regeneration, full functional recovery is difficult to achieve, especially for large nerve gaps. Therefore, there is an increasing need for strategies to enhance nerve regeneration for full functional recovery. Electrical stimulation has been shown to facilitate the promotion of axon regrowth and induce the secretion of neurotrophic factors from glial cells to further enhance the axon regeneration process. We demonstrate the use of non-contact electrical stimulation using a biocompatible, piezoelectric polyvinylidene fluoride trifluoroethanol (PVDF-TrFE) by taking advantage of its piezoelectric properties to enhance neurite elongation of the neuronal PC12 cells. Under mechanical/electrical stimulation for 96 hr PC12 cells elongated their neurites up to an average of 100 μm and with 60% of the cell population possessing elongated neurites as compared to 72 μm and 20%, respectively for the statically cultured cells. Of this population of cells, 40% possessed neurites that were 6 to 7 times longer than the nucleus body. These results demonstrate the usage of piezoelectric materials to their full capacity provides the capacity for nerve regeneration of severe nerve damage with large gaps.

Despite the advancement of surgical procedures and strategies, complete functional recovery of severe damage to the peripheral nerve, caused by traumatic injury or disease, is rarely achieved due to inherently poor regenerative capabilities of neural system, especially for large nerve gaps (Schmidt, C. E. and J. B. Leach, Neural tissue engineering: strategies for repair and regeneration. Annual review of biomedical engineering, 2003. 5(1): p. 293-347). The process of nerve regeneration requires a series of well-orchestrated steps including Wallerian degeneration of axon and re-mapping of nerve connection from the proximal nerve stump into the distal muscle targets. The success of this process is significantly impacted by pre-treatment duration, patient's age, and distance of injury to target tissue. Especially, the size of injured nerve gap is an important factor, determining the efficacy of nerve regeneration. A large defect gap size of 30 mm or greater may cause diversion of axon regrowth into inappropriate areas and/or uncontrollable branching which ultimately may fail to reinnervate the proper target tissue.

To repair nerve gaps sizes that are 30 mm or larger, the current gold standard in the clinical setting is surgically removing a less used nerve, i.e., the sural nerve, the greater auricular nerve, or the medial antebrachial cutaneous nerve, from the patient and utilizing it as an autologous nerve graft (Millesi, H., Bridging defects: autologous nerve grafts. How to improve the results of peripheral nerve surgery, 2007: p. 37-38). Because it is acquired from the patient, it has no immune-responsive and possibility of rejection; it provides the biological cues ideal for cells to infiltrate the injury site, proliferate, and perform axon regeneration; and it is structurally stable and can withstand physiological stress. However, sacrificing the donor nerves typically lead to donor site morbidity, including loss of sensory function, prolonged operative and recovery times, and the invasiveness of multiple surgeries. The autologous nerve graft also poses other limitations, such as differences in nerve trunk size and limited length. In this regard, non-biological nerve conduits have been developed to guide nerve regeneration, but current clinically-approved natural and synthetic conduits are typically biologically inert and cannot fully repair transected nerves to regain full functionality.

Recently, electrical stimulation has gained attention as a potent regenerative signal to modulate electro-responsiveness of neural cells for the auto-regulation of neurotropic factors to enhance nerve regeneration (Shepherd, R. K., A. Coco, and S. B. Epp, Neurotrophins and electrical stimulation for protection and repair of spiral ganglion neurons following sensorineural hearing loss. Hearing research, 2008. 242(1): p. 100-109; Gartner, A. and V. Staiger, Neurotrophin secretion from hippocampal neurons evoked by long-term-potentiation-inducing electrical stimulation patterns. Proceedings of the National Academy of Sciences, 2002. 99(9): p. 6386-6391; and English, A. W., et al., Electrical stimulation promotes peripheral axon regeneration by enhanced neuronal neurotrophin signaling. Developmental neurobiology, 2007. 67(2): p. 158-172). Specifically, studies demonstrated that bioelectric fields that induce local surface electrical charges, enhance nerve regeneration by inducing the secretion of various growth factors from neural cells to promote nerve fiber outgrowth (Schmidt, C. E., et al., Stimulation of neurite outgrowth using an electrically conducting polymer. Proceedings of the National Academy of Sciences, 1997. 94(17): p. 8948-8953; Zhang, Z., et al., Electrically conductive biodegradable polymer composite for nerve regeneration: electricity-stimulated neurite outgrowth and axon regeneration. Artificial Organs, 2007. 31(1): p. 13-22; and Thompson, B. C., et al., Conducting polymers, dual neurotrophins and pulsed electrical stimulation—dramatic effects on neurite outgrowth. Journal of Controlled Release, 2010. 141(2): p. 161-167). In in vitro studies, electrical stimulation has shown to excite neurons to upregulate the release of several neurotrophic factors, such as brain-derived nerve factor (BDNF), NT4/5, and trkB, for nerve regeneration (Gartner, A. and V. Staiger, Neurotrophin secretion from hippocampal neurons evoked by long-term-potentiation-inducing electrical stimulation patterns. Proceedings of the National Academy of Sciences, 2002. 99(9): p. 6386-6391; and Nagappan, G. and B. Lu, Activity-dependent modulation of the BDNF receptor TrkB: mechanisms and implications. Trends in neurosciences, 2005. 28(9): p. 464-471). It has also shown to stimulate ion flow in the plasma membrane of Schwann cells to induce the production of neurotrophins, nerve growth factor (NGF) and BDNF (Huang, J., et al., Electrical stimulation induces calcium-dependent release of NGF from cultured Schwann cells. Glia, 2010. 58(5): p. 622-631; and Koppes, A. N., et al., Electrical stimulation of Schwann cells promotes sustained increases in neurite outgrowth. Tissue Engineering Part A, 2013. 20(3-4): p. 494-506). Despite its promising potential for stimulating nerve regrowth, the application of electrostimulation has been limited in clinical settings due to its invasive nature and small effective area to apply electrical charges.

In this regard, piezoelectric materials provide an effective modality for non-contact electrical neuromodulation. By the direct piezoelectric effect, a mechanical strain on the electroactive materials induces electrical charge separation on the surface (Vijaya, M., Piezoelectric materials and devices: applications in engineering and medical sciences2012: CRC Press).

There were several attempts to utilize biocompatible poly(vinylidene fluoride) (PVDF) or its derivatives including P(VDF-trifluoroethanol) (PVDF-TrFE), an organic piezoelectric polymer, for nerve regeneration in vitro as well as in vivo. PVDF has been shown to enhance neurite outgrowth of neuronal cells in vitro (Lee, Y.-S., G. Collins, and T. L. Arinzeh, Neurite extension of primary neurons on electrospun piezoelectric scaffolds. Acta biomaterialia, 2011. 7(11): p. 3877-3886). In vivo, implanted PVDF-TrFE conduits demonstrated the ability to bridge short nerve gaps to regain partial functionality (Fine, E. G., et al., Improved nerve regeneration through piezoelectric vinylidenefluoride-trifluoroethylene copolymer guidance channels. Biomaterials, 1991. 12(8): p. 775-780). Although those studies showed some favorable phenomenological observations from the use of PVDF-TrFE, a lack of systematic piezoelectric characterization and its utilization for the material's design limited the realization of its full potential.

In this study, PVDF-TrFE nanofibrous scaffolds were synthesized by electrospinning to determine their potential for nerve regeneration. The optimization of piezoelectric scaffolds such as fiber size, scaffold thickness, and the magnitude of mechanical perturbation for piezoelectric activation was systematically approached to maximize the regenerative responses of a neuronal cell line. We demonstrated the capability of non-contact mechanical/electrical stimulation on neuronal cells cultured on electrospun PVDF-TrFE scaffolds to induce nerve regeneration via neurite elongation.

Synthesis and Morphological Characterization of PVDF-TrFE Nanofibrous Scaffolds

PVDF-TrFE (Solvay, Belgium) was dissolved at various concentrations in different solvent systems to produce a range of different electrospun fiber diameters, as described in Example 1. Briefly, a 16 wt. % PVDF-TrFE (70:30 mol %) was dissolved in a 60/40 volume ratio of N,N-dimethylformamide (DMF, Sigma Aldrich, St. Louis, MO) to methyl ethyl ketone (MEK, Sigma Aldrich) solvent system. 11.5 wt. % and 7 wt. % PVDF-TrFE were dissolved in a 60/40 volume ratio of DMF to acetone solvent system, with the addition of 1 wt. % pyridinium formate (PF) buffer (Sigma Aldrich). The solutions were magnetically stirred at 1200 rpm for 3 hr at room temperature. The PVDF-TrFE solutions were individually electrospun using a grounded rotating mandrel to produce aligned fibers. The thickness of the fiber mat was controlled by adjusting the deposition time. A comprehensive table including the electrospinning parameters can be found in Table 2.2. To further enhance the piezoelectric properties of PVDF-TrFE, the electrospun fiber mats were subjected to annealing at 90° C. for 24 hr. The fiber morphology, diameter and alignment were characterized using scanning electron microscopy (SEM, Vega3, Tescan, Pleasanton, CA). The fibers were sputter-coated with gold to visualize under SEM. Using the ImageJ software, at least 100 individual fibers were assessed to determine the average fiber diameter and alignment.

Cell Culture Chamber for Mechanical/Electrical Stimulation

Figure 17:
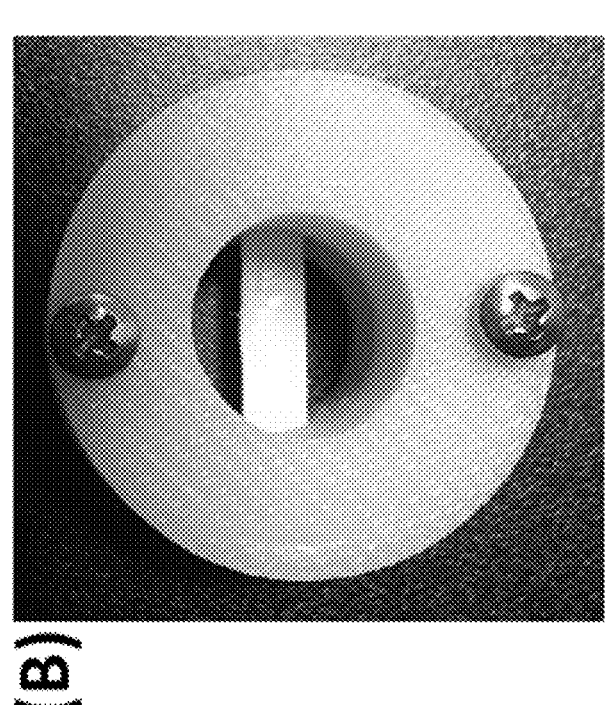
FIG. 17. Piezoelectric cell culture system. (A) A schematic of the expanded cell culture system. (B) A photograph of an assembled cell culture device with a PVDF-TrFE aligned scaffold.

A piezoelectric cell culture system was fabricated to apply non-contact mechanical/electrical stimulation to the nanofibrous PVDF-TrFE scaffold/cell constructs by a vertical actuation stage as described in detail in Example 1 (FIG. 17). The chamber was designed to fit into a standard 6-well tissue culture plate. Briefly, the top and bottom casings were 3D-printed with acrylonitrile butadiene styrene (ABS). When assembled, the PVDF scaffold is securely held by the silicone o-rings. Stainless steel screws hold the two casings together. The center cavity provides an area to hold media while allowing free deflection of the cell/scaffold construct under vertical actuation. The exposed area of the cell/scaffold construct has the dimensions of 15 mm×5 mm.

Piezoelectric Characterization of Electrospun Nanofibers

To quantify the potential generation of the PVDF-TrFE scaffolds in the actuation system, acellular scaffolds were subjected to mechanical/electrical stimulation inside the cell culture system. PVDF-TrFE scaffolds were cut to the dimensions of 45 mm by 5 mm with various thicknesses. Gold electrodes with the dimension 40 mm by 4 mm were sputtered on both sides of the scaffolds. A hydrophobic poly(styrene-b-isobutylene-b-stryrene) (SIBS, Sibstar, Kaneka, Pasadena, TX) coating was spray coated on top of gold sputtered surfaces to prevent an electrical short circuit.

The processed scaffold was assembled into the cell culture chamber and 2 mL of DI water was added. The chamber was placed on the vertical actuator and various magnitudes of strains were applied at 3 Hz while simultaneously measuring resultant potential generation by an oscilloscope (Pico Technologies, St. Neots, UK). The peak to peak output voltage was determined for 200, 500, and 800 nm fiber diameter at various scaffold thicknesses. The magnitude of applied strain was determined from images captured during the deflection of scaffolds under various magnitudes of actuation.

PC12 Cell Culture

PC12 cells, a rat adrenal pheochromocytoma cell line, were purchased from ATCC (Manassas, VA). The cells were maintained on tissue culture plates coated with type I collagen from rat tail (Sigma Aldrich) in F12K medium (ATCC), supplemented with 15% horse serum (Sigma Aldrich), 2.5% fetal bovine serum (FBS, VWR, Radnor, NJ), and 1% antimycotic/antibiotic solution (Corning, Corning, NY). To pre-differentiate the PC12 cells, the cells were detached from the surface by a cell scraper. To disintegrate cell clumps, the cells were passed through a 22 G needle several times. The cells were then seeded onto tissue culture plates at a density of 30,000 cells/cm2 in starvation differentiation media (F12K medium supplemented with 1% FBS and 1% antimycotic/antibiotic solution). The cells were allowed to adhere for 6 hr, followed by the supplementation of the media with 50 ng/mL nerve growth factor (2.5S) (Corning). The cells were allowed to pre-differentiate for 48 hr before detaching by mechanical scraping for subsequent cell seeding on the scaffolds.

The Effects of Scaffold Morphological and Electrical Stimulation on Cellular Behaviors To determine the effects of PVDF-TrFE fiber diameter on neurite elongation, pre-differentiated PC12 cells were separately seeded onto PVDF-TrFE scaffolds with fiber diameters of 200, 500, or 800 nm at a density of 40,000 cells/cm$^2$. The cells were cultured for 96 hours, before fixation in 4% paraformaldehyde (PFA) for the morphological analysis as described below.

To determine the effects of the various magnitudes of applied potential regimen, pre-differentiated PC12 cells on the PVDF-TrFE scaffolds having an average fiber diameter of 500 nm were electrically stimulated without mechanical perturbation. The cell/scaffold construct was placed on a conductive surface to apply an electric field with respect to the thickness of the construct (FIG. 17 (A)). Gold-coated polystyrene were cut out to the dimensions of 15 mm×5 mm and adhered to a tissue culture plate. A PVDF-TrFE scaffold with the same dimensions was glued to the surface of the polystyrene. A hole was drilled through the tissue culture plate to expose the conductive polystyrene to make electrical connection to a function generator. A grounded gold-coated coverslip was placed 5 mm above the gold-coated polystyrene. A function generator was utilized to control the electrical impulses applied to the conductive surface at 100, 200, and 400 mVp-p, with its shape similar to potential peaks generated from piezoelectrically actuated PVDF-TrFE scaffolds. The cell culture plates for this electrical stimulation were sterilized by ethanol and UV treatment of 30 min and 1 hr, respectively. The pre-differentiated cells by NGF treatment for 48 hr were detached and reseeded onto the PVDF-TrFE scaffolds at the density of 40,000 cells/cm$^2$. The cells were allowed to attach for 24 hr prior to being subjected to electrical stimulation. The PC12 cells were either electrically stimulated once for 2 hr, followed by 72 hr of static culture or daily stimulated for 2 hr for three days.

For both conditions, the cells were cultured in a total duration of 96 hrs before fixation in 4% paraformaldehyde (PFA).

The Effects of Mechanical/Electrical Stimulation on Cellular Behaviors

Once the optimal scaffold fiber diameter and applied potential regimen were determined as described above, the differentiated PC12 cells were subjected to mechanical/electrical stimulation on PVDF-TrFE by using the vertical actuation stage. The scaffolds with the dimensions of 45 mm×5 mm were treated with 20% FBS for 12 hr before cell seeding to enhance the adhesion of PC12 cells to the scaffolds. A hydrophobic SIBS coating was applied to leave an area of 10 mm×5 mm to confine cell culture space. The scaffolds were assembled into the sterile chamber individually and the pre-differentiated cells were seeded onto the scaffolds at a density of 40,000 cells/cm$^2$. The seeded cells were allowed to attach for 2 hrs before filling up the chamber with additional media. The cells were cultured for 24 hrs before subjecting them to mechanical/electrical stimulation. Similarly to the method used for determining potential generation of acellular PVDF-TrFE scaffolds, the cell-seeded scaffold was actuated by the vertical actuation stage to produce the optimum potential determined in the electrical stimulation study as previously described. The cell/scaffold constructs were either stimulated once for 2 hrs followed by 72 hrs of static culture or daily stimulated for 2 hrs for three days. For both conditions, the cells were cultured in a total duration of 96 hrs before fixation in 4% PFA.

Morphological Characterization of PC12 Cells

To visualize the elongation of neurites, the fixed cells were immune-stained with beta III-tubulin (Thermo Fisher), and counter-stained the nucleus with 4',6-Diamidino-2-Phenylindole (DAPI, Vector Labs, Burlingame, CA) nucleus and actin with Alexa Fluor 488-Phalloidin (Invitrogen, Carlsbad, CA). By imaging analysis using the ImageJ, neurite length, percentage of cell population bearing neurites, and the percentage of neurite-bearing cells possessing neurite lengths, within a certain range, greater than the nuclei length were quantitatively determined for both electrical and mechanical/electrical stimulation studies.

Statistical Analysis

Statistical analysis was performed with at least three biologically independent samples, and represented as an average±standard deviation (SD) or standard error of mean (SEM) as indicated. The data were subjected to ANOVA with Tukey's post-hoc test using the SPSS software (IBM) to determine statistical significance (p<0.05).

Effects of Nanofibrous Piezoelectric PVDF-TrFE on Neurite Elongation

Figure 18:
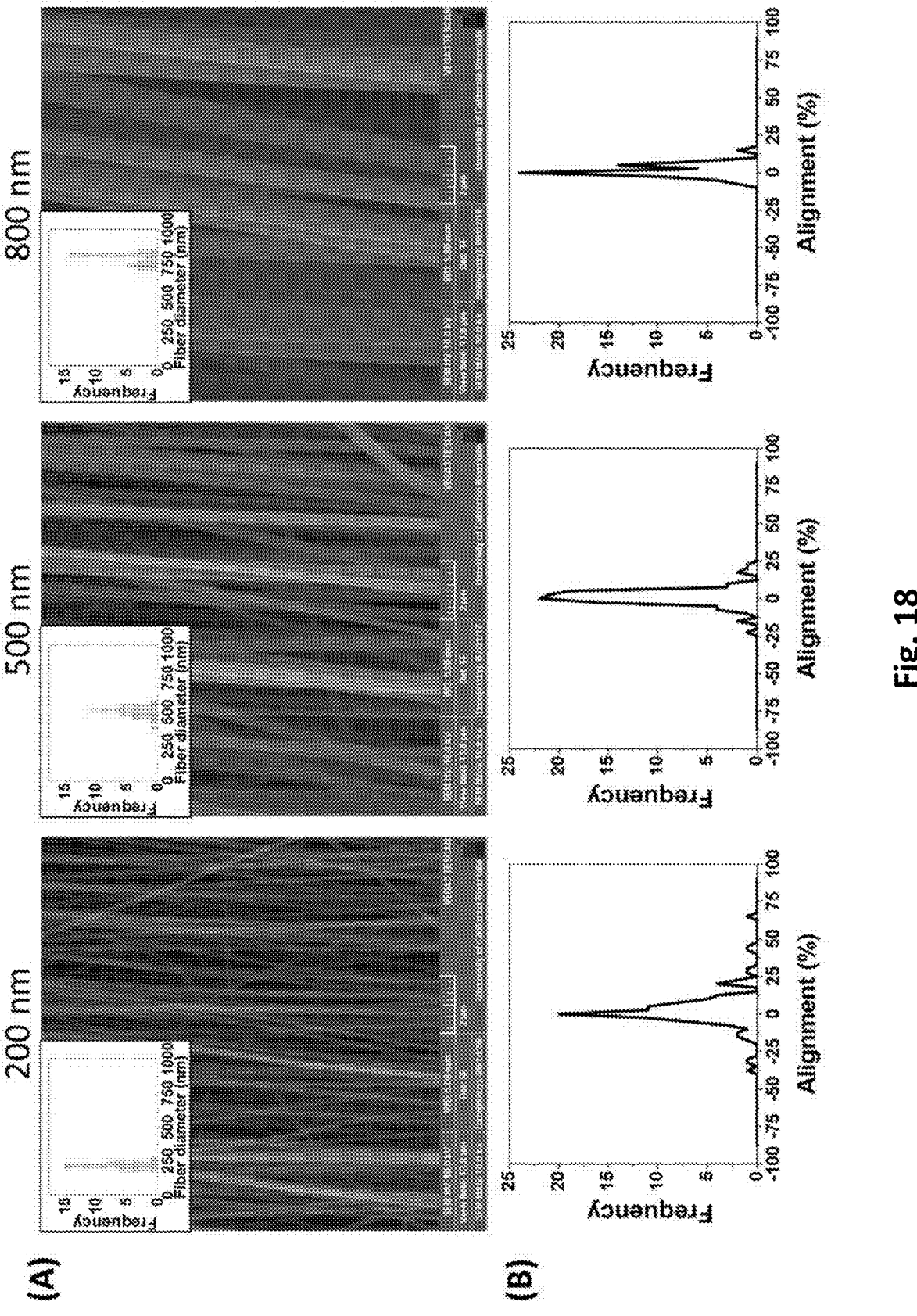
FIG. 18. Morphological characterization of electrospun PVDF-TrFE aligned nanofibers. (A) SEM images of PVDF-TrFE aligned nanofibers with various average fiber diameters (inset: fiber diameter histogram). (B) Fiber alignment histograms of PVDF-TrFE aligned nanofibers with various fiber diameter.

The fiber diameter of electrospun scaffolds has been shown to significantly affect the alignment of neuronal cells, thus the neurite elongation. In addition, we have shown that the fiber diameter of electrospun PVDF determines the piezoelectric performance of the scaffolds as smaller fiber diameters exponentially enhance the piezoelectric constant. To optimize fiber diameter that achieves a balance between high piezoelectric properties while promoting the elongation of neurites, PVDF was electrospun to produce three distinctly different fiber diameters. Various electrospinning conditions including solution properties (solvent system, polymer concentration, additives), processing parameters (solution flow rate, spinneret-to-collector distance), and environmental conditions (temperature and humidity) were optimized to reproducibly produce an average fiber diameter of 200, 500, or 800 nm (FIG. 18 (A)). These scaffolds were morphologically characterized for their fiber diameter and alignment using SEM (FIG. 18 (A)). Larger fiber diameter enhanced alignment, but all scaffolds exhibited relatively high fiber alignment within 200 of the neutral axis (FIG. 18 (B)).

Figure 19:
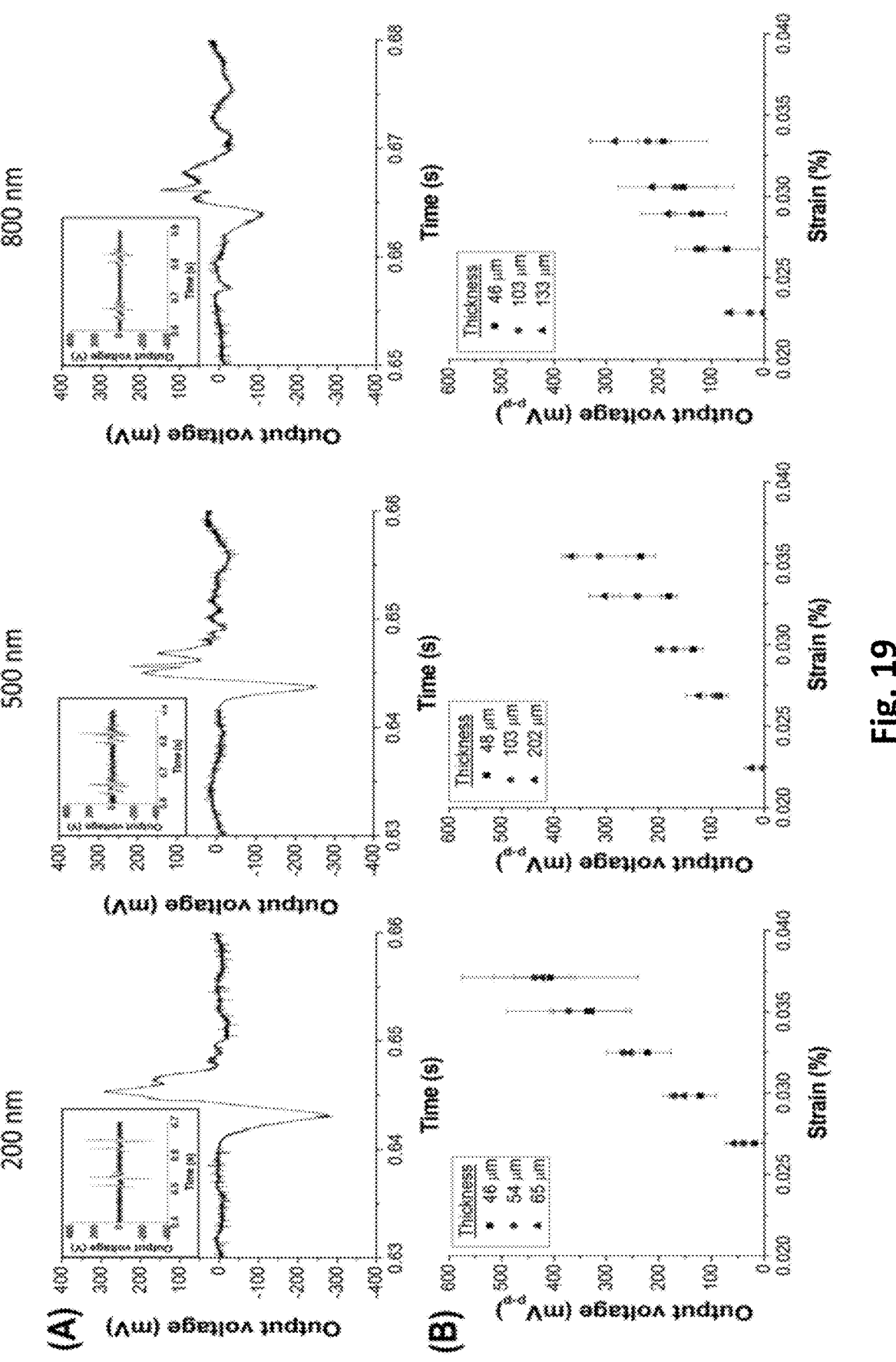
FIG. 19. Piezoelectric characterization of PVDF-TrFE scaffolds having various fiber diameters and scaffold thicknesses. (A) The characteristic voltage response of PVDF-TrFE nanofibers with fiber diameters of 200, 500, and 800 nm and a fiber mat thickness of ~50 $\mu$m at the strain values of: 200 nm=0.037%, 500 nm=0.035%, 800 nm=0.033%. The inset represents the recording of several peaks. (B) The relationship between the applied strain and output voltage when subjected to mechanical perturbation.

The fiber size-dependent piezoelectric performance of the electrospun PVDF scaffolds was determined by subjecting the samples to the vertical actuator at 3 Hz (FIG. 19). The mechanical perturbation of the scaffolds generated electric potentials exhibiting the characteristic piezoelectric double peaks during each oscillation (up and down translational motion of the chamber). As expected from our previous study demonstrating the fiber size-dependency of piezoelectric constants in electrospun PVDF-TrFE, the smallest fiber diameter scaffolds generated the highest output voltage. Furthermore, the potential generation increased as the scaffold thickness increased for all fiber sizes. These results provided a means to tune the morphological properties of the scaffolds (i.e., fiber diameter and scaffold thickness) accordingly for designed piezoelectric performance in the subsequent experiments.

Figure 20:
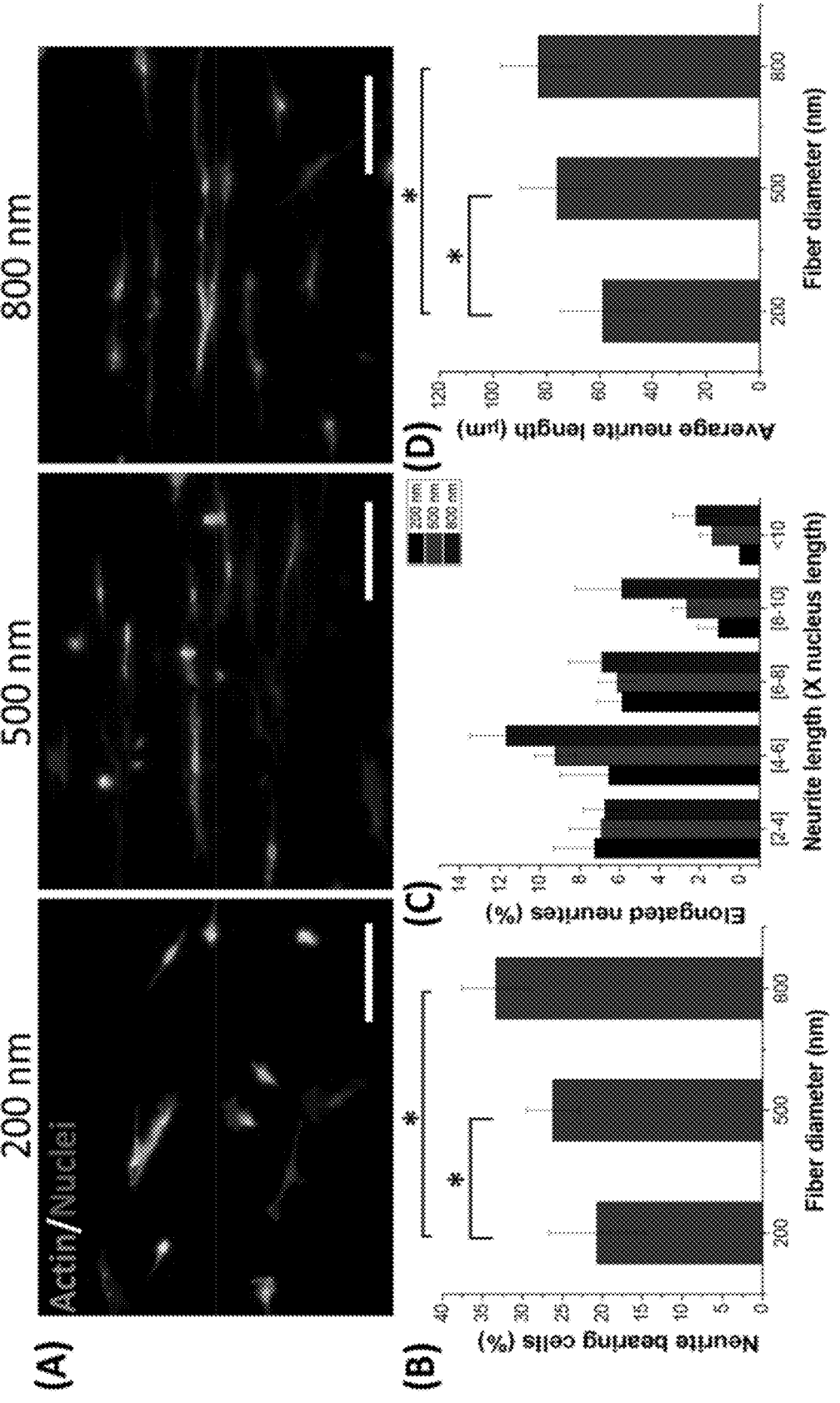
FIG. 20. Effects of different fiber diameter on neurite formation and elongation. (A) Representative immunofluorescence images showing actin morphology of PC12 cells cultured on 200, 500, and 800 nm fiber diameter. Quantifi-

We next examined the effects of fiber diameter on neuronal cell behaviors as the direction of neurite elongation is guided by the combination of fiber diameter and alignment (FIG. 20). PC12 cells exhibited greater directionality on the scaffolds with larger fiber diameters that likely prevented spreading of the cells across adjacent fibers. The greater alignment of the cells on larger fiber diameters appears to positively affect neurite formation and its elongation. The average neurite length of the cells cultured on scaffolds with 800 nm fiber diameter was approximately 81 μm. The average number of neurites per cells was also greater in the cells on the scaffolds with larger fiber diameters (FIG. 20, B). The larger fiber diameter also induced a greater number of the cells to possess neurites longer than 4 times of the nucleus size (FIG. 20, D). To balance the better piezoelectric performance of the smaller fiber and the greater neuronal cell behaviors on the larger fiber, the scaffolds with an average fiber diameter of 500 nm were utilized for the remainder of the experiments.

Effects of Electrical Stimulation on Neurite Elongation

To determine the optimal electric potential to promote neurite elongation in PC12 cells, the cells were subjected to different magnitudes of electric fields (FIG. 21 (A)). To take into account the contribution from scaffold morphology on cellular behaviors, the cells were cultured on electrospun PVDF with an average fiber diameter of 500 nm and during electrical stimulation. A peak-to-peak electric potential of 100, 200, or 400 mV at 3 Hz, with a wave form similar to piezoelectric potential generation shown in FIG. 21, was applied to the cells. Cellular responses were quantified by imaging analysis (FIG. 21). As the magnitude of electrical stimulation increased from 0 (control) to 200 mVp-p, PC12 cells increased neurite formation and elongation. However, a high magnitude of 400 mVp-p resulted in a significant decline neurite length due to cell death. The multi-day application of both 100 and 200 mVp-p, induced a greater percentage of PC12 cells that possessed neurites as well as promoted greater neurite elongation. Lastly, multi-day stimulation induced the greatest number of cells that possess neurites in the range of 6-10 times longer than the nucleus body.

Effects of Mechanical/Electrical Stimulation on Neurite Elongation

From the previous results, the thickness of PVDF-TrFE scaffold with an average fiber diameter of 500 nm was optimized to produce 200 mVp-p under mechanical perturbation. Pre-differentiated PC12 cells were seeded on these scaffolds and stabilized for 24 hr before the mechanical/electrical stimulation in the cell culture system. Based on the electrical stimulation study, a multi-day mechanical/electrical stimulation regimen was selected and carried out for 96 hr. Cellular responses were quantified by imaging analysis (FIG. 22). Both mechanical/electrical stimulation conditions enhanced neurite formation and elongation as compared to static culture. At the end of the culture duration, mechanical/electrical stimulation condition induced the greatest number of neurite-formed cells with its average length greater 6 to 8 times greater than their nucleus body. These results demonstrate that electrical activity from the PVDF-TrFE induced neurite formation and promoted elongation parallel to the direction of the fiber mat.

Electrical stimulation has been shown to facilitate nerve regeneration by enhancing the secretion of neurotrophic factors from glial cells to support axon regeneration and/or directly promoting neurite elongation (Huang, J., et al., Electrical stimulation induces calcium-dependent release of NGF from cultured Schwann cells. Glia, 2010. 58(5): p. 622-631; You, S., et al., The expression of the low affinity nerve growth factor receptor in long-term denervated Schwann cells. Glia, 1997. 20(2): p. 87-100; and Fields, R. D., E. A. Neale, and P. G. Nelson, Effects of patterned electrical activity on neurite outgrowth from mouse sensory neurons. Journal of Neuroscience, 1990. 10(9): p. 2950-2964). Several in vivo studies demonstrated the efficacy of electrical stimulation promoting nerve outgrowth in rat models of nerve injury (Kadekaro, M., A. M. Crane, and L. Sokoloff, Differential effects of electrical stimulation of sciatic nerve on metabolic activity in spinal cord and dorsal root ganglion in the rat. Proceedings of the National Academy of Sciences, 1985. 82(17): p. 6010-6013; Al-Majed, A. A., et al., Brief electrical stimulation promotes the speed and accuracy of motor axonal regeneration. Journal of Neuroscience, 2000. 20(7): p. 2602-2608; and Nowak, L. and J. Bullier, Axons, but not cell bodies, are activated by electrical stimulation in cortical gray matter I. Evidence from chronaxie measurements. Experimental brain research, 1998. 118(4): p. 477-488). The first human clinical trial showed a promising potential of therapeutic electrical stimulation, where improved post-surgical outcomes were achieved by localized low frequency of electrical stimulation on patients with their median nerve compressed in the carpal tunnel causing loss of functional nerve-muscle contracts (Gordon, T., et al., Brief post-surgical electrical stimulation accelerates axon regeneration and muscle reinnervation without affecting the functional measures in carpal tunnel syndrome patients. Experimental neurology, 2010. 223(1): p. 192-202). Despite these positive outcomes, the application of electrical stimulation in the clinical setting is limited by several factors; its invasive nature requires the implantation of exposed electrodes. Furthermore, the electrode approach can activate neuron(s) only in direct contact with or close proximity to the electrodes, resulting in a small localized effective area. To address these issues, various methodologies have been developed to globally deliver electrical stimulation to a severed nerve using a continuous graft connecting the nerve gap.

Conductive nerve guidance conduits provide an opportunity to implement electrical stimulation as a means to guide the regeneration and regrowth of axons while reducing the infiltration of fibrous tissue. Several in vitro studies demonstrated enhanced neurite elongation of neuronal cells under electrical stimulation via conductive polymer scaffolds (Schmidt, C. E., et al., Stimulation of neurite outgrowth using an electrically conducting polymer. Proceedings of the National Academy of Sciences, 1997. 94(17): p. 8948-8953; Zhang, Z., et al., Electrically conductive biodegradable polymer composite for nerve regeneration: electricity-stimulated neurite outgrowth and axon regeneration. Artificial Organs, 2007. 31(1): p. 13-22; Gomez, N. and C. E. Schmidt, Nerve growth factor-immobilized polypyrrole: Bioactive electrically conducting polymer for enhanced neurite extension. Journal of biomedical materials research Part A, 2007. 81(1): p. 135-149; and Kotwal, A. and C. E. Schmidt, Electrical stimulation alters protein adsorption and nerve cell interactions with electrically conducting biomaterials. Biomaterials, 2001. 22(10): p. 1055-1064). In vivo, Xu et al. recently showed enhanced functionality of regenerated nerve using a PPy-PDLLA conduit in a rat sciatic nerve transection model, where a higher density of thick myelin sheaths of the cells in the PPy-PDLLA conduit was observed as compared to an autograft (Xu, H., et al., Conductive PPY/PDLLA conduit for peripheral nerve regeneration. Biomaterials, 2014. 35(1): p. 225-235). These studies collectively suggest a great potential of electrical stimulation to drive nerve regeneration, but it requires the use of implanted electrodes for clinical applications.

In this regard, piezoelectric materials provide a means to non-invasively induce electrical potentials. Especially, PVDF and its derivatives including PVDF-TrFE have been utilized for such applications due to their excellent biocompatibility and relatively high piezoelectricity for polymers. Early evidence of the implantation of poled PVDF conduits compared to unpoled conduits demonstration the feasibility of piezoelectric materials to enhance partial axon regeneration with myelination (Aebischer, P., et al., Piezoelectric guidance channels enhance regeneration in the mouse sciatic nerve after axotomy. Brain research, 1987. 436(1): p. 165-168). Recently, Lee et al. exploited the enhanced piezoelectricity of PVDF-TrFE scaffolds synthesized by electrospinning to accelerate neurite outgrowth of dorsal root ganglion neurons or promote neural differentiation of human neural stem/progenitor cells (Lee, Y.-S., G. Collins, and T. L. Arinzeh, Neurite extension of primary neurons on electrospun piezoelectric scaffolds. Acta biomaterialia, 2011. 7(11): p. 3877-3886; and Lee, Y.-S. and T. L. Arinzeh, The influence of piezoelectric scaffolds on neural differentiation of human neural stem/progenitor cells. Tissue Engineering Part A, 2012. 18(19-20): p. 2063-2072). However, these studies were likely unable to utilize the true potential of piezoelectricity as it requires dynamic straining of the materials to generate electrical potential. Although they attributed the enhancement in cellular behaviors to piezoelectric responses of the PVDF fibers developed by cell exerting forces, they would be likely due to surface charges of the fibers (Saltzman, W. M. and T. R. Kyriakides, Cell interactions with polymers. Principles of tissue engineering, 2000. 2).

In contrast, we optimized piezoelectric properties of PVDF-TrFE with a systematic approach and thorough material characterization, to generate the appropriate electric potential of 200 mVp-p to stimulate neuronal cells by non-contact mechanical perturbation of electrospun PVDF-TrFE scaffolds. A recent study showed the novel use of aligned conductive polymer PLLA-graphene oxide scaffolds to induce PC12 cell neurite length of 90 μm in 6 days. With our optimized PVDF-TrFE scaffolds, we demonstrated that PC12 cells exposed to multi-day mechanical/electrical stimulation exhibited significantly enhanced neurite formation of 100 μm in merely three days of stimulation and 60% of the population possessed neurites. This signifies the potency of external piezoelectric stimulus for nerve regeneration. Furthermore, considering the relatively porous structure of electrospun PVDF-TrFE scaffolds that allow for selective diffusion of macromolecules and neurotrophic factors, our results demonstrate the promising potential of PVDF-TrFE to enhance nerve regeneration.

In the present study, we demonstrated that mechanical/electrical stimulation was effective in enhancing neuronal cell elongation. Under multi-day application of mechanical/electrical stimulation for 96 hr produced an average neurite length of approximately 100 μm with 60% of the cell population possessing elongated neurites as compared to 72 μm and 20%, respectively for the statically cultured cells. Of this population of cells, 40% possessed neurites that were 6 to 7 times longer than the nucleus body. These results exemplify the potential of utilizing non-contact electrical stimulation induced by PVDF-TrFE for enhancing neuronal activities for the application of nerve regeneration.

Example 3

Mechanical/Electrical Stimulation Enhances Glial Cell Functionality

Glial cells of the peripheral and central nervous system play an essential role in the process of axon regeneration when the nerve is injured. When a peripheral nerve is damaged, Schwann cells, the glial cell type of the peripheral nervous system, are responsible for clearing necrotic axon and myelin debri, secreting neurotrophic factors to induce axon regrowth, and myelinate the regenerated axon. Following injury of a central nerve, neural stem cells differentiate into oligodendrocytes and astrocytes, the glial cell types of the central nervous system, to remyelinate the axon and for glial scar tissue which possess supportive factors for axon regrowth, respectively. Electrical stimulation has been widely investigated for its use to enhance nerve regeneration due to the innate electrical nature of the nervous system. Specifically, electrical stimulation has shown to enhance the functionality of glial cells. In this study, we demonstrated the capability of subjecting electrical stimulation by non-contact mechanical/electrical stimulation of aligned electrospun PVDF-TrFE scaffolds to induce the maturation of functional glial cells from the PNS and CNS. Mechanical/electrical stimulation induced Schwann cells of the PNS produced NGF for enhancing axon regrowth. Alternatively, mechanical/electrical stimulation induced differentiation of NSCs toward myelin-secreting oligodendrocytes and axon permissive factor-producing astrocytes.

Injury to the peripheral and central nervous systems often leads to minimal or permanent loss of motor and sensory functions. It is debilitating and significantly decreases an individual's quality of life. Functional recovery depends of the capacity of axon regeneration following neural damage, whether it be from a traumatic injury or disease. The peripheral nervous system (PNS) is naturally more capable of axon repair than the central nervous system (CNS) after injury as a result of its own promoting cellular, environmental, and intrinsic factors (FIG. 23) (Huebner, E. A. and S. M. Strittmatter, *Axon regeneration in the peripheral and central nervous systems, in Cell Biology of the Axon* 2009, Springer. p. 305-360). Specifically, the behaviors of glial cells, such as Schwann cells in the PNS, and oligodendrocytes and astrocytes of the CNS, play an important role in the regeneration process (Sjöstrand, J., *Proliferative changes in glial cells during nerve regeneration.* Cell and Tissue Research, 1965. 68(4): p. 481-493; and Fu, S. Y. and T. Gordon, *The cellular and molecular basis of peripheral nerve regeneration*. Molecular neurobiology, 1997. 14(1-2): p. 67-116).

When the PNS is damaged and axons are transected, a process known as Wallerian degeneration occurs and the distal axon stump degenerates to the target tissue (Faweett, J. and R. J. Keynes, *Peripheral nerve regeneration*. Annual review of neuroscience, 1990. 13(1): p. 43-60). Native Schwann cells, the glial cell of the PNS, dedifferentiate and convert into a repair Schwann cells phenotype to create and enhance a permissive environment to facilitate axon regeneration. These reprogrammed cells are responsible for the upregulation of neurotrophic factors, including nerve growth factor (NGF), elevation of pro-inflammatory (IL-1β and TNFα) and anti-inflammatory (IL-4 and IL-10) cytokines, recruitment of macrophages and additional Schwann cells for myelin breakdown and clearance, and formation of regeneration pathway for directing axons towards their target tissue (Dubový, P., I. Klusáková, and I. Hradilová Svíženskã, *Inflammatory Profiling of Schwann Cells in Contact with Growing Axons Distal to Nerve Injury*. BioMed Research International, 2014. 2014: p. 691041; and Frostick, S. P., Q. Yin, and G. J. Kemp, *Schwann cells, neurotrophic factors, and peripheral nerve regeneration*. Microsurgery, 1998. 18(7): p. 397-405).

In contrast, when a CNS axon is damaged, i.e. spinal cord injury or traumatic brain injury, it does not spontaneous regenerate due to its prohibitive inflammatory environment (Homer, P. J. and F. H. Gage, *Regenerating the damaged central nervous system*. Nature, 2000. 407(6807): p. 963). In response to an injury, adult neural stem cells in the white matter of the spinal cord differentiate into oligodendrocytes and astrocytes (Sabelström, H., M. Stenudd, and J. Frisén, *Neural stem cells in the adult spinal cord*. Experimental neurology, 2014. 260: p. 44-49). The differentiated mature myelinating oligodendrocytes, a glial cell type of the CNS, quickly remyelinates axons and secrete metabolic factors to maintain CNS neurons. However, reactive astrocytes form glial scars that create a physical barrier, inhibiting axon regeneration (Faulkner, J. R., et al., *Reactive astrocytes protect tissue and preserve function after spinal cord injury*. Journal of Neuroscience, 2004. 24(9): p. 2143-2155). It was originally believed that the formation of glial scar tissue was the major inhibitory factor for regeneration following CNS injury. However, it has been recently demonstrated that regeneration cannot occur in the absence of glial scar formation (Anderson, M. A., et al., *Astrocyte scar formation aids CNS axon regeneration*. Nature, 2016. 532(7598): p. 195). In fact, scar-forming astrocytes upregulate growth supportive factors, CSPG4 and CSPG5, that promote axon regrowth. Therefore, it is advantageous to modulate the cellular activities of both myelinating oligodendrocytes and extracellular matrix-producing astrocytes to promote nerve regeneration across severe CNS injuries.

Applied electric fields have been demonstrated to accelerate nerve regeneration in both PNS (Kems, J., et al., *Electrical stimulation of nerve regeneration in the rat: the early effects evaluated by a vibrating probe and electron microscopy*. Neuroscience, 1991. 40(1): p. 93-107; Asensio-Pinilla, E., et al., *Electrical stimulation combined with exercise increase axonal regeneration after peripheral nerve injury*. Experimental neurology, 2009. 219(1): p. 258-265. 121; and Lu, M.-C., et al., *Effects of electrical stimulation at different frequencies on regeneration of transected peripheral nerve*. Neurorehabilitation and neural repair, 2008. 22(4): p. 367-373) and CNS (Baldessarini, R. J. and I. J. Kopin, *The effect of drugs on the release of norepinephrine-*

*H3 from central nervous system tissues by electrical stimulation in vitro*. Journal of Pharmacology and Experimental Therapeutics, 1967. 156(1): p. 31-38; Udina, E., et al., *Electrical stimulation of intact peripheral sensory axons in rats promotes outgrowth of their central projections*. Experimental neurology, 2008. 210(1): p. 238-247; and Ranck, J. B., *Which elements are excited in electrical stimulation of mammalian central nervous system: a review*. Brain research, 1975. 98(3): p. 417-440). In particular, glial cells have been shown to respond to electrical cues by activation of voltage-gated ion channels (Verkhratsky, A. and H. Kettenmann, *Calcium signalling in glial cells*. Trends in neurosciences, 1996. 19(8): p. 346-352; and Sontheimer, H., *Voltage-dependent ion channels in glial cells*. Glia, 1994. 11(2): p. 156-172). In Schwann cells, electrical stimulation induces calcium influx through T-type voltage-gated calcium channels and subsequently enhances nerve growth factor (NGF) production, a neurotrophic protein essential for axon growth (Huang, J., et al., *Electrical stimulation induces calcium-dependent release of NGF from cultured Schwann cells*. Glia, 2010. 58(5): p. 622-631). Electrical stimulation can also modulate neural stem cell behavior to differentiate towards the two glial cell types in the CNS, oligodendrocytes and astrocytes, as well as neurons (Kam, N. W. S., E. Jan, and N. A. Kotov, *Electrical stimulation of neural stem cells mediated by humanized carbon nanotube composite made with extracellular matrix protein*. Nano letters, 2008. 9(1): p. 273-278; and Park, S. Y., et al., *Enhanced differentiation of human neural stem cells into neurons on graphene*. Advanced materials, 2011. 23(36)). Despite its promising potential for stimulating glial cell differentiation and functionality, the application of electrical stimulation has been limited in clinical settings due to its invasive implantation of electrodes and limited stimulation area.

In this regard, piezoelectric materials can be utilized as a non-contact electrical stimulation platform for glial cell differentiation. When the piezoelectric material is subjected to mechanical stress, an electric charge is generated at the surface of the material (Vijaya, M., *Piezoelectric materials and devices: applications in engineering and medical sciences* 2012: CRC Press). Poly(vinylidene fluoride) (PVDF) and its derivatives including P(VDF-trifluoroethanol) (PVDF-TrFE), biocompatible piezoelectric polymer, have been explored as a platform for nerve regeneration, including the stimulating Schwann cells to secrete neurotrophic factors, inducing differentiation of neural stem cells, and promoting neurite elongation of dorsal root ganglia (Ribeiro, C., et al., *Piezoelectric polymers as biomaterials for tissue engineering applications*. Colloids and Surfaces B: Biointerfaces, 2015. 136: p. 46-55; Lee, Y.-S. and T. L. Arinzeh, *The influence of piezoelectric scaffolds on neural differentiation of human neural stem/progenitor cells*. Tissue Engineering Part A, 2012. 18(19-20): p. 2063-2072; and Lee, Y.-S., G. Collins, and T. L. Arinzeh, *Neurite extension of primary neurons on electrospun piezoelectric scaffolds*. Acta biomaterialia, 2011. 7(11): p. 3877-3886). However, due to the lack of systematic piezoelectric characterization and limited mechanistic understandings, the full potential of the piezoelectric polymer is yet to be explored.

We utilized PVDF-TrFE nanofibrous scaffolds to determine their potential for enhancing glial cell differentiation and functionality. Schwann cells and neural stem cells were subjected to mechanical/electrical stimulation and their changes behaviors were observed by assessing changes in gene and protein expression. We demonstrated the anabolic activities of mechanical/electrical stimulation to promote the functionalization of Schwann cells to mature myelinating cells and the differentiation of neural stem cells to oligo-dendrocytes and astrocytes for potential enhancement of nerve regeneration.

Synthesis and Morphological Characterization of PVDF-TrFE Nanofibrous Scaffolds 11.5 wt. % PVDF-TrFE (Solvay, Belgium) was dissolved in a 60/40 volume ratio of dimethylformamide (DMF, Sigma Aldrich, St. Louis, MO) to acetone (Sigma Aldrich) solvent system, with the addition of 1 wt. % pyridinium formate (PF) buffer (Sigma Aldrich). The solution was magnetically stirred at 1200 rpm for 3 hr at room temperature. A high voltage source was utilized to apply −18.4 kV to charge the solution dispensing through a 22 G needle at 6 ml/hr and elongate the fluid jet across a 10 cm needle tip to grounded collector distance. Finally, the fluid jet was collected onto a high speed grounded mandrel rotating at 47.9 m/s to produce aligned fibers. The fibers were collected for 4 hr to produce a 200 μm thick scaffold. Lastly, the electrospun fiber mats were subjected to annealing at 90° C. for 24 hr to further enhance the piezoelectric properties of PVDF-TrFE.

Cell Culture for Mechanical/Electrical Stimulation

A custom cell culture system was utilized to apply non-contact mechanical/electrical stimulation to the cell-seeded electrospun PVDF-TrFE scaffolds by a translational actuation stage. PVDF-TrFE scaffolds were cut into 45 mm×5 mm strips. A hydrophobic SIBS coating was applied to leave an area of 15 mm×5 mm to confine the cell culture space. The cell culture chamber and PVDF-TrFE strips were sterilized separately in 70% ethanol for 1 hr. The cell culture chamber was dried overnight drying to remove any ethanol vapor. The PVDF-TrFE strips were washed in PBS before assembling into the dried, sterile chamber.

Immortalized rat neuronal Schwann cells (RSC96) were purchased from ATCC (Manassas, VA). They were cultured in high glucose Dulbecco's Modified Eagle Medium (DMEM, Lonza, Morristown, NJ), supplemented with 10% fetal bovine serum (FBS, VWR, Radnor, NJ) and 1% penicillin/streptomycin (Mediatech, Manassas, VA) and maintained in a standard 37° C. incubator with 5% CO2. Medium was replaced every 2-3 days and once it reached 70-80% confluency the cells were detached using 0.25% Trypsin/EDTA (Life Technologies, Carlsbad, CA) for 3 min at 37° C. The RSC96 were seeded onto the PVDF-TrFE scaffold assembled in the cell culture chamber at 5,000 cells/cm2 and allowed to attach for 2 h prior to filling the cell culture chamber. During the experiment, the cells were maintained in the maintenance media with no additional growth factors.

Alternatively, C17.2 neural stem cells (NSCs), derived from the cerebellum of neonatal mouse, were cultured in high glucose DMEM, supplemented with 10% FBS (Sigma Aldrich, St Louis, MO), 5% horse serum (Gibco, Gaithersburg, MD), 1% sodium pyruvate (Gibco), and 1% penicillin/streptomycin in a standard 37° C. incubator with 5% CO2. The cells were cultured up to 70-80% confluency and medium was replaced every 2-3 days. Once the cells reached confluency, the cells were incubated in 0.05% trypsin EDTA/PBS for 2 min at 37° C. The NSCs were seeded onto the sterile PVDF-TrFE scaffolds assembled in the cell culture chamber at 5,000 cells/cm2 and the cells were allowed to attach for 2 hours before filling up the chamber with additional media. During the experiment, the cells were maintained in the maintenance media with no additional growth factors.

The cells seeded on the PVDF-TrFE scaffolds were cultured for 24 hr before subjecting them to mechanical/electrical stimulation. The cell-seeded scaffold was vertically actuated on the vertical oscillation stage to apply a surface strain of approximately 0.03%, which was determined to generate 200 mVp-p for a 200 μm thick PVDF-TrFE scaffold when oscillating at 3 Hz. The cell/scaffold constructs were either stimulated daily for 2 hr for seven days. As a control, cells were cultured in the cell culture system statically as well as on tissue culture plates for the same duration. At the conclusion of the experiment, cells were subjected to lysis buffer for gene expression analysis or 4% paraformaldehyde (PFA) for protein expression analysis.

Protein Expression Analysis

To determine if mechanical/electrical stimulation induced the production of NGF by RSC96, NGF receptors on the cells were stained with anti-NGF (Santa Cruz Biotechnology, Dallas, TX) as the primary antibody and with Alexa Fluor-594 (Jackson ImmunoResearch, West Grove, PA) as the secondary antibody. The samples were subsequently counter-stained with 4',6-Diamidino-2-Phenylindole (DAPI, Vector Laboratories, Burlingame, CA) for nuclei and Alexa Fluor-488 Phalloidin (Invitrogen, Carlsbad, CA) for actin.

To characterize the phenotypic changes to NSCs that occurred during mechanical/electrical stimulation, the cells were immuno-stained with primary antibodies for markers of either NSCs (Nestin, DSHB, Iowa City, IA), neurons (βIII tubulin, Thermo Fisher Scientific, Waltham, MA), oligodendrocytes (O4, R&D Systems, Minneapolis, MN), or astrocytes (GFAP, Santa Cruz Biotechnology) with the appropriate secondary antibody Alexa Fluor-488. The samples were counter-stained with DAPI and Alexa Fluor-594 followed by analysis using immunofluorescence microscopy. The ImageJ software was utilized to determine the fluorescence intensity of each protein of interest.

Gene Expression Analysis

The effects of mechanical/electrical stimulation on RSC96 and NSCs, gene expression after 7 days of mechanical/electrical stimulation were determined at the gene level by real-time polymerase chain reaction (RT-PCR). Total RNA was extracted using an RNeasy Micro Kit (Qiagen, Valencia, CA), and cDNA synthesis was performed using iScript cDNA Synthesis Kit (Bio-Rad, Hercules, CA) according to manufacturers' protocols. Real-time PCR was performed to determine the gene expression of myelinating factors of rat RSC96s (Table 3) and phenotypic markers for mouse NSCs (Table 4). Data were analyzed by the comparative threshold cycle (CT) method using Rps18 for RSC96s and Gapdh for NSCs as an endogenous control.

TABLE 3

| | Primer sets for rat RSC96 used for rt-PCR analysis | | | | |
|---|---|---|---|---|---|
| Primer | Forward | SEQ ID No. | Reverse | SEQ ID No. | |
| Rps18 | 5'-CCCGAGAAGTTTCAGCACATC-3' | 1 | 5'-ATGGCAGTGATAGCGAAGGCT-3' | 6 | |
| Ngf | 5'-TTCCAGGCCCATGGTACAAT-3' | 2 | 5'-AAACTCCCCCATGTGGAAGAC-3' | 7 | |

TABLE 3-continued

| Primer sets for rat RSC96 used for rt-PCR analysis | | | | |
|---|---|---|---|---|
| Primer | Forward | SEQ ID No. | Reverse | SEQ ID No. |
| Krox20 | 5'-TGCGCCTAGAAACCAGACCTT-3' | 3 | 5'-ATGCCCGCACTCACAATATTG-3' | 8 |
| Pmp22 | 5'-TGTACCACATCCGCCTTGG-3' | 4 | 5'-GAGCTGGCAGAAGAACAGGAAC-3' | 9 |
| Ncam-1 | 5'-TGGAACGCCGAGTACGAAGTA-3' | 5 | 5'-TGAACACGAAGTGAGCTGCCT-3' | 10 |

TABLE 4

| Primer sets for mouse NSCs used for rt-PCR analysis. | | | | | |
|---|---|---|---|---|---|
| Marker | Primer | Forward | SEQ ID No | Reverse | SEQ ID No. |
| Housekeeping | Gapdh | 5'-GGCAAATTCAACGGCACAGT-3' | 11 | 5'-TCGCTCCTGGAAGATGGTGAT-3' | 24 |
| NSC | Nestin | 5'-GCGCTGGAACAGAGATTGGAA-3' | 12 | 5'-TGGTATCCCAAGGAAATGCAG-3' | 25 |
| | Msi1 | 5'-GATGCCATGCTGATGTTCGAC-3' | 13 | 5'-ATGTCCTCGCTCTCAAACGTG-3' | 26 |
| | Sox2 | 5'-TTTTGTCCGAGACCGAGAAGC-3' | 14 | 5'-CATGAGCGTCTTGGTTTTCCG-3' | 27 |
| Neuron | Tubb3 | 5'-ACCTTGTGTCTGCCACCATGA-3' | 15 | 5'-CACCATGTTCACAGCCAGCTT-3' | 28 |
| | Map2 | 5'-AAGCCATTGTGTCCGAACCA-3' | 16 | 5'-GAGCGGAAGAGCAGTTTGTCA-3' | 29 |
| | Eno2 | 5'-ATCGCCACATTGCTCAGCTAG-3' | 17 | 5'-TGAGAGCCACCATTGATCACA-3' | 30 |
| Oligodendrocyte | Olig1 | 5'-ACGCCAAAGAGGAACAGCA-3' | 18 | 5'-TCCATGGCCAAGTTCAGGT-3' | 31 |
| | Cldn11 | 5'-TGGCATCATCGTCACAACGT-3' | 19 | 5'-CCCAGTTCGTCCATTTTTCG-3' | 32 |
| | Mog | 5'-TGCCCTGCTGGAAGATAACAC-3' | 20 | 5'-TGCAGCCAGTTGTAGCAGATG-3' | 33 |
| Astrocyte | Gfap | 5'-TGGAGCTCAATGACCGCTTT-3' | 21 | 5'-GCTCGAAGCTGGTTCAGTTCA-3' | 34 |
| | Cspg4 | 5'-CTGAGCAATCTGTCTTTCCCAGT-3' | 22 | 5'-TGTGTATGCAGAGGTTCAAGCCT-3' | 35 |
| | Ntf3 | 5'-TCACCACGGAGGAAACGCTAT-3' | 23 | 5'-TCAATGGCTGAGGACTTGTCG-3' | 36 |

Statistical Analysis

Statistical analysis was performed with at least three biologically independent samples, and represented as an average±standard deviation (SD) or standard error of mean (SEM) as indicated. The data were subjected to ANOVA with Tukey's post-hoc test using the SPSS software (IBM) to determine statistical significance ($p < 0.05$).

Effects of Non-Contact Mechanical/Electrical Stimulation on RSC96

Based on our previous study, the solution and electrospinning parameters were optimized to produce 200 μm thick scaffold of uniform cylindrical structures with a fiber diameter of 500 nm and 90% alignment within 200 deviation. RSC96 cells, a rat Schwann cell line, were seeded on the piezoelectric scaffolds and subjected to a dynamic strain regimen to produce approximately 200 Vp-p, which has shown to enhance neuronal functions. The effects of mechanical/electrical stimulation by PVDF-TrFE on the cells were was determined by immunocytochemistry (FIG. 24) and real-time polymerase chain reaction (rt-PCR) (FIG. 25). RSC96 cells cultured statically on the scaffolds and on tissue culture plastics served as controls. Under the static condition on the scaffolds, the cells grew in colonies, similar to those cultured on tissue culture plates. In contrast, mechanical/electrical stimulation induced more single cell formation (FIG. 24 (A)). Coincidently, the expression of NGF by RSC96 was significantly greater in the mechanical/electrical stimulation condition as compared to statically cultured cells on PVDF-TrFE (FIG. 24 (B)). Furthermore, the application of mechanical/electrical stimulation induced a significant upregulation in gene expression of pro-myelinating Schwann cell markers, NGF, Krox20, and PMP22, while there was suppression of the immature Schwann cell marker, NCAM-1 (FIG. 25).

Effects of Mechanical/Electrical Stimulation on NSCs

To determine the effects of mechanical/electrical stimulation on the phenotypic fate of NSC, changes in protein and gene expression by immunocytochemistry (FIGS. 26, 28, 30 and 32) and rt-PCR (FIGS. 27, 29, 31 and 33), respectively, were analyzed. At the protein level, expression of Nestin, a NSC marker, is prevalent in both static and piezoelectric conditions, indicating there are still naïve undifferentiated cells differentiating (FIG. 26). It is also observed that the NSC maintained its typical round morphology. Although both mechanical/electrical stimulation and static condition expressed the neuronal marker, βIII tubulin, as well as having an elongated cellular morphology characteristic of neurons, 0 there is greater intensity of expression in the stimulated condition. Interestingly, the expression of oligodendrocyte marker, O4, and astrocyte marker, GFAP, were only observed in the mechanical/electrical stimulation conditions. Relative changes in gene expression for the maintenance of NSC phenotype or for differentiation towards the three neural cell types of the CNS was analyzed by rt-PCR. There was a downregulation of NSC genes in both static and mechanical/electrical stimulation conditions, indicating the on-going differentiation of cells (FIG. 27), while there was a downregulation in the immature neuron marker, Tubb3, but an upregulation of mature neuron marker, Map2 and Eno2, under mechanical/electrical stimulation. This gene expression agrees with the observation of greater expression of βIII tubulin at the protein level. As expected from the immunocytochemistry results, mechanical/electrical stimulation induced a significant upregulation in gene expression for both oligodendrocyte (Olig1, Cldn11, and Mog) and astrocyte (Gfap, Cspg4, and Ntf3) markers, signifying the capability of mechanical/electrical stimulation to differentiate NSCs into glial cell types.

We demonstrated that mechanical/electrical stimulation was effective in modulating glial cell behavior. In Schwann cells (RSC96), a glial cell type in the PNS, mechanical/electrical stimulation enhanced the production of a neurotrophic factor, NGF. In NSCs, mechanical/electrical stimulation induced the differentiation towards oligodendrocytes and astrocytes, glial cell phenotypes of the CNS, required for nerve regeneration.

A peak-to-peak voltage of 200 mV produced by PVDF-TrFE at 3 Hz, 2 hr per day for 7 days resulted in changes in gene and protein expression of myelinating markers and neurotrophin secretion in Schwann cells. Nerve growth factor (NGF), early growth response 2 (Krox20), and peripheral myelin protein 22 (PMP22) are markers that indicate myelination of Schwann cells (Wu, Y., et al., *Electroactive biodegradable polyurethane significantly enhanced Schwann cells myelin gene expression and neurotrophin secretion for peripheral nerve tissue engineering*. Biomaterials, 2016. 87: p. 18-31; and Chew, S. Y., et al., *The effect of the alignment of electrospun fibrous scaffolds on Schwann cell maturation*. Biomaterials, 2008. 29(6): p. 653-661). In contrast, NCAM-1 is expressed in immature Schwann cells during development. When Schwann cells convert into their myelinating phenotype, a downregulation of NCAM-1 is observed, while an upregulation of NGF, Krox20, and PMP22 occurs. Schwann cells have been shown to respond to electrical cues due to activation of voltage-gated calcium channels (Huang, J., et al., *Electrical regulation of Schwann cells using conductive polypyrrole/chitosan polymers*. Journal of biomedical materials research Part A, 2010. 93(1): p. 164-174). Calcium ions have been demonstrated to regulate many electrical stimulation-induced intracellular events, including its important role in regulating neurotrophin expression (Verkhratsky, A. and H. Kettenmann, *Calcium signalling in glial cells*. Trends in neurosciences, 1996. 19(8): p. 346-352; Huang, J., et al., *Electrical stimulation induces calcium-dependent release of NGF from cultured Schwann cells*. Glia, 2010. 58(5): p. 622-631; and Sher, E., et al., *Physiopathology of neuronal voltage-operated calcium channels*. The FASEB Journal, 1991. 5(12): p. 2677-2683). Specifically, NGF production in Schwann cells has been shown to require both an influx of calcium across the plasma membrane as well as calcium immobilization from internal calcium reservoirs (Huang, J., et al., *Electrical stimulation induces calcium-dependent release of NGF from cultured Schwann cells*. Glia, 2010. 58(5): p. 622-631; and Lev-Ram, V. and M. Ellisman, *Axonal activation-induced calcium transients in myelinating Schwann cells, sources, and mechanisms*. Journal of Neuroscience, 1995. 15(4): p. 2628-2637). Both of these events can occur when the Schwann cells are exposed to electrical stimulation.

Neural stem cells predominately exist in the white matter of the spinal cord within the CNS (Dulin, J. N. and P. Lu, *Bridging the injured spinal cord with neural stem cells*. Neural regeneration research, 2014. 9(3): p. 229). Their phenotypic fate is glial cells, mainly oligodendrocytes and astrocytes. At the onset of CNS pathological diseases or injuries, NSCs are activated and differentiate into myelinating oligodendrocyte and astrocytes (Sabelström, H., M. Stenudd, and J. Frisén, *Neural stem cells in the adult spinal cord*. Experimental neurology, 2014. 260: p. 44-49). Neuronal activity, i.e., action potential propagation, is also important for inducing this transformation of NSC to myelinating oligodendrocytes and astrocytes for axon regrowth. These newly differentiated cells migrate to the location of the injury site and begin responding damaged tissue. The oligodendrocytes begin to remyelinate the damaged axon, while astrocytes begin to secrete inhibitory and permissive factors for glial scar formation.

Recent studies have demonstrated the capability of electrical stimulation to induce NSC differentiation (Kam, N. W. S., E. Jan, and N. A. Kotov, *Electrical stimulation of neural stem cells mediated by humanized carbon nanotube composite made with extracellular matrix protein*. Nano letters, 2008. 9(1): p. 273-278; Pires, F., et al., *Neural stem cell differentiation by electrical stimulation using a cross-linked PEDOT substrate: expanding the use of biocompatible conjugated conductive polymers for neural tissue engineering*. Biochimica et Biophysica Acta (BBA)—General Subjects, 2015. 1850(6): p. 1158-1168; and Turner, J. T., *Human neural stem cell differentiation and electrical stimulation on a novel single walled carbon nanotube-polymer composite* 2013: Rutgers The State University of New Jersey-New Brunswick and University of Medicine and Dentistry of New Jersey). Due to the native electrical activities of neurons, NSC differentiation towards neurons has been widely studied (Yang, F., et al., *Electrospinning of nano/micro scale poly (L-lactic acid) aligned fibers and their potential in neural tissue engineering*. Biomaterials, 2005. 26(15): p. 2603-2610; Li, M., et al., *Neuronal differentiation of C17. 2 neural stem cells induced by a natural flavonoid, baicalin*. ChemBioChem, 2011. 12(3): p. 449-456; and Wang, Q., L. Yang, and Y. Wang, *Enhanced differentiation of neural stem cells to neurons and promotion of neurite outgrowth by oxygen-glucose deprivation*. International Journal of Developmental Neuroscience, 2015. 43: p. 50-57). Although the mechanism is not clear, electrical stimulation has been found to modulate signaling cascades that regulate calcium influxes which subsequently affects mitogenesis (Spitzer, N. C., *Electrical activity in early neuronal development*. Nature, 2006. 444(7120): p. 707). Biphasic electrical current has been demonstrated to induce the proliferation and differentiation of neural stem cells towards neuronal lineages (Chang, K.-A., et al., *Biphasic electrical currents stimulation promotes both proliferation and differentiation of fetal neural stem cells*. PLoS One, 2011. 6(4): p. e18738). Furthermore, electrical stimulation by conductive polymers have been utilized to differentiate NSC towards neurons with elongated neurites (Li, N., et al., *Three-dimensional graphene foam as a biocompatible and conductive scaffold for neural stem cells*. Scientific reports, 2013. 3: p. 1604). A similar differentiation of NSCs under mechanical/electrical stimulation was observed in this study, evident from the downregulation of NSC gene markers. Interestingly, βIII tubulin, a neuronal marker, was observed in both stimulated and static conditions. NSCs have been reported to respond to substrate morphology, enhancing differentiation towards neurons, due to their elongated nature (Leipzig, N. D. and M. S. Shoichet, *The effect of substrate stiffness on adult neural stem cell behavior*. Biomaterials, 2009. 30(36): p. 6867-6878; and Hu, J., et al., *Repair of extended peripheral nerve lesions in rhesus monkeys using acellular allogenic nerve grafts implanted with autologous mesenchymal stem cells*. Experimental neurology, 2007. 204(2): p. 658-666). By culturing the cells on aligned PVDF-TrFE was sufficient to induce the cells to differentiate towards neurons, as seen in the static condition. At the gene level, there was downregulation of Tubb3, a marker for immature neurons, in both mechanical/electrical stimulation and static conditions. However, there was an upregulation in Map2 and Eno2, both markers for mature neurons, only under mechanical/electrical stimulation, suggesting the functional maturation of the cells (Michibata, H., et al., *Inhibition of mouse GPM6A expression leads to decreased differentiation of neurons derived from mouse embryonic stem cells*. Stem cells and development, 2008. 17(4): p. 641-652).

Unlike neuronal differentiation of NSCs, their differentiation towards oligodendrocytes and astrocytes is less explored. In the present study, we observed an upregulation of oligodendrocyte and astrocyte markers when the NSCs were subjected to mechanical/electrical stimulation as compared the static control. At the protein level, mechanical/electrical stimulation was enough to induce expression of O4, an oligodendrocyte marker, and GFAP, an astrocyte marker, while there was no expression observed in the static conditions. At the gene level, an upregulation of Olig1, a marker for the maturation of oligodendrocytes, Cldn11, and Omg, both markers indicating myelination of oligodendrocytes (Yu, W.-P., et al., *Embryonic expression of myelin genes: evidence for a focal source of oligodendrocyte precursors in the ventricular zone of the neural tube*. Neuron, 1994. 12(6): p. 1353-1362). There was also a significant upregulation of Gfap, a filament marker of astrocytes, Cspg4, and Ntf3, both markers of secreted protein by astrocytes that promote axon regeneration (Anderson, M. A., et al., *Astrocyte scar formation aids CNS axon regeneration*. Nature, 2016. 532(7598): p. 195).

Mechanical/electrical stimulation may either directly or indirectly affect glial differentiation of NSC. Mechanical/electrical stimulation can directly affect neural stem cells by activating voltage-gated ion channels, specifically calcium ions, similarly to how the stimulation affects Schwann cells. Glial cells can also indirectly benefit from the activity of functional neurons activated by mechanical/electrical stimulation. Studies have shown that neuronal activity can drive oligodendrocyte progenitors to mature oligodendrocytes capable of remyelination of damaged nerves (Canoll, P. D., et al., *GGF/neuregulin is a neuronal signal that promotes the proliferation and survival and inhibits the differentiation of oligodendrocyte progenitors*. Neuron, 1996. 17(2): p. 229-243; and Emery, B., *Regulation of oligodendrocyte differentiation and myelination*. Science, 2010. 330(6005): p. 779-782). It has been demonstrated that active neurons initiate ATP signaling, which stimulates astrocytes to release promoting factors of axon regeneration, such as neuroglycans and neurotrophins. The contribution and decoupling of direct and indirect piezoelectric effects on the glial cell differentiation of NSCs need further controlled experimentation. Nevertheless, we demonstrated that mechanical/electrical stimulation provides a means to enhance the functionality of glial cells to promote nerve regeneration.

Due to their impact on nerve regeneration, strategies for enhancing glial cell functionality can improve methods for effective nerve repair. In this study, we successfully demonstrated the feasibility of non-contact mechanical/electrical stimulation by aligned electrospun PVDF-TrFE scaffolds to induce the maturation of functional glial cells from the PNS and CNS (FIG. 34). Mechanical/electrical stimulation induced Schwann cells of the PNS produced NGF for enhancing axon regrowth. Alternatively, mechanical/electrical stimulation induced differentiation of NSCs toward myelin-secreting oligodendrocytes and axon permissive factor-producing astrocytes.

We demonstrate a novel methodology enabling effective peripheral and central nerve regeneration by enhancing the functionality of neuronal and glial cells, as well as the differentiation of neural stem cells towards the three phenotypes of the CNS utilizing non-contact mechanical/electrical stimulation. Electrospinning technique to synthesize nanofibrous PVDF-TrFE, a biocompatible, piezoelectric polymer, allowed for precise control the fiber morphology (i.e., diameter), structure (i.e., uni-directional alignment), and dimensions (i.e., scaffold thickness) to ultimately modulate the piezoelectric performance, as well as neuronal cellular behaviors. We developed a piezoelectric cell culture system to subject neural cells to electric potentials generated from the nanofibrous PVDF-TrFE scaffolds by non-contact mechanical stimulation. This system was utilized to determine the effects of mechanical/electrical stimulation on neuronal, glial, and neural stem cell behaviors. When PC12 cells, a neuronal cell type, were subjected to mechanical/electrical stimulation, it enhanced the neurite growth in the direction of the fiber alignment and increased the population of neurite bearing cells as compared to a static control. Alternatively, mechanical/electrical stimulation induced the production of a neurotrophic factor, NGF, from Schwann cells, a PNS glial cell. As well as enhancing functionality of these neural cells, mechanical/electrical stimulation induced the differentiation of neural stem cells towards the three phenotypes of the central nervous system, including functionally active oligodendrocytes and astrocytes, CNS glial cells. Collectively, the induction of glial phenotype differentiation and the enhancement of their functionality are expected to facilitate nerve regeneration.

The functionality of the elongated neurites from PC12 cells or differentiated neurons from NSCs subjected to piezoelectrical stimulation may be assessed to determine the translational efficacy of the engineered tissues. For example, the multi-electrode array (MEA) technology can be used. The MEA can stimulate neural cells by transducing electrical currents by the ionic movement within the media. This ionic flux triggers the voltage-gate channels on the plasma membrane of the excitable cells to depolarize and induce an action potential. To record these electrical signal propagations, the electrodes on the MEA detect potential changes within the media by ions into electrical current.

Since we observed enhanced functional behavior of neuronal cells and Schwann cells by mechanical/electrical stimulation separately, a co-culture of the two cell types will determine if the piezoelectric cell culture system can enhance in vitro myelination by Schwann cells onto the existing neuronal cells. Myelin is an essential component of the PNS and CNS. Damages to the nerve by injuries/diseases has a detrimental effect on myelin. We can utilize this in vitro model can give us better understanding of the mechanism of myelination to potentially finding therapeutic interventions for treating demyelinating diseases by our piezoelectric culture system.

Mechanical/electrical stimulation may be induced by actuation of a vertical platform controlled by a subwoofer speaker. To have relevant translational usage, we may test the ability of external mechanical stimulation via a shockwave system to acoustically stimulate the piezoelectric neuroconduit to generate electrical potential through a medium similar to skin and muscle.

Ultimately, in vivo implantation of the neuroconduit will determine the efficacy of this piezoelectric material to facilitate neuronal and glial cell functionality to enhance the functional recovery of nerve damage with large gaps. This can be validated in a rat model by transecting a sciatic nerve to create a 15 mm gap. A hollow PVDF-TrFE conduit will be wrapped around the two nerve stumps and the application of shockwave pulses will be transmitted to the injury site. OCT technology may be used to monitor the elongation of axons within the tube as well as myelination of the axons.

Example 4

Mechano-electrical Stimulation for Functional Enhancement of Neural Cells Via Hydro-Acoustic Actuation of P(VDF-TrFE)

The development of humanized and/or patient-specific in vitro nerve models is expected to enhance our fundamental understanding in the pathogenesis of prevalent neurological diseases/disorders (B. J van der Star, D. Ys Vogel, M. Kipp, F. Puentes, D. Baker, S. Amor, *CNS & Neurological Disorders—Drug Targets* (*Formerly Current Drug Targets—CNS & Neurological Disorders*) 2012, 11, 570). This may lead to discovering efficient therapeutic interventions that are not often achievable with current animal models due to dissimilarities in genetics and metabolism as compared to human pathology (A. Denic, A. J. Johnson, A. J. Bieber, A. E. Warrington, M. Rodriguez, I. Pirko, *Pathophysiology* 2011, 18, 21). In addition, mechanical injury to nerves involving damage to- or abnormalities of neural structures over a threshold size, typically results in incomplete reinnervation due to inherently poor regenerative capabilities of the nervous system (S. L. Chen, et al., *Neural regeneration research* 2015, 10, 1777). One of the major challenges for both engineering in vitro neural tissues and enhancing in vivo nerve regeneration includes incorporating a potent stimulus to induce functional development of the tissue, which typical biochemical/pharmaceutical agents are not sufficient to render.

In this regard, electrical stimulation has gained attention as a potent regenerative signal to modulate the electro-responsiveness of neural cells, including the auto-regulation of neurotropic factors to enhance nerve regeneration (R. K. Shepherd, A. Coco, S. B. Epp, *Hearing research* 2008, 242, 100; A. Gärtner, V. Staiger, *Proceedings of the National Academy of Sciences* 2002, 99, 6386; and A. W. English, G. Schwartz, W. Meador, M. J. Sabatier, A. Mulligan, *Developmental neurobiology* 2007, 67, 158). Specifically, studies demonstrated that local surface electrical charges created by bioelectric fields induce the secretion of various growth factors from neural cells to promote nerve fiber outgrowth (A. Gartner, V. Staiger, *Proceedings of the National Academy of Sciences* 2002, 99, 6386; C. E. Schmidt, V. R. Shastri, J. P. Vacanti, R. Langer, *Proceedings of the National Academy of Sciences* 1997, 94, 8948; Z. Zhang, M. Rouabhia, Z. Wang, C. Roberge, G. Shi, P. Roche, J. Li, L. H. Dao, *Artificial Organs* 2007, 31, 13; B. C. Thompson, R. T. Richardson, S. E. Moulton, A. J. Evans, S. O'leary, G. M. Clark, G. G. Wallace, *Journal of Controlled Release* 2010, 141, 161; G. Nagappan, B. Lu, *Trends in neurosciences* 2005, 28, 464; A. Verkhratsky, H. Kettenmann, *Trends in neurosciences* 1996, 19, 346; H. Sontheimer, *Glia* 1994, 11, 156; and J. Huang, Z. Ye, X. Hu, L. Lu, Z. Luo, Glia 2010, 58, 622). In addition, electrical stimulation can modulate neural stem cell differentiation towards the two glial cell types in the CNS, oligodendrocytes and astrocytes, as well as neurons, important for nerve regeneration (N. W. S. Kam, E. Jan, N. A. Kotov, *Nano letters* 2008, 9, 273; and S. Y. Park, J. Park, S. H. Sim, M. G. Sung, K. S. Kim, B. H. Hong, S. Hong, *Advanced materials* 2011, 23). In vivo, applied electric fields have been demonstrated to accelerate nerve regeneration in both the peripheral nervous system (PNS) (J.

Kerns, A. Fakhouri, H. Weinrib, J. Freeman, *Neuroscience* 1991, 40, 93; E. Asensio-Pinilla, E. Udina, J. Jaramillo, X. Navarro, *Experimental neurology* 2009, 219, 258; and M.-C. Lu, C.-Y. Ho, S.-F. Hsu, H.-C. Lee, J.-H. Lin, C.-H. Yao, Y.-S. Chen, *Neurorehabilitation and neural repair* 2008, 22, 367) and central nervous system (CNS) (R. J. Baldessarini, I. J. Kopin, *Journal of Pharmacology and Experimental Therapeutics* 1967, 156, 31; E. Udina, M. Furey, S. Busch, J. Silver, T. Gordon, K. Fouad, *Experimental neurology* 2008, 210, 238; and J. B. Ranck, *Brain research* 1975, 98, 417). Due to their capability to apply electrical stimulation to neural cells, conductive materials, especially mechanical compliant polymers such as polyaniline, polypyrrole and polythiophene typically as a composite with other structural polymers, showed promising potential for functional neural tissue engineering and nerve regeneration (B. Guo, P. X. Ma, *Biomacromolecules* 2018, 19, 1764). However, the utilization of typical conductive materials for electrical stimulation in both in vitro and in vivo applications has several limitations. For example, the implementation of conductive materials can interfere with innate nerve signal transduction during in vitro experimentation or after in vivo regeneration. The use of electrodes is invasive, requiring wiring to a power source, and provides a small effective area, making it impractical for in vivo conditions.

Another physical stimulus, mechanical factor, has also shown to affect neural cell behaviors. The intracellular calcium levels, essential for regulating neuronal functions, are modulated by mechanical stimulation via stretch-activated ion channels (R. V. Sharma, M. W. Chapleau, G. Hajduczok, R. E. Wachtel, L. J. Waite, R. C. Bhalla, F. M. Abboud, *Neuroscience* 1995, 66, 433). For glial cells, the application of pulsed ultrasound promotes Schwann cell proliferation, resulting in accelerated peripheral nerve regeneration (W. Jiang, Y. Wang, J. Tang, J. Peng, Y. Wang, Q. Guo, Z. Guo, P. Li, B. Xiao, J. Zhang, *Scientific reports* 2016, 6, 22773). The differentiation of neural stem cells is also affected by their mechanical environment (K. Saha, A. J. Keung, E. F. Irwin, Y. Li, L. Little, D. V. Schaffer, K. E. Healy, *Biophysical journal* 2008, 95, 4426), further suggesting the important role of mechanical stimulation in neural tissue development/regeneration. Indeed, physical therapies as well as acupuncture have empirically shown to improve nerve regeneration (P. A. Armada-da-Silva, C. Pereira, S. Amado, A. P. Veloso, *International review of neurobiology* 2013, 109, 125; and G. H. He, J. W. Ruan, Y. S. Zeng, X. Zhou, Y. Ding, G. H. Zhou, *Neural regeneration research* 2015, 10, 128).

In this regard, piezoelectric materials, when activated by mechanical actuation, provide a means to electrically stimulate cells without interfering with innate signal transduction or necessitating an external power source. Piezoelectric materials generate surface potentials under dynamic mechanical strain while simultaneously remaining electrically insulating. There were several attempts to utilize biocompatible organic piezoelectric polymers, including poly(vinylidene fluoride) (PVDF) or its derivatives including poly(vinylidene fluoride-trifluoroethylene) (P(VDF-TrFE)), for nerve regeneration in vitro as well as in vivo. PVDF has been shown to promote neurite elongation of dorsal root ganglia cells, stimulate the secretion of neurotrophic factors from Schwann cells, and induce differentiation of neural stem cells towards neurons (Y. S. Lee, T. L. Arinzeh, *Tissue Eng Pt A* 2012, 18, 2063; Y.-S. Lee, G. Collins, T. L. Arinzeh, *Acta biomaterialia* 2011, 7, 3877; and C. Ribeiro, V. Sencadas, D. M. Correia, S. Lanceros-Mendez, *Colloid Surface B* 2015, 136, 46). In vivo, implanted P(VDF-TrFE) conduits demonstrated the ability to bridge short nerve gaps to regain partial functionality (P. Aebischer, R. F. Valentini, P. Dario, C. Domenici, P. M. Galletti, *Brain Res* 1987, 436, 165; and Y. S. Lee, S. L. Wu, T. L. Arinzeh, M. B. Bunge, *Biotechnol Bioeng* 2017, 114, 444). Although those studies showed some favorable phenomenological observations from the use of PVDF derivatives, a lack of systematic piezoelectric characterization and its utilization for the material's design may have limited the realization of its full potential.

Electrospun P(VDF-TrFE) nanofibers were employed as a cell culture scaffold for various neural progenitor cells including PC12 (neuron), RSC96 (Schwann), and mouse neural stem cells (NSCs) to demonstrate the regenerative effects of electrical stimulation, mechanical stimulation or the combination of both, derived from the mechanical activation of the piezoelectric material. We have shown the advantage of electrospinning in producing high performance piezoelectric polymers due to the technique's inherent electric biasing and mechanical stretching (G. Ico, A. Showalter, W. Bosze, S. C. Gott, B. S. Kim, M. P. Rao, N. V. Myung, J. Nam, *Journal of Materials Chemistry A* 2016, 4, 2293; and G. Ico, A. Myung, B. S. Kim, N. V. Myung, J. Nam, *Nanoscale* 2018, 10, 2894). Furthermore, electrospinning has the capability of producing a fibrous structure that can both resemble native ECM and be aligned to aid in unidirectional neuronal orientation as found in innate nerves. Based on the functional characterization of the piezoelectric scaffolds in a systematic manner, a cell culture system was engineered to deliver a mechanical stimulation, created by hydro-acoustic waves, to remotely activate the piezoelectric effect of these nanofibrous scaffolds, inducing a mechno-electrical stimulus on the cells to enhance their functionality and/or differentiation capacity.

We developed a piezoelectric material-based strategy to physically stimulate neural cells for their functional enhancement, potentially applicable for in vitro nerve tissue engineering and in vivo peripheral nerve regeneration. Piezoelectric materials have been used to enhance neural cell behaviors (Y. S. Lee, T. L. Arinzeh, Tissue Eng Pt A 2012, 18, 2063; Y.-S. Lee, G. Collins, T. L. Arinzeh, *Acta biomaterialia* 2011, 7, 3877; and C. Ribeiro, V. Sencadas, D. M. Correia, S. Lanceros-Mendez, *Colloid Surface B* 2015, 136, 46). However, these studies were likely unable to utilize the true potential of piezoelectricity as it requires dynamic straining of the materials to generate electric potentials. The biological application of piezoelectric materials, therefore, involves careful optimization of their properties that can be activated under physiologically safe magnitudes of mechanical actuation. In this study, electrospinning was utilized to synthesize nanofibrous scaffolds of PVDF derivatives, biocompatible piezoelectric polymers, to tune the optimal morphological and piezoelectric characteristics as cell culture scaffolds. As we have demonstrated, the fiber diameter of electrospun PVDF determines the piezoelectric performance of the nanofibers as smaller fiber diameters exponentially enhance the piezoelectric constant $d_{33}$ (G. Ico, A. Showalter, W. Bosze, S. C. Gott, B. S. Kim, M. P. Rao, N. V. Myung, J. Nam, *Journal of Materials Chemistry A* 2016, 4, 2293; and G. Ico, A. Myung, B. S. Kim, N. V. Myung, J. Nam, *Nanoscale* 2018, 10, 2894). However, the fiber diameter has also been shown to significantly affect cellular behaviors including the degree of neuronal cell alignment that promotes neurite formation/elongation in larger fibers by restricting cell spreading (G. T. Christopherson, H.-Q. Song H Fau-Mao, H. Q. Mao, *Biomaterials* 2009, 30, 556). To optimize the electrospun fiber diameter that achieves a balance between high piezoelectric properties while promoting the elongation of neurites, P(VDF-TrFE) was electrospun to produce three distinctly different fiber diameters. Various electrospinning conditions including solution properties (solvent system, polymer concentration, additives), processing parameters (solution flow rate, spinneret-to-collector distance), and environmental conditions (temperature and humidity) were optimized to reproducibly synthesize an average fiber diameter of 200, 500, or 800 nm (FIG. 35, a). Based on SEM image analysis, larger fiber diameter enhanced alignment, but all scaffolds exhibited relatively high fiber alignment within 200 of the neutral axis (FIG. 35, b). The fiber size-dependent piezoelectric performance of the electrospun PVDF scaffolds was determined by subjecting the samples to a vertical actuator at 3 Hz in an aqueous condition (FIG. 36). The mechanical perturbation of the scaffolds via hydro-acoustic stimulation, a maximum applied energy flux of $1.226 \times 10^{-4}$ mJ/mm² which is within physiologically safe levels, generated electric potentials exhibiting the characteristic piezoelectric double peaks during each oscillation (up and down translational motion of the chamber). As expected from our previous study demonstrating the fiber size-dependency of piezoelectric constants in electrospun P(VDF-TrFE) (G. Ico, A. Showalter, W. Bosze, S. C. Gott, B. S. Kim, M. P. Rao, N. V. Myung, J. Nam, *Journal of Materials Chemistry A* 2016, 4, 2293), the smallest fiber diameter scaffolds with a similar scaffold thickness generated the highest output voltage at a similar applied strain (FIG. 35, c). Furthermore, the potential generation increased as the scaffold thickness increased for all fiber sizes (FIG. 35, d). These results provide a means to tune the morphological properties of the scaffolds (i.e., fiber diameter and scaffold thickness) accordingly for designed piezoelectric performance in the subsequent experiments.

We next examined the effects of fiber diameter on neuronal cell behaviors as the neurite elongation is guided by the combination of fiber diameter and alignment. When statically cultured, PC12 cells, a rat neuronal cell line, exhibited greater alignment on the scaffolds with larger fiber diameters that likely prevented spreading of the cells across adjacent fibers. The greater alignment of the cells on larger fiber diameters positively affected neurite formation and elongation. The average neurite length of the cells cultured on scaffolds with 500 and 800 nm fiber diameter was approximately 76 and 81 μm, respectively, as compared to approximately 59 μm on 200 nm fiber scaffolds. The average number of neurites per cells was also greater in the cells cultured on the scaffolds with larger fiber diameters. To balance the better piezoelectric performance of the smaller fiber and the greater neuronal cell behaviors on the larger fiber, the scaffolds with an average fiber diameter of 500 nm were utilized for the remainder of the study.

In order to systematically analyze the contribution of scaffold-generated electric potentials, decoupled from the hydro-acoustic stimulation that was utilized to piezoelectrically activate the scaffolds on the cells, a heat-inactivated form of PVDF scaffold was synthesized. Electrospinning parameters were optimized to produce PVDF scaffolds with fiber diameter and alignment similar to those of P(VDF-TrFE) scaffolds (FIG. 37, a). Differential scanning calorimetry (DSC) was utilized to determine proper heat-treatment temperature for: 1) the piezoelectric enhancement of the P(VDF-TrFE) scaffolds and 2) the piezoelectric inactivation of the PVDF scaffolds. To enhance the piezoelectricity in the P(VDF-TrFE) fibers, a thermal treatment below the Curie temperature (114.9° C.) at 90° C. was carried out to promote the slight re-arrangement of the crystalline polarized domains without causing a full transition from the ferro- to para-electric phase (FIG. 37, b) (G. Ico, A. Myung, B. S. Kim, N. V. Myung, J. Nam, *Nanoscale* 2018, 10, 2894). As for the piezoelectric inactivation of the PVDF scaffolds, a proper thermal treatment is necessary to convert its electro-active phase contents, which arise from the electrospinning process that intrinsically subjects the polymer to piezoelectricity-rendering mechanical stretching and electrical biasing, back to the inactive α-phase. The DSC curve (FIG. 37, b) shows that a tightly controlled thermal treatment around 158° C., but below 170° C., can inactivate PVDF scaffolds by promoting the phase transition of β-phase towards the α-phase while not completely melting the fibrous structure. Others have reported that the first peak at 158.7° C. is due to the β-phase transition and the latter peak at 170.0° C. is due to the presence of α-phase content not transformed to the β-phase during electrospinning (W. Steinmann, S. Walter, G. Seide, T. Gries, G. Roth, M. Schubnell, *Journal of Applied Polymer Science* 2011, 120, 21). Both thermal treatments, 90° C. for 24 hrs for P(VDF-TrFE) and 158° C. for 1 hr for PVDF, have no effect on the morphology of the nanofiber scaffolds (FIG. 76, c). Confirmation of the inactivation of PVDF is demonstrated by piezo-response force microscopy (PFM), which showed a reduction in the piezoelectric coefficient of the as-spun PVDF at $-31\pm8$ μm V$^{-1}$ to a negligible value of $-6\pm2$ μm V$^{-1}$ from the thermally inactivated PVDF (FIG. 37, d). In comparison, the heat-treated P(VDF-TrFE) has an enhanced piezoelectric coefficient of $-37\pm4$ μm V$^{-1}$ as compared to $-32\pm3$ μm V$^{-1}$ of the as-spun form.

The electrical characteristics of these heat-treated scaffolds were measured using the hydro-acoustic actuation system as described earlier (FIG. 36). The effects of the heat-treatments were evident from the induction of voltage peaks in the P(VDF-TrFE) scaffolds while the heat-inactivated PVDF scaffolds produced significantly reduced voltage peaks (FIG. 76, e). As a function of applied strain, the peak-to-peak voltage generated at the surface of the scaffolds showed a linear trend for P(VDF-TrFE) (FIG. 37, f). In contrast, due to the heat-inactivation, a negligible voltage was generated for the PVDF scaffold up until 0.03% strain. From our preliminary study, where PC12 cells were subjected to externally applied AC voltages with a similar profile to the hydro-acoustic generated voltages from the piezoelectric scaffolds, a voltage of 200 mV$_{p-p}$ was determined as the necessary stimulation to enhance the neuronal behaviors (neurite formation and elongation). Thus, a strain of 0.03% to produce approximately 200 mV$_{p-p}$ from the P(VDF-TrFE) scaffolds and an insignificant voltage of the PVDF scaffolds was chosen for all subsequent studies. These heat treatment regimens, specifically designed for each PVDF derivative, significantly manipulated their piezoelectric properties, enabling the dissection of the effects of hydro-acoustically induced electric stimulation on cellular behaviors by comparing the piezoelectric P(VDF-TrFE) scaffold with the heat-inactivated PVDF scaffold.

To examine the effects of mechano-electrical stimulation on neuronal cells via the hydro-acoustic activation of the piezoelectric scaffolds, PC12 cells were seeded on aligned heat-enhanced P(VDF-TrFE) or heat-inactivated PVDF scaffolds. The cell scaffold constructs were pre-cultured for 2 days prior to being either statically cultured continuously or subjected to the hydro-acoustic stimulation for 2 hrs per day for the subsequent 5 days, making a total culture duration of 7 days. The specific dynamic strain regimen was chosen for the P(VDF-TrFE) scaffolds to produce approximately 200 mV$_{p-p}$. Immunofluorescent imaging was utilized to examine the neurite length relative to the nucleus length in each condition (FIG. 38, a-e). The actuated piezoelectric P(VDF-TrFE) condition showed the greatest average neurite length, exhibiting an increase in neurite elongation by approximately 75% when compared to the static, inactivated PVDF scaffold. The effects of piezoelectric material-induced electrical stimulation are evident by the approximate 35% increase in neurite length in the actuated P(VDF-TrFE) scaffolds as compared to the static P(VDF-TrFE) scaffolds. Interestingly, the hydro-acoustic actuation itself promoted neuronal behaviors of the cells, enhancing the neurite extension by approximately 36% when the two conditions of the inactivated PVDF scaffolds were compared. Furthermore, static culture on the piezoelectric scaffolds also promoted neurite elongation by approximately 30% over static culture on the inactivated scaffolds, agreeing with other studies that showed enhanced neuronal cell behaviors by simple culture on piezoelectric materials (Y. S. Lee, T. L. Arinzeh, *Tissue Eng Pt A* 2012, 18, 2063; Y.-S. Lee, G. Collins, T. L. Arinzeh, *Acta biomaterialia* 2011, 7, 3877; and N. Royo-Gascon, J. I. Wininger M Fau-Scheinbeim, B. L. Scheinbeim Ji Fau-Firestein, W. Firestein B1 Fau-Craelius, W. Craelius, *Ann Biomed Eng* 2013, 41, 112). Neurite length distribution in the cell population for each condition showed that the actuated P(VDF-TrFE) scaffold condition had a population shift towards greater neurite lengths and narrower distribution compared to all other conditions (FIG. 38, f). Cells having their neurite greater than 10 times of their nucleus size were only present in the P(VDF-TrFE) scaffolds, with a greater population in the actuated condition. In comparison to aligned conductive polymer PLLA-graphene oxide scaffolds used to induce PC12 cell neurite length of 90 μm in 6 days (K. Zhang, H. Zheng, S. Liang, C. Gao, *Acta biomaterialia* 2016, 37, 131), our study showed that the cells, exposed to multi-day piezoelectric stimulation using the optimized P(VDF-TrFE) scaffolds, exhibited significantly enhanced neurite formation up to 500 μm in merely five days of stimulation and 60% of the population possessed neurites (FIG. 39). These results clearly demonstrate the synergistic effects of mechanical (hydro-acoustic) and electrical (piezoelectric) stimulations on the functional enhancements in neuronal cells, and signify the potential of the piezoelectric scaffolds with appropriate activation for in vitro nerve tissue engineering and in vivo nerve regeneration. Typical peripheral nerve architecture requires several long-extended neurons rather than many short neurons, and the observation of significantly enhanced neurite extension in the activated piezoelectric scaffolds is promising for the generation of in vitro nerve model with physiological similarities. Furthermore, considering the relatively porous structure of electrospun P(VDF-TrFE) scaffolds that allows for selective diffusion of macromolecules and neurotrophic factors, our results demonstrate the potential of P(VDF-TrFE) to enhance nerve regeneration in vivo.

In addition to neuronal cells, the effects of mechano-electrical stimulation via the hydroacoustic activation of the piezoelectric scaffolds on glial cells were also examined. Rat Schwann cells (RSC96) were seeded on similar scaffolds and pre-cultured for 2 days before subjecting the cell/scaffold constructs to the dynamic regimen of hydro-acoustic stimulation for 2 hrs per day for the subsequent 5 days or maintained statically. The gene expression of Schwann cell markers including myelin-specific proteolipid protein (Plp), early growth response protein 2 (Krox20 or Egr2), and myelin basic protein (Mbp) were compared among the conditions (FIG. 80, a-c). Interestingly, mechanical stimulation alone had the greatest impact on early pro-myelinating proteins, Plp and Krox20. However, the expression of Mbp, a mature Schwann cell marker, was synergistically enhanced by mechanical and electrical stimulation, suggesting that the effects of mechano-electrical stimulation depend on the developmental stage of the cell lineage (K. R. Jessen, R. Mirsky, *Nature reviews. Neuroscience* 2005, 6, 671). Immunofluorescent imaging showed that the cells grew in large colonies on both scaffolds under static culture, similar to the cells cultured on tissue culture plates (FIG. 40, *d* and *f*). In contrast, the actuated culture for both scaffolds induced more single cell formation (FIG. 40, *e* and *g*). Considering the fact that we did not observe cell detachment under the actuation conditions during the culture, it appears that mechanical stimulation (i.e., hydro-acoustic stimulation) suppresses cell proliferation. This observation coincides with the enhanced expression of nerve growth factor (NGF), an influential neurotrophic factor for neuronal regeneration, in Schwann cells on both the actuated PVDF and P(VDF-TrFE) scaffolds. Overall, our results demonstrate that mechanical stimulation from the hydro-acoustic actuation induces enhanced function of Schwann cells by promoting the expression of myelin building proteins and favorable neurotrophic factors as similarly observed in other studies (S. Belin, K. L. Zuloaga, Y. Poitelon, *Frontiers in cellular neuroscience* 2017, 11, 347). Furthermore, the electrical stimulation arose from the piezoelectric effect, i.e., activated P(VDF-TrFE) scaffold, appears to synergistically enhance the Schwann cell function maturation process, evident from the expression of Mbp, S100b and Mpz (FIG. 40, c).

We next examined the effects of mechano-electrical stimulation on the differentiation capacity of NSCs towards neuronal, oligodendrocytic, or astrocytic cells (FIGS. 41-43). The expression of Tubb3, an early neuronal marker, was significantly enhanced by the hydro-acoustic mechanical stimulation while mature neuronal markers, including Map2 and Eno2, were slightly downregulated in the cells on the PVDF scaffolds but significantly upregulated on the P(VDF-TrFE) scaffolds (FIG. 41, a-c). Protein expression of β-III tubulin under various culture conditions corroborate with those found in the gene expression study. The cells on the actuated piezoelectric scaffold showed a similar expression level of β-III tubulin, but with the formation of longer extended neurites, indicating more developmentally mature neurons. In contrast, the inactive PVDF scaffold showed less mature neurons (i.e., shorter extended axons) (FIG. 41, d-g). However, all scaffolds showed some expression of the neuronal marker likely due to the aligned morphology of the scaffolds inducing neuronal differentiation of the cells. The expression of oligodendrocytic genes, Olig1, Cldn11 and Mog, showed a similar developmental stage-dependent effect of mechano-electrical stimulation (FIG. 42, a-c). The formers, Olig1 and Cldn11 are intermediate markers for neural stem cell differentiation towards oligodendrocyte (S. A. Goldman, N. J. Kuypers, *Development* 2015, 142, 3983), and they were significantly upregulated by the mechanical stimulation. In contrast, Mog, which was significantly upregulated by the piezoelectric material-induced electrical stimulation, is expressed on the outermost surface of myelin sheaths indicative of more mature oligodendrocytes. Both of these oligodendrocytic marker genes were significantly upregulated by the. More strikingly, the protein expression of MBP (myelin basic protein) was only observed in the actuated P(VDF-TrFE) scaffolds, supporting the notion that electrical stimulation promotes NSC differentiation and maturation towards myelinating oligodendrocytes (FIG. 42, d-g). Regarding the differentiation of NSCs towards the astrocyte phenotype, the results also showed a similar expression pattern; significant upregulation was observed under the mechanical stimulation for early/intermediate astrocytic genes, Aldh1l1 and Cspg4, while the piezoelectric material-induced electrical stimulation enhanced the expression of Gfap, an astrocytic functional marker. Gfap encodes a major filament protein in mature astrocytes, allowing the ability to distinguish these cells types from the other glial cell types (i.e., oligodendrocytes). In regards to the specific astrocyte cell-type, Cspg4 is known to be expressed in reactive astrocytes (V. Rusnakova, P. Honsa, D. Dzamba, A. Ståhlberg, M. Kubista, M. Anderova, *PLoS One* 2013, 8, e69734); i.e., astrocytes involved in the phagocytosis of synapses, secretion of specific neurotrophins, and clearance of debris and dead cells, following injury to the central nervous system (CNS) (S. A. Liddelow, B. A. Barres, *Immunity* 2017, 46, 957). It has been thought that some of these reactive astrocytes prevent full axon regeneration in the CNS following injury. However, recently it has been shown that the same scar-forming astrocytes also express multiple axon-growth-supporting molecules as well as the Cspg4 gene necessary for axons regeneration (M. A. Anderson, J. E. Burda, Y. Ren, Y. Ao, T. M. O'Shea, R. Kawaguchi, G. Coppola, B. S. Khakh, T. J. Deming, M. V. Sofroniew, *Nature* 2016, 532, 195). At the protein level, the expression of EAAT2, an astrocyte marker, was observed only in the actuated piezoelectric P(VDF-TrFE) condition, signifying the potency of piezoelectric derived electrical stimulation on the astrocytic maturation of NSCs (FIG. 43, c-f). These results demonstrate that the combination of the mechanical and electrical stimulations, derived from the hydro-acoustic activation of the piezoelectric scaffold, synergistically induce the differentiation and maturation of NSCs simultaneously towards all neuronal cell types. More specifically, the mechano-electrical stimulation via the activated piezoelectric scaffolds promotes the production of mature, elongated neurons in the presence of myelinating oligodendrocytes and axon-regeneration promoting astrocytes, potentially offering a solution for stem cell derived tissue formation composed of multiple cell phenotypes. Therefore, the technology may overcome the limitations of current in vitro models that are restricted to either the single cell levels or simple co-culture systems of neurons and glial cells without structural elements, failing to accurately account for tissue level complexity (S. Geuna, S. Raimondo, F. Fregnan, K. Haastert-Talini, C. Grothe, *The European journal of neuroscience* 2016, 43, 287).

There have been several attempts to utilize piezoelectric PVDF and its derivatives for in vitro and in vivo nerve regeneration (Y. S. Lee, T. L. Arinzeh, Tissue Eng Pt A 2012, 18, 2063; Y.-S. Lee, G. Collins, T. L. Arinzeh, Acta biomaterialia 2011, 7, 3877; P. Aebischer, R. F. Valentini, P. Dario, C. Domenici, P. M. Galletti, *Brain Res* 1987, 436, 165; and Y. S. Lee, S. L. Wu, T. L. Arinzeh, M. B. Bunge, *Biotechnol Bioeng* 2017, 114, 444.), demonstrating the material's ability to enhance the regenerative behaviors of neural cells. However, those studies did not effectively utilize the full potential of piezoelectricity due to the lack of active mechanical straining to realize the electric potential generation to further stimulate nerve cells. Although a recent study utilized ultrasound as a mechanical cue to induce piezoelectric effects from a PVDF membrane and showed anabolic responses from PC12 cells, the high frequency used in the study is not likely to generate meaningful magnitudes of electrical potentials to affect cellular behaviors (M. Hoop, X. Z. Chen, A. Ferrari, F. Mushtaq, G. Ghazaryan, T. Tervoort, D. Poulikakos, B. Nelson, S. Pane, *Scientific reports* 2017, 7, 4028). In comparison, we demonstrated that cells exposed to dynamic piezoelectric stimulation exhibited significantly enhanced neurite formation/elongation of neurons, neurotrophic factor secretion of Schwann cells, and multi-phenotypic differentiation of NSCs, as compared to statically cultured cells on P(VDF-TrFE) scaffolds, where the activities of statically cultured cells would be equivalent to those from the aforementioned studies. This was possible by our systematic approach to optimize piezoelectric properties of P(VDF-TrFE) with thorough material characterization, in order to generate an appropriate electric potential to stimulate neural cells by non-contact mechanical perturbation.

In summary, a mechano-electrical stimulation strategy built upon a biocompatible piezoelectric scaffold of aligned P(VDF-TrFE) nanofibers was developed and utilized to induce functional enhancement of various neural cell phenotypes. Specifically, the conversion of mechanical to electrical stimulation, through the piezoelectric effect is directly responsible for the increase in neurite extension while the hydro-acoustic mechanical stimulation enhanced the expression of neurotrophic and myelin related proteins in Schwann cells. Furthermore, a significant enhancement in the multi-phenotypic differentiation of mouse neural stem cells towards neuron, oligodendrocyte, and astrocyte cell phenotypes were achieved by the synergistic effects of mechanical and electrical stimulations utilizing this piezoelectric material-based platform. These results implicate the potential for addressing current limitations for studying genetic and age-related diseases, as well as repairing mechanical injuries. For the former, the platform may be used to create patient-specific in vitro models towards the understanding of the pathologies of genetic associated diseases. For the latter, nerve tissue regeneration and complete reinnervation, which is limited in current nerve conduits, may be possible by the implantation of these non-conductive (will not negatively impact normal nerve conduction), yet on-demand, electric potential generating scaffolds under mechanical actuation in a physiologically safe manner, as a guidance for nerve regeneration. An in vivo application test by implanting the conduit to the sciatic nerve location in a rat cadaver demonstrated the feasibility of activating the conduit by utilizing the shockwave system (FIG. 44).

Synthesis and Morphological Characterization of P(VDF-TrFE) Scaffolds

P(VDF-TrFE((Solvay Group, France) was dissolved at various concentrations in different solvent systems to produce a range of different electrospun fiber diameters, similar to our previous report (16). A 16 wt. % P(VDF-TrFE) (70:30 mol %) was dissolved in a 60/40 volume ratio of N,N-dimethylformamide (DMF) (Sigma Aldrich, St. Louis, MO) to methyl ethyl ketone (MEK) (Sigma Aldrich) solvent system, resulting in an average fiber diameter of 802±16 nm. 5 wt. % and 7 wt. % P(VDF-TrFE) were dissolved in a 60/40 volume ratio of DMF to acetone solvent system, with the addition of 1 wt. % pyridinium formate (PF) buffer (Sigma Aldrich), resulting in an average fiber diameter of 205±28 nm and 498±57 nm, respectively. The solution was magnetically stirred at 1200 rpm for 3 hrs at room temperature until the solution turned clear. As the basis for a piezoelectric inactivated control, a solution of 13.5 wt. % of PVDF dissolved in the same DMF/acetone/PF solvent system was created. Each solution was electrospun under optimized conditions of electrospinning distance (10 cm), applied voltage (approximately −15 to −20 kV) and solution feed rate (6 ml hr$^{-1}$) at 23° C. and an absolute humidity of approximately 7.6 g m$^{-3}$. The formed fibers were collected onto a high-speed, grounded mandrel rotating at an angular velocity of 47.9 m s$^{-1}$ for 4 hrs to yield scaffolds of aligned fibers having a thickness of approximately 200 μm. The P(VDF-TrFE) scaffolds were subsequently annealed at 90° C. for 24 hrs which we have previously shown to enhance the piezoelectric properties (G. Ico, A. Myung, B. S. Kim, N. V. Myung, J. Nam, *Nanoscale* 2018, 10, 2894). The PVDF fibers were thermal treated for 1 hr in a rapid thermal annealing oven (Allwin21 Corp) at 157° C., to induce the electroactive- to α-phase transition without causing melting of the fibrous structure, followed immediately by quenching in cold ethanol to preserve the non-piezoelectric α-phase.

Piezoelectric Characterization of Electrospun Nanofibers

To properly measure the piezoelectric coefficient, a standard periodically poled lithium niobate (PPLN) with a known piezoelectric coefficient was used to determine a correction factor for all subsequent measurements. Nanofibers of P(VDF-TrFE) and PVDF were sparsely collected on a gold coated, thermal-oxide silicon substrate and subjected to single-point piezoresponse force microscopy on individual fibers. An MFP-3D AFM (Asylum Research, Santa Barbara, CA) was first used in tapping imaging mode to locate an individual fiber. Five points were chosen on the scanned fiber and the AFM was switched to PFM where single point spectroscopy measurements were conducted. Step voltages from −3 to +3 V was applied across the fiber via the AFM cantilever (AC240™, Olympus) to the grounded substrate. The value of $d_{33}$ was calculated by, $$d_{33} = \frac{A}{VQ} f,$$

where A is the amplitude response of the nanofiber in response to an applied voltage (V), Q is the quality factor of the AFM cantilever, and f is the correctional factor taken from the PPLN standard.

A piezoelectric cell culture system, based on 3-D printed acrylonitrile butadiene styrene (ABS) chambers (FIG. 71, a), was engineered to contain and apply a non-contact mechanical stimulation to induce the piezoelectric effect of the nanofibrous P(VDF-TrFE) scaffold by vertical translation of a stage fixed on a subwoofer. The chambers were designed to fit within a well of a typical 6-well tissue culture plate. The subcomponents of the chamber consist of top and bottom mating surfaces each with silicone o-rings serving to both create fixed points for the scaffold and create a mechanical seal when both surfaces are mated with stainless steel screws. The cylindrical nature of the chambers allows the suspension of the scaffold thus promoting an unrestricted region for the scaffold to deflect in response to the indirect mechanical stimulation in an aqueous solution (hydro-acoustic waves).

To quantify the voltage generated across the P(VDF-TrFE) scaffolds or absence of voltage generated across the control PVDF scaffolds, acellular scaffolds were subjected to the acoustic stimulation inside the cell culture system. Scaffolds were cut to the dimensions of 45×5 mm$^2$. Gold electrodes with the dimension 40×4 mm$^2$ were sputtered on both sides of the scaffolds (FIG. 36, b). A hydrophobic poly(styrene-block-isobutylene-block-styrene) (SIBS, Sibstar, Kaneka, Pasadena, TX) coating was applied, via brush from a 30 wt. % SIBS in toluene (Fisher Scientific, Pittsburgh, PA) solution, on top of gold sputtered surfaces to prevent an electrical short circuit. The processed scaffold was assembled into the cell culture chamber and 2 mL of water was added into the center region of the chamber submerging the scaffold. The chamber was placed on the vertical translating stage and various magnitudes of strains were applied indirectly to the scaffold by driving various amplitudes of a 3 Hz pulse signal via a LabVIEW-controlled function generator bridged to the subwoofer by an amplifier. The generated voltage across the scaffold was simultaneously measured by an oscilloscope (Pico Technologies, St. Neots, UK). The magnitude of applied strain was correlated to the matched output voltage generated by our previously designed cantilever system (G. Ico, A. Showalter, W. Bosze, S. C. Gott, B. S. Kim, M. P. Rao, N. V. Myung, J. Nam, *Journal of Materials Chemistry A* 2016, 4, 2293.

Phase Transition Analysis of Electrospun PVDF Nanofibers

Determination of the different phase transition temperatures of electrospun P(VDF-TrFE) and PVDF nanofibers was conducted using a differential scanning calorimeter (NETZSCH DSC 214 Polyma, Wittelsbacherstraße 42, Germany). DSC curves were acquired by heating a sample of 6.9 (P(VDF-TrFE) and 5.9 mg (PVDF) from 25° C. to 230° C. at a heating rate of 2.5° C./min in air.

Cell Culture

Three different phenotypes of neural cells including PC12, RSC96 and neural stem cells were utilized in this study. PC12 cells, a rat adrenal pheochromocytoma cell line, were purchased from ATCC (Manassas, VA). The cells were maintained on tissue culture plates coated with type I collagen from rat tail (Sigma Aldrich) in F12K medium (ATCC), supplemented with 15% horse serum (Sigma Aldrich), 2.5% fetal bovine serum (FBS, VWR, Radnor, NJ), and 1% antimycotic/antibiotic solution (Corning, Corning, NY). Immortalized rat neuronal Schwann cells (RSC96) were purchased from ATCC (Manassas, VA). They were cultured in high glucose Dulbecco's Modified Eagle Medium (DMEM, Lonza, Morristown, NJ), supplemented with 10% fetal bovine serum (FBS, VWR, Radnor, NJ) and 1% penicillin/streptomycin (Mediatech, Manassas, VA). C17.2 neural stem cells (NSCs), derived from the cerebellum of neonatal mouse, were cultured in high glucose DMEM, supplemented with 10% FBS (VWR, Radnor, PA), 5% horse serum (Gibco, Gaithersburg, MD), 1% sodium pyruvate (Gibco), and 1% penicillin/streptomycin.

Following thermal treatment of the P(VDF-TrFE) and PVDF scaffolds, 40×5 mm² strips of each were prepared and a layer of SIBS coasting was applied to the periphery to isolate a 7 mm×5 mm cell culture area at the center of the scaffold (FIG. 71, c). The scaffolds were centered and bridged across the culture chambers, as described for the voltage measurement, and assembled to yield the final piezoelectric cell culture system which was gamma irradiated for sterilization at a dose of 10 kGy (E. Eljarrat-Binstock, A. Bentolila, N. Kumar, H. Harel, A. J. Domb, *Polymers for advanced technologies* 2007, 18, 720). After sterilization, the cell culture area of each scaffold was pre-wetted with 70% ethanol, washed several times with PBS, and coated overnight with 20% FBS in DMEM. PC12, RSC96 and neural stem cells were individually seeded onto each scaffold at a density of 2,000, 5,000 and 1,000 cells per cm², respectively. The cell/scaffold constructs were pre-cultured for 2 days in the normal growth media as described earlier, except the supplementation of nerve growth factor (Sigma Aldrich) at 50 ng/ml for PC 12 cells.

Hydro-Acoustic Actuation

Following the 2 day pre-culture period, the cell/scaffold constructs were subjected to hydro-acoustic actuation. The actuation chambers loaded with cell/scaffold constructs were placed in a 6-well plate, and subjected to actuation by the vertical translational stage to apply a surface strain of approximately 0.03%. The actuation regimen was experimentally determined to generate 200 $mV_{p-p}$ for an approximately 200 μm thick P(VDF-TrFE) scaffold when oscillating at 3 Hz. The cell/scaffold constructs were actuated daily for 2 hrs for 5 days. As controls, cells were cultured in the cell culture system statically as well as on tissue culture plates for the same duration. After 24 hrs from the last mechanical stimulation on the seventh day post cell seeding, cells were subjected to 4% paraformaldehyde (PFA) fixation for immunofluorescence analysis or lysed for gene expression analysis.

Morphological Characterization of PC12 Cells

Immunofluorescent images of the PC12 cell cultures on all conditions were analyzed in order to compare their neurite growth. To visualize the elongation of neurites PC12 cells were stained with DAPI and Phalloidin (Alexa Fluor-594, Invitrogen, Carlsbad, CA) for visualization of the cell nucleus and actin filament, respectively. ImageJ, an image processing software, was utilized to measure the cell body elongation length and nucleus length. Cell body elongation length was the summation of the length from one side of the cell to the center of nucleus and from the other side of the cell body to the center of nucleus. Statistical analysis was performed in order to calculate the cell body to nucleus elongation ratio. This ratio was used to compare the differentiation characteristics of the cells.

Protein Expression Analysis

To determine the effects of piezoelectric stimulation on the production of NGF by RSC96, NGF receptors on the cells were stained with anti-NGF (Santa Cruz Biotechnology, Dallas, TX) as the primary antibody and with Alexa Fluor-594 (Jackson ImmunoResearch, West Grove, PA) as the secondary antibody. The samples were subsequently counter-stained with 4',6-Diamidino-2-Phenylindole (DAPI, Vector Laboratories, Burlingame, CA) for nuclei and Alexa Fluor 488-conjugated Phalloidin (Invitrogen, Carlsbad, CA) for actin.

To characterize the differentiation associated protein expression of NSCs towards neuronal or glial cells promoted by piezoelectric stimulation, fixed cells were immunostained with primary antibody markers specific for either neurons (βIII tubulin, Thermo Fisher Scientific, Waltham, MA), oligodendrocytes (MBP, Santa Cruz Biotechnology, Dallas, TX), or astrocytes (EAAT2, Santa Cruz Biotechnology) with the appropriate secondary mouse binding protein marker (m-IgGκ BP-CFL 488, Santa Cruz Biotechnology). The samples were counter-stained with DAPI and phalloidin conjugated with Alexa Fluor-594 for visualization of the cell nucleus and actin filament, respectively, followed by analysis using immunofluorescence microscopy (Eclipse Ti, Nikon, Melville, NY).

Gene Expression Analysis

The effects of piezoelectric stimulation on RSC96 and mNSC gene expression after a total culture duration of 7 days were determined at the gene level by quantitative polymerase chain reaction (qPCR). Total RNA was extracted using an RNeasy Micro Kit (Qiagen, Valencia, CA), and cDNA synthesis was performed using iScript cDNA Synthesis Kit (Bio-Rad, Hercules, CA) according to manufacturers' protocols. qPCR was performed to determine the gene expression of myelinating factors of rat RSC96s (Table 6) and phenotypic markers for mouse NSCs (Table 7). Data were analyzed by the comparative threshold cycle ($C_T$) method using Rps18 for RSC96 cells and Gapdh for NSCs as an endogenous control.

TABLE 6

| Marker | Primer | Forward | SEQ ID No | Reverse | SEQ ID No |
|---|---|---|---|---|---|
| Housekeeping | RPS18 | 5'-CCCGAGAAGTTTCAGCACATC-3' | 1 | 5'-ATGGCAGTGATAGCGAAGGCT-3' | 6 |
| | Plp | 5'-GGTTCCAGAGGCCAACATCAA-3' | 37 | 5'-AGGCAAACACCAGGAGCCATA-3' | 38 |
| | Krx20 | 5'-TGCGCCTAGAAACCAGACCTT-3' | 3 | 5'-ATGCCCGCACTCACAATATTG-3' | 8 |
| | Mbp | 5'-AGCAAGTACCATGGACCATGC-3' | 39 | 5'-TAAAGAAGCGCCCGATGGA-3' | 40 |

TABLE 7

| Marker | Primer | Forward | SEQ ID No | Reverse | SEQ ID No. |
|---|---|---|---|---|---|
| Housekeeping | Gapdh | 5'-GGCAAATTCAACGGCACAGT-3' | 11 | 5'-TCGCTCCTGGAAGATGGTGAT-3' | 24 |
| Neuron | Tubb3 | 5'-ACCTTGTGTCTGCCACCATGA-3' | 15 | 5'-CACCATGTTCACAGCCAGCTT-3' | 28 |
| | Map2 | 5'-AAGCCATTGTGTCCGAACCA-3' | 16 | 5'-GAGCGGAAGAGCAGTTTGTCA-3' | 29 |
| | Eno2 | 5'-ATCGCCACATTGCTCAGCTAG-3' | 17 | 5'-TGAGAGCCACCATTGATCACA-3' | 30 |
| Oligodendrocyte | Olig1 | 5'-ACGCCAAAGAGGAACAGCA-3' | 18 | 5'-TCCATGGCCAAGTTCAGGT-3' | 31 |
| | Cldn11 | 5'-TGGCATCATCGTCACAACGT-3' | 19 | 5'-CCCAGTTCGTCCATTTTTCG-3' | 32 |
| | Mog | 5'-TGCCCTGCTGGAAGATAACAC-3' | 20 | 5'-TGCAGCCAGTTGTAGCAGATG-3' | 33 |
| Astrocyte | Aldh1/1 | 5'-AGTGATGTTGACAAGGCGGTG-3' | 41 | 5'-CGGTCACGCGCATTTATCTT-3' | 42 |
| | Cspg4 | 5'-CTGAGCAATCTGTCTTTCCCAGT-3' | 22 | 5'-TGTGTATGCAGAGGTTCAAGCCT-3' | 35 |
| | Gfap | 5'-TGGAGCTCAATGACCGCTTT-3' | 21 | 5'-GCTCGAAGCTGGTTCAGTTCA-3' | 34 |

Statistical Analysis

Statistical analysis was performed with at least three biologically independent samples and represented as an average±standard deviation (SD) or standard error of mean (SEM) as indicated. The data were subjected to ANOVA with Tukey's post-hoc test using the SPSS software (IBM) to determine statistical significance ($p < 0.05$).

While the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein. Each and every feature described herein, and each and every combination of two or more of such features, is included within the scope of the present invention provided that the features included in such a combination are not mutually inconsistent.

All figures, tables, and appendices, as well as patents, applications, and publications, referred to above, are hereby incorporated by reference.

Some embodiments have been described in connection with the accompanying drawing. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A method of activating a piezoelectric neuroconduit guide scaffold comprising a plurality of aligned piezoelectric polymer nanofibers, the method comprising mechanically stimulating the piezoelectric neuroconduit guide scaffold with hydro-acoustic waves or shockwaves to remotely activate a piezoelectric effect of the nanofibrous scaffolds that induces a mechano-electrical stimulus on neural cells cultured on the scaffold, wherein the mechano-electrical stimulus promotes nerve fiber outgrowth from the neuronal cells.

2. The method of claim 1, wherein the piezoelectric scaffold is mechanically stimulated in a non-contact manner in vitro using a cell culture chamber with a vertical actuator.

3. The method according to claim 2, comprising applying a mechanical strain having a strain of 0.02% to 0.04% with hydro-acoustic waves.

4. The method of claim 1, wherein the piezoelectric neuroconduit guide scaffold is mechanically stimulated in a non-contact manner in vivo using extracorporeal shockwave therapy (ESWT).

5. The method according to claim 4, comprising applying a sonic pulse of mechanical energy having a positive peak within about 10 ns, followed by a negative peak up to about −10 MPa, with a total life cycle of about 10 μs.

6. The method of claim 1, wherein the hydro-acoustic waves or shockwaves generate a peak-to-peak voltage from the piezoelectric scaffolds of about 200 mVp-p, by simultaneously controlling individual fiber diameter and fiber mat thickness.

7. The method of claim 1, wherein the neuronal cells are selected from the group consisting of neurons, Schwann cells and neural stem cells.

8. The method of claim 1, wherein the nanofibers have an average diameter of from 100-1000 nm.

9. The method of claim 1, wherein the piezoelectric neuroconduit guide scaffold comprises a fiber mat thickness of 40 to 400 μm.

10. The method of claim 1, wherein the nanofibers are all aligned within 200 of the neutral axis.

11. The method of claim 1, wherein the nanofibers are heat-treated.

12. The method of claim 1, wherein the piezoelectric polymer is poly(vinylidene fluoride) (PVDF) or a derivative thereof.

13. The method of claim 12, wherein said derivative of PVDF is P(VDF-trifluoroethanol) (PVDF-TrFE).

14. The method of claim 1 comprising seeding individual components of neural tissues including neuron and Schwann cells, or neural stem cells on the piezoelectric neuroconduit guide scaffold, wherein the hydro-acoustic stimulation of the piezoelectric neuroconduit guide scaffold and the neural tissues induces neural tissue formation.

15. The method claim 14, wherein the neural tissue formation is in vitro.

16. The method of claim 1, wherein the piezoelectric neuroconduit guide scaffold is implanted in a damaged neural tissue, wherein the piezoelectric neuroconduit guide scaffold is positioned to bridge a nerve gap in the damaged neural tissue, and wherein stimulating the piezoelectric neuroconduit guide scaffold by the application of shockwaves promotes nerve fiber outgrowth, and wherein the implanted scaffold and neurite outgrowth bridges the nerve gap to induce nerve regeneration or reinnervation of the damaged neural tissue.

17. The method of claim 16, wherein the neural tissue is in vivo.

18. The method of claim 16, wherein the nerve gap is larger than 30 mm.

19. The method of claim 16, wherein cellular activities of Schwann cells, or myelinating oligodendrocytes and extracellular matrix-producing astrocytes promote nerve regeneration within a PNS or CNS injury, respectively.

20. The method of claim 16, wherein the damaged neural tissue is in the peripheral nervous system (PNS).

21. The method of claim 20, wherein activating the piezoelectric neuroconduit guide scaffold induces upregulation of gene expression of one or more of pro-myelinating Schwaan cell markers, NGF, Krox20 or PMP22 and/or suppression of the immature Schwaan cell marker, NCAM-1.

22. The method of claim 16, wherein the damaged neural tissue is in the central nervous system (CNS).

23. The method of claim 22, wherein activating the piezoelectric neuroconduit guide scaffold induces upregulation of gene expression of one or more of oligodendrocyte cell markers, Olig1, Cldn11 and Mog and/or one or more astrocyte cell markers, Gfap, Cspg4 and Ntf3.

\* \* \* \* \*